(12) United States Patent
Wengreen et al.

(10) Patent No.: US 9,956,140 B2
(45) Date of Patent: May 1, 2018

(54) STORAGE SYSTEMS AND METHODS FOR MEDICINES

(71) Applicants: Sandy Wengreen, Sammamish, WA (US); Eric John Wengreen, Sammamish, WA (US)

(72) Inventors: Sandy Wengreen, Sammamish, WA (US); Eric John Wengreen, Sammamish, WA (US)

( * ) Notice: Subject to any disclaimer, the term of this patent is extended or adjusted under 35 U.S.C. 154(b) by 64 days.

(21) Appl. No.: 15/151,446

(22) Filed: May 10, 2016

(65) Prior Publication Data
US 2016/0251140 A1 Sep. 1, 2016

Related U.S. Application Data

(63) Continuation-in-part of application No. 14/849,884, filed on Sep. 10, 2015, now Pat. No. 9,707,156, which
(Continued)

(51) Int. Cl.
| | |
|---|---|
| *F25D 25/00* | (2006.01) |
| *A61J 1/16* | (2006.01) |
| *F25D 3/08* | (2006.01) |
| *A61M 5/00* | (2006.01) |
| *A61J 1/18* | (2006.01) |

(Continued)

(52) U.S. Cl.
CPC .............. *A61J 1/165* (2013.01); *A61J 1/18* (2013.01); *A61M 5/002* (2013.01); *B65B 63/08* (2013.01); *B65D 81/383* (2013.01); *F25D 3/08* (2013.01); *A61J 1/1418* (2015.05); *A61J 2200/40* (2013.01); *A61J 2200/50* (2013.01); *A61J 2200/72* (2013.01); *A61J 2200/74* (2013.01); *A61J 2205/60* (2013.01); *A61J 2205/70* (2013.01); *A61M 2005/3125* (2013.01); *A61M 2205/127* (2013.01); *A61M 2205/3368* (2013.01); *A61M 2205/3633* (2013.01); *A61M 2205/50* (2013.01); *A61M 2205/581* (2013.01); *A61M 2205/8206* (2013.01); *F25D 2303/085* (2013.01); *F25D 2303/0822* (2013.01); *F25D 2303/0843* (2013.01); *F25D 2303/08221* (2013.01); *F25D 2303/08222* (2013.01)

(58) Field of Classification Search
CPC ........ F25D 3/10; F25D 3/08; F25D 2331/804; A01N 1/02
USPC .................................. 62/62, 371, 457.1, 530
See application file for complete search history.

(56) References Cited

U.S. PATENT DOCUMENTS

| | | | |
|---|---|---|---|
| 2,263,865 | A | 11/1941 | Lewis |
| 3,034,845 | A | 5/1962 | Haumann |

(Continued)

OTHER PUBLICATIONS

Wikipedia Article: "Phase Change Material," downloaded Feb. 5, 2015 from http://en.wikipedia.org/wiki/Phase-change_material.
(Continued)

*Primary Examiner* — Melvin Jones

(57) ABSTRACT

People can damage their medicines by taking them outside in hot or cold weather. On the other hand, some people need to carry their medicines with them wherever they go (even if the weather is extremely hot or cold). Specially constructed storage systems can protect medicines from damage due to hot and cold weather without requiring bulky structures or expensive components that consume electricity to regulate temperature.

37 Claims, 44 Drawing Sheets

Related U.S. Application Data is a continuation-in-part of application No. 14/616,652, filed on Feb. 6, 2015, now Pat. No. 9,151,531.

(60) Provisional application No. 62/293,691, filed on Feb. 10, 2016.

(51) Int. Cl.
| | |
|---|---|
| *B65B 63/08* | (2006.01) |
| *B65D 81/38* | (2006.01) |
| *A61M 5/31* | (2006.01) |
| *A61J 1/14* | (2006.01) |

(56) References Cited

U.S. PATENT DOCUMENTS

| | | | |
|---|---|---|---|
| 3,401,692 A | 9/1968 | Harris | |
| 3,872,864 A | 3/1975 | Allen | |
| 3,910,441 A | 10/1975 | Bramming | |
| 3,961,720 A | 6/1976 | Potter | |
| 4,287,943 A | 9/1981 | Hotta | |
| 4,323,066 A | 4/1982 | Bourdon | |
| 4,738,364 A | 4/1988 | Yeager | |
| 4,951,482 A * | 8/1990 | Gilbert | A01N 1/02 62/306 |
| 4,955,480 A * | 9/1990 | Sexton | B65D 81/18 206/438 |
| 5,317,883 A | 6/1994 | Newman | |
| 5,330,810 A | 7/1994 | Nishino | |
| 5,355,684 A * | 10/1994 | Guice | A01N 1/02 62/457.2 |
| 5,390,791 A | 2/1995 | Yeager | |
| 5,531,255 A | 7/1996 | Vacca | |
| 5,615,772 A | 4/1997 | Naganuma | |
| 5,976,400 A | 11/1999 | Muffett | |
| 6,104,611 A | 8/2000 | Glover | |
| 6,336,340 B1 | 1/2002 | Laby | |
| 6,584,797 B1 | 7/2003 | Smith | |
| 6,634,417 B1 | 10/2003 | Kolowich | |
| 6,968,888 B2 | 11/2005 | Kolowich | |
| 7,041,123 B2 | 5/2006 | Stapf | |
| 7,059,387 B2 | 6/2006 | Kolowich | |
| 7,294,374 B2 | 11/2007 | Romero | |
| 7,328,583 B2 | 2/2008 | Hillman | |
| 7,412,846 B2 | 8/2008 | Sekiya | |
| 7,836,722 B2 | 11/2010 | Magill | |
| 7,908,870 B2 | 3/2011 | Williams | |
| 7,934,537 B2 | 5/2011 | Kolowich | |
| 8,074,465 B2 * | 12/2011 | Heroux | A01N 1/02 62/371 |
| 8,096,975 B2 | 1/2012 | Lewis | |
| 8,205,468 B2 | 6/2012 | Hemminger | |
| 8,225,616 B2 | 7/2012 | Wilkinson | |
| 8,550,703 B2 | 10/2013 | Cutting | |
| 8,607,581 B2 | 12/2013 | Williams | |
| 9,151,531 B2 | 10/2015 | Wengreen | |
| 9,181,015 B2 | 11/2015 | Booska | |
| 9,707,156 B2 | 7/2017 | Wengreen | |
| 2003/0012701 A1 | 1/2003 | Sangha | |
| 2005/0016895 A1 | 1/2005 | Glenn | |
| 2005/0188714 A1 | 9/2005 | Wallace | |
| 2006/0191282 A1 | 8/2006 | Sekiya | |
| 2006/0271014 A1 | 11/2006 | Hynes | |
| 2007/0000484 A1 | 1/2007 | Magill | |
| 2007/0017533 A1 | 1/2007 | Wyrick | |
| 2007/0158325 A1 | 7/2007 | Cao | |
| 2007/0210090 A1 | 9/2007 | Sixt | |
| 2009/0078708 A1 | 3/2009 | Williams | |
| 2009/0230138 A1 | 9/2009 | Williams | |
| 2011/0155621 A1 | 6/2011 | Lindquist | |
| 2011/0207824 A1 | 8/2011 | Douleau | |
| 2012/0073312 A1 | 3/2012 | Cutting | |
| 2013/0025298 A1 | 1/2013 | Schryver | |
| 2013/0134347 A1 | 5/2013 | Edgar | |
| 2013/0221013 A1 | 8/2013 | Kolowich | |
| 2013/0255824 A1 | 10/2013 | Williams | |
| 2014/0259912 A1 | 9/2014 | Sutterlin | |
| 2014/0343493 A1 | 11/2014 | Wengreen | |
| 2015/0151893 A1 | 6/2015 | Wengreen | |
| 2016/0250101 A1 | 9/2016 | Wengreen | |
| 2016/0251140 A1 | 9/2016 | Wengreen | |
| 2016/0262979 A1 | 9/2016 | Wengreen | |
| 2016/0271015 A1 | 9/2016 | Wengreen | |
| 2016/0279029 A1 | 9/2016 | Wengreen | |

OTHER PUBLICATIONS

PureTemp: "About Entropy Solutions, Inc.," downloaded Feb. 5, 2015 from http://www.puretemp.com/stories/about-entropy-solutions-inc.

Fastcoexist.com Listing: "Passive Vaccine Storage Device," downloaded Aug. 15, 2013 from http://www.fastcoexist.com/1682578/this-bill-gates-backed-super-thermos-saves-lives-with-cold-vaccines.

Howstuffworks.com Article: "How Thermoses (Vacuum Flasks) Work," downloaded Jun. 14, 2013 from http://home.howstuffworks.com/thermos2.htm.

Wikipedia Article: "Epinephrine Autoinjector," downloaded Jun. 14, 2013 from http://en.wikipedia.org/wiki/Epinephrine_autoinjector.

Aliexpress.com Listing: "Retail Medicine Storage Product Mini EpiPen Fridge," downloaded Jun. 14, 2013 from http://www.aliexpress.com/item/Retail-medicine-storage-product-mini-epipen-fridge-maintains-the-inside-temperature-at-2-8-degreeC-CE/827311928.html.

Aliexpress.com Listing: "Pharmacy Product JYK-A Portable EpiPen Fridge," downloaded Jun. 14, 2013 from http://www.aliexpress.com/item/Pharmacy-product-JYK-A-Portable-epipen-fridge-AC-DC-li-battery-comes-with-16-5hrs-leading/723856846.html.

Amazon.com Listing: "Epinephrine-Mate Auto-Injector Carrying Case," downloaded Jun. 14, 2013 from http://www.amazon.com/EPInephrine-Mate-Auto-Injector-Carrying-Case/dp/B000VM9HGK.

Lindongroup.com Graphic: "Epinephrine-Mate Auto-Injector Carrying Case," downloaded Jun. 14, 2013 from http://www.lindongroup.com/uploads/images/Lindon%20Design/epinephrinemate%20package.jpg.

Omaxcare.com Listing: "LegBuddy," downloaded Jun. 14, 2013 from http://omaxcare.com/LegBuddy.html.

Amazon.com Listing: "AllerMates EpiPen & Allergy Medicine Carrying Case," downloaded Jun. 14, 2013 from http://www.amazon.com/AllerMates-Allergy-Medicine-Carrying-Squares/dp/B00CBLWMRA.

Esty.com Listing: "EpiPen Case Pouch," downloaded Jun. 14, 2013 from http://www.esty.com/listing/81915096/epi-pen-pouch-carrior-insulated.

Allergyapparel.com Listing: "AllerMates EpiPen Carrying Case," downloaded Jun. 17, 2014 from http://www.allergyapparel.com/AllerMates-EpiPen-Canying-Case-allermates-epicase-blu-pnk.html.

EpiPen.com: "EpiPen.com FAQ," downloaded Jun. 14, 2013 from http://www.epipen.com/professionals/faq.

Ball Article: "How Beverage Cans are Made," downloaded Apr. 21, 2016 from www.ball-europe.com/Production-process-of-beverage-cans.htm.

PureTemp Article: "PCM Products," includes Vesl products, downloaded Apr. 21, 2016 from www.puretemp.com/stories/products.

Vesl: "TubeVesl," downloaded Apr. 21, 2016 from www.veslpcm.com/tubevesl/.

Vesl: "MatVesl," downloaded Apr. 21, 2016 from www.veslpcm.com/matvesl/.

Allergyapparel.com Listing: "Kool Blanket," downloaded Jun. 3, 2016 from www.allergyapparel.com/kool-blanket.

Frioinsulincoolingcase.com Listing: "Frio Case," downloaded Jun. 3, 2016 from www.frioinsulincoolingcase.com/media/FRIO%20Brochure.pdf.

(56) References Cited

OTHER PUBLICATIONS

Veta Smart Case, downloaded Oct. 19, 2016 from https://www.aterica.com/how-it-works.
"AnAPPhylaxis" Case, downloaded Oct. 19, 2016 from http://www.adanmi.com/anapphylaxis.
FlexiFreeze Medicine CooleRx, downloaded Oct. 31, 2016 from https://www.amazon.com/FlexiFreeze-FF0MC03-0MCBK-Medicine-CooleRx/dp/B001P30362/ref=sr_1_4?ie=UTF8&qid=1477930020&sr=8-4&keywords=FlexiFreeze.

* cited by examiner 736 proximal retention member 736 proximal retention member 738 distal retention member 738 distal retention member 738b distal retention member 738b distal retention member 738b

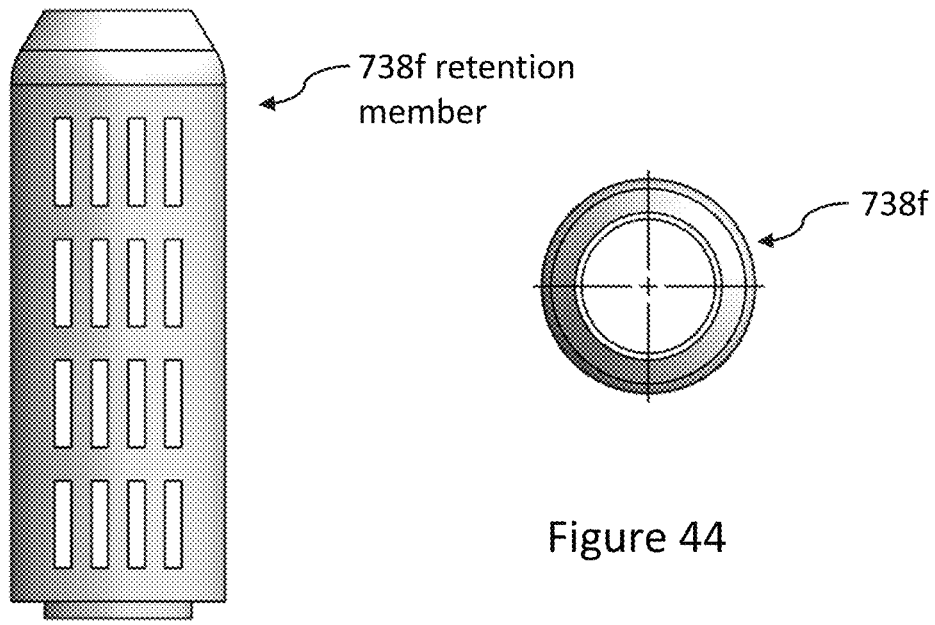
Figure 44
Figure 43
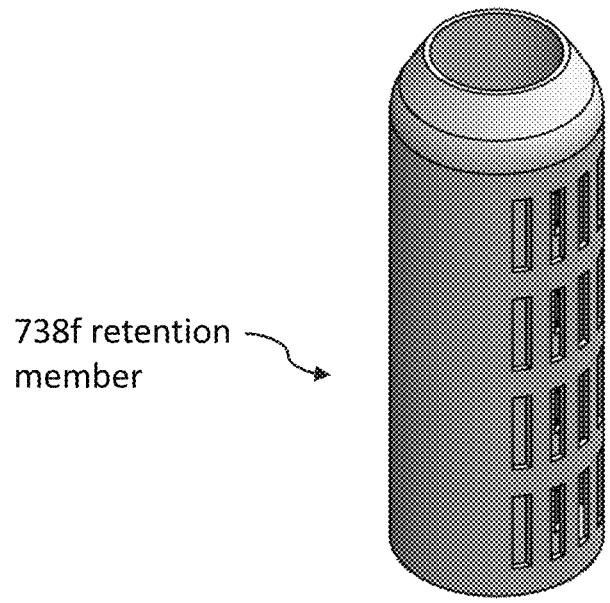
Figure 45

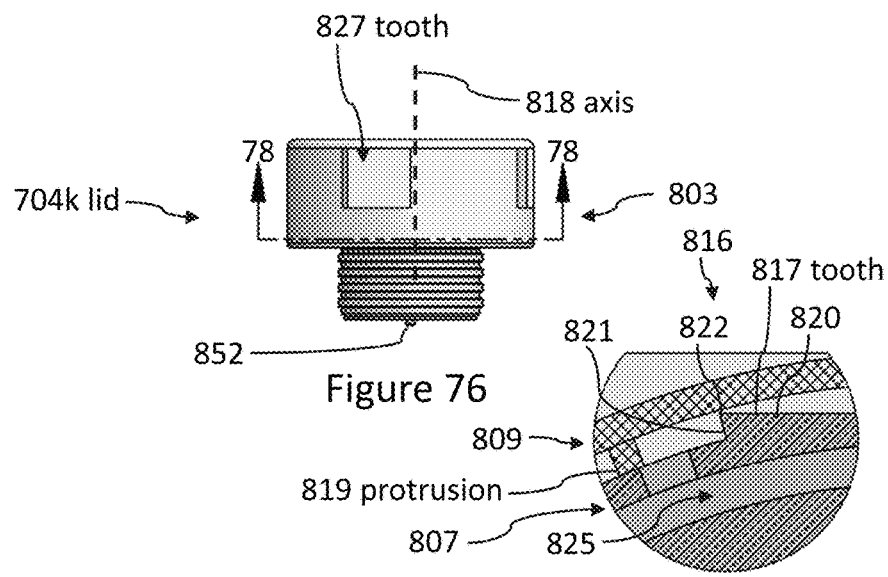
Figure 76
Figure 77
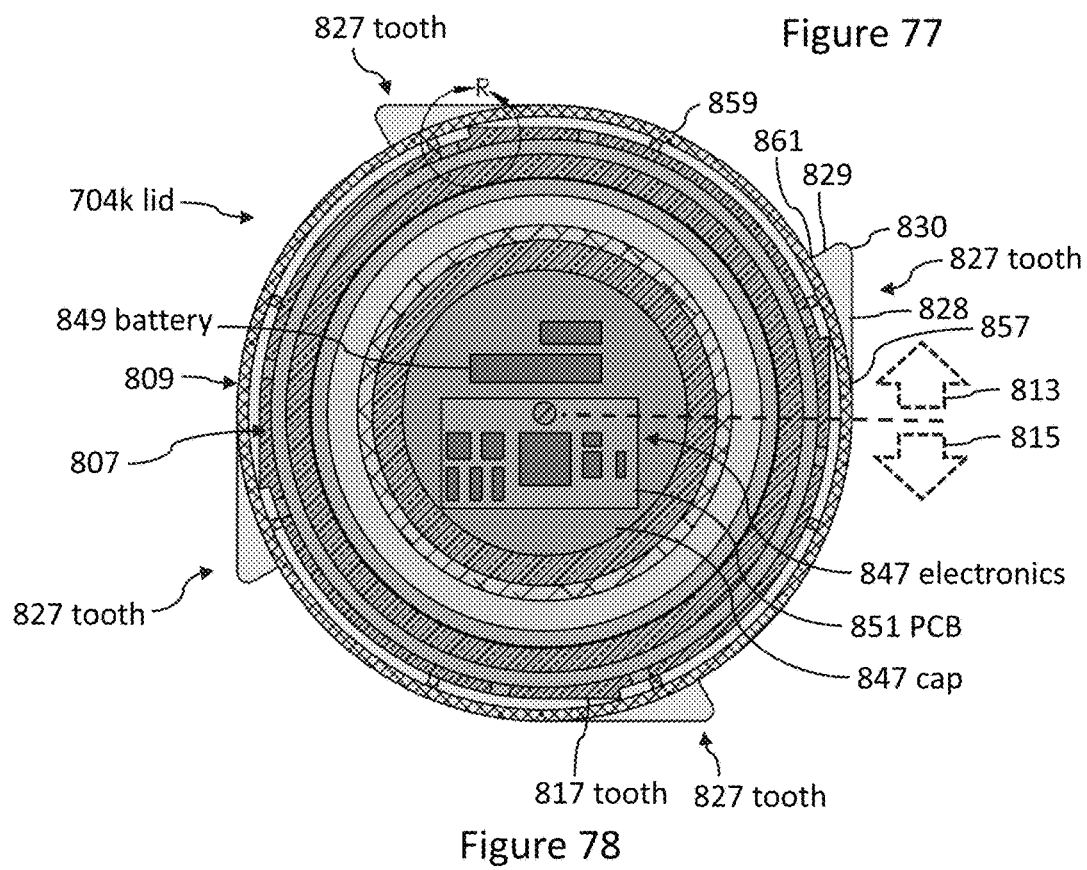
Figure 78

STORAGE SYSTEMS AND METHODS FOR MEDICINES

CROSS-REFERENCE TO RELATED APPLICATIONS

The entire contents of the following patent application are incorporated by reference herein: U.S. Provisional Patent Application No. 62/293,691; filed Feb. 10, 2016; and entitled STORAGE SYSTEMS AND METHODS FOR MEDICINES.

The entire contents of the following patent application are incorporated by reference herein: U.S. Nonprovisional patent application Ser. No. 14/849,884; filed Sep. 10, 2015; and entitled STORAGE SYSTEMS AND METHODS FOR MEDICINES.

The entire contents of the following patent application are incorporated by reference herein: U.S. Nonprovisional patent application Ser. No. 14/616,652; filed Feb. 6, 2015; and entitled STORAGE SYSTEMS AND METHODS FOR MEDICINES.

The entire contents of the following patent application are incorporated by reference herein: U.S. Nonprovisional patent application Ser. No. 13/896,211; filed May 16, 2013; and entitled STORAGE SYSTEMS AND STORAGE METHODS FOR INJECTABLE SUBSTANCES.

BACKGROUND

Field

Various embodiments disclosed herein relate to systems and methods to store medicines. Certain embodiments relate to maintaining medicines at a suitable temperature.

Description of Related Art

Users of medicines, such as epinephrine, adrenaline, and insulin, are faced with a difficult challenge. On one hand, physicians often advise patients to take their medicines with them wherever they go. Yet on the other hand, the temperature of many medicines typically should be maintained within a temperature range that is incompatible with outdoor temperatures. For example, a certain injectable substance might need to be stored within a temperature range of 65 degrees Fahrenheit to 85 degrees Fahrenheit. Outdoor temperatures are often colder than 65 degrees Fahrenheit or warmer than 85 degrees Fahrenheit. As a result, patients who need injectable substances sometimes must remain indoors, risk going outdoors without the safety of carrying the injectable substance, or risk reducing the efficacy of the injectable substance by carrying it into environments with temperatures outside of the recommended range.

Prior art solutions have included refrigerators set to particular temperatures to store medicines within a suitable range. (The suitable range can be the storage range recommended by the manufacturer of the medicine.) Refrigerators require substantial electrical power. Constantly having to plug a refrigerator into a power supply, changing batteries, or recharging batteries is inconvenient. In addition, users sometimes forget to provide adequate power, which can result in harming the medicine, and thereby, creating a health risk to the user. Thus, there is a need for systems and methods to store injectable substances within a suitable temperature range while requiring little or no electrical power.

Prior art solutions have also included bulky insulation systems that are inconvenient for patients to carry outside. Due to this inconvenience, many patients do not carry vital medicines when they go outside. As a result, many patients have suffered medical emergencies and some patients have died. Thus, there is a need for systems and methods that are convenient enough for patients to carry their medicines outdoors.

SUMMARY

In some embodiments, devices to store medicines can include a chamber configured to store a medicine, a thermal bank, and an insulated cover. The thermal bank can be located inside the insulated cover. At least a portion of the chamber can be located inside the thermal bank. The thermal bank can include phase change materials. Storage devices can also include innovative structures that dramatically reduce the volume and weight of the storage devices while still shielding medicines from extreme outdoor environments.

In some embodiments, devices to store injectable substances can include an outer case and a vacuum flask located inside the outer case. The devices can include a thermal bank located inside the vacuum flask. The thermal bank can include a void that extends from an inner portion of the thermal bank to an outer portion of the thermal bank. An injectable substance can be located inside the void. The devices can include a removable lid configured to allow a user to remove the injectable substance from the storage system. In some embodiments, a user unthreads or rotates the lid to remove the lid. In several embodiments, insulated containers use foam insulation, materials that capture small air pockets, or other suitable insulation rather than a vacuum flask (e.g., a Thermos).

Several embodiments include methods of storing injectable substances, inhalers, pharmaceuticals, or drugs. Some method embodiments comprise obtaining an outer case and a lid. Several methods include placing a vacuum flask inside the outer case and placing a thermal bank inside the vacuum flask. Some methods include placing an injectable substance inside the vacuum flask and closing the lid such that the outer case and the lid completely surround the injectable substance.

Some embodiments include a storage system comprising a chamber configured to store an injection device; a thermal bank; and/or an insulated cover. The thermal bank can have a heat capacity of at least 1,200 J/K. The thermal bank can be located inside the insulated cover. At least a portion of the chamber can be located inside the thermal bank. The injection device can be located inside the chamber. The injection device can comprise a syringe and a pharmaceutical agent located inside the syringe. The pharmaceutical agent can comprise epinephrine.

In some embodiments, the thermal bank comprises a hole that extends to an outer surface of the thermal bank and at least a portion of the chamber is located in the hole. The chamber can have a volume, and at least 60% of the volume of the chamber can be located inside the thermal bank.

In several embodiments, the storage system has a central axis, and the chamber is located approximately along a portion of the central axis. A portion of the thermal bank can be located radially outward relative to the chamber. A portion of the insulated cover can be located radially outward relative to the thermal bank. The thermal bank can be removably coupled to the insulated cover. The thermal bank can be rigidly coupled to the insulated cover. The thermal bank can comprise a container with solid outer walls. The container can be at least partially filled with a liquid having a melting temperature between 40 degrees Fahrenheit and 100 degrees Fahrenheit.

In some embodiments, the storage system includes an outer case; a vacuum flask located inside the outer case; and/or a thermal bank located inside the vacuum flask. The thermal bank can include a heat capacity of at least 400 J/K. The thermal bank can also include a void that extends from an inner portion of the thermal bank to an outer portion of the thermal bank. The void can be at least 1 centimeter wide and at least 6 centimeters long. An injectable substance can be located inside the void. A removable lid can be configured to allow a user to remove the injectable substance from the storage system. The storage system can have a volumetric center. The volumetric center can be located inside the void. The heat capacity of the thermal bank can be at least 2,000 J/K and/or less than 12,000 J/K.

Several embodiments of storing a medicinal injectable substance include obtaining an outer case and a lid; obtaining a vacuum flask located inside the outer case; obtaining a thermal bank with a heat capacity of at least 400 J/K, wherein the thermal bank can be located inside the vacuum flask; placing an injection device inside the vacuum flask, wherein the injection device is at least partially filled with the medicinal injectable substance; and/or coupling the lid to the outer case such that the outer case and the lid surround the injection device. The injection device can include a syringe at least partially filled with epinephrine.

Some embodiments include placing the injection device inside at least a portion of the thermal bank. Embodiments can include forming the outer case around at least a portion of the vacuum flask. Several embodiments include maintaining the injectable substance within a temperature range of at least 50 degrees Fahrenheit and less than 90 degrees Fahrenheit. Inside environments can have a "room temperature" (e.g., a temperature within a typical range for a temperature-controlled home in the United States). Some embodiments include isolating the injectable substance from fluids located outside of the injection device.

Several embodiments include placing the thermal bank in a first environment, wherein the first environment has a temperature greater than 65 degrees Fahrenheit and less than 85 degrees Fahrenheit; removing the thermal bank from the first environment and transporting the thermal bank towards a second environment while the thermal bank has a temperature greater than 65 degrees Fahrenheit and less than 85 degrees Fahrenheit, wherein the second environment has a temperature less than 65 degrees Fahrenheit or greater than 85 degrees Fahrenheit; and/or moving the thermal bank from the second environment to a third environment before the temperature of the thermal bank falls below 65 degrees Fahrenheit or rises above 85 degrees Fahrenheit, wherein the third environment has a temperature greater than 65 degrees Fahrenheit and less than 85 degrees Fahrenheit. The first environment can be indoors. The second environment can be outdoors. The third environment can be indoors (e.g., at a room temperature). Some embodiments do not comprise using electricity to alter the temperature of the thermal bank while the thermal bank is located in the second environment and while the heat capacity of the thermal bank is at least 800 J/K. Embodiments can use electricity to measure temperatures even if they do not use electricity to alter the temperature.

In several embodiments, storage systems include an insulated container comprising a base and an opening configurable to enable removing a medicine from inside the insulated container; a first chamber located inside the insulated container, wherein the first chamber is configured to hold the medicine; a first phase change material located inside the insulated container; and/or a second phase change material located inside the insulated container.

In some embodiments, the first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. The first melting temperature can be at least four degrees Fahrenheit less than the second melting temperature. For example, 74 degrees Fahrenheit can be approximately equal to a typical room temperature (although room temperatures commonly range from 67 degrees Fahrenheit to 80 degrees Fahrenheit in rooms having temperature controlled environments enabled by heating and/or air conditioning).

Using a "temperature dividing line" of 74 degrees Fahrenheit helps enable some embodiments to avoid inappropriately triggering melting and/or freezing while the storage system is located in a temperature controlled room. Imagine if the second phase change material had a melting temperature of less than 74 degrees. As a result, the second phase change material could completely melt before a person even moved the storage system from a room temperature into a hot outdoor environment that is warmer than a maximum recommended storage temperature of the medicine. In this case, the phase change of the second phase change material would not help reduce the rate of temperature rise inside the first chamber in response to heat transfer caused by the hot environment. Similarly, this "temperature dividing line" helps ensure the first phase change material will have a sufficiently low melting temperature such that the first phase change material should not solidify before the storage system is moved from a room temperature to an environment that is colder than a minimum recommended storage temperature.

In some embodiments, the first phase change material can have a first melting temperature greater than 63 degrees Fahrenheit and less than 74 degrees Fahrenheit. The second phase change material can have a second melting temperature greater than 74 degrees Fahrenheit and less than 83 degrees Fahrenheit. These melting temperatures can be particularly effective to create a system that quickly responds (e.g., by changing phases) to temperature changes caused by leaving an indoor environment and entering an outdoor environment. Meridian Medical Technologies, Inc. makes a medicine called an EpiPen. EpiPens can have a minimum recommended storage temperature of 68 degrees Fahrenheit and a maximum recommended storage temperature of 77 degrees Fahrenheit. Other medicines often have different minimum and maximum recommended storage temperatures.

In some embodiments, the storage system is configured to cause the first phase change material to solidify when a first temperature of the first chamber falls below the first melting temperature, and/or the storage system is configured to cause the second phase change material to melt when the first temperature of the first chamber rises above the second melting temperature. As a result, the storage system can be configured to temporarily protect the medicine from a first environment that is colder than a safe minimum storage temperature and/or from a second environment that is hotter than a safe maximum storage temperature. Manufacturers of medicines can recommend minimum storage temperatures and/or maximum storage temperatures for medicines.

In several embodiments, the first phase change material has a first latent heat of at least 40 kJ/kg, and/or the second phase change material has a second latent heat of at least 40 kJ/kg. (The latent heats described herein are latent heats of fusion.) In some embodiments, the first phase change material has a first latent heat of at least 110 kJ/kg, and/or the second phase change material has a second latent heat of at least 110 kJ/kg. In several embodiments, the first phase change material has a first latent heat of at least 180 kJ/kg, and/or the second phase change material has a second latent heat of at least 180 kJ/kg. These latent heat properties can dramatically reduce the necessary weight of the phase change materials, which can enable dramatically reducing the overall volume of the storage system.

In some embodiments, a storage system comprises a second chamber having the first phase change material, and/or the insulated container comprises a third chamber having the second phase change material. The second chamber and the third chamber can be located inside the insulated container. The opening can be coupled to the first chamber such that the opening is configurable to provide access to the first chamber to enable removing the medicine from the insulated container.

In some embodiments, the insulated container is a flexible bag with a foil coating to reduce the rate of heat transfer in and out of the bag. The bag can have a fabric exterior. The chambers can be pliable bags. In some embodiments, the insulated container is a rigid container with foam insulation. In several embodiments, the insulated container is a vacuum flask comprising a chamber with a pressure below atmospheric pressure to reduce heat transfer through the vacuum flask.

In several embodiments, a phase change system comprises the first phase change material and the second phase change material such that the phase change system is configured to change phases at multiple temperatures greater than 40 degrees Fahrenheit and less than 100 degrees Fahrenheit. For example, the first phase change material can solidify at 68 degrees Fahrenheit, and the second phase change material can melt at 82 degrees Fahrenheit. The phase change system can include many chambers. Some embodiments include at least four phase change materials and at least ten chambers with walls separating the chambers. The phase change system can be located inside the insulated container. At least a majority of the first chamber can be located between portions of the phase change system. For example, a first phase change material can be located on one side of the first chamber and a second phase change material can be located on an opposite side of the first chamber such that the phase change system "sandwiches" the first chamber.

In some embodiments, at least the majority of the first chamber is located between a first compliant wall and a second compliant wall. The first compliant wall can separate at least the majority of the first chamber from a first side of the phase change system. The second compliant wall can separate at least the majority of the first chamber from a second side of the phase change system. The compliant walls can make the first chamber expandable.

In several embodiments, the opening that leads into the first chamber comprises a length from a first end of the opening to a second end of the opening. The first chamber can comprise a minimum thickness between the first compliant wall and the second compliant wall in a location configured to hold the medicine. Prior to inserting the medicine into the first chamber, the length can be at least five times larger than the minimum thickness. The first chamber can be configured to expand in response to inserting the medicine into the first chamber such that the first chamber is configured to hold the medicine having a thickness that is greater than the minimum thickness of the first chamber. These embodiments can enable a collapsible storage system that can more easily fit in a pocket, purse, or bag when not in use. For example, the outer walls of the storage system can contract inwards as the thickness of the first chamber is reduced.

In some embodiments, the storage system comprises a second chamber that holds the first phase change material. The second chamber can be located inside the insulated container. The opening can be coupled to the first chamber such that the opening is configurable to provide access to the first chamber to enable removing the medicine from the insulated container. When the opening is unsealed, a person can reach into the opening to grab the medicine in the first chamber.

In several embodiments, the first chamber has a longest dimension, and the second chamber has a longest dimension. The first chamber and the second chamber can be oriented such that the longest dimension of the first chamber and the longest dimension of the second chamber both point towards the same exterior side of the storage system (e.g., towards one end of the storage system or towards an opening of the storage system). When the longest dimension of the first chamber and the longest dimension of the second chamber both point towards the same exterior side of the storage system, a portion of the first chamber and at least a portion of the second chamber can run approximately alongside each other (e.g., even though a wall separates the first chamber from the second chamber). The first chamber and the second chamber can be oriented such that they extend distally in a first direction away from the opening. The insulated container can be a vacuum flask and/or a foam container.

In several embodiments, the insulated container comprises a central axis, and the first chamber extends distally away from the opening such that at least a majority of the central axis is located inside the first chamber. The second chamber can be located outside of the first chamber and radially outward from the central axis. The storage system can also comprise a third chamber having the second phase change material. The second chamber can be located inside the insulated container. The third chamber can be located outside of the first chamber and radially outward from the central axis. The insulated container can be a vacuum flask or a container with walls insulated by foam.

In several embodiments, the storage system includes a phase change system comprising the first phase change material and the second phase change material such that the phase change system is configured to change phases at multiple temperatures greater than 40 degrees Fahrenheit and less than 100 degrees Fahrenheit. The phase change system can be located inside the insulated container.

In some embodiments, the first chamber is located between a first wall and a second wall. In several embodiments, at least a majority of the first chamber is located between a first wall and a second wall. The first wall can separate the first chamber from a first side of the phase change system. The second wall separates the first chamber from a second side of the phase change system. The first and second walls can be rigid or compliant. Rigid walls can be rigid plastic or metal. Compliant walls can be made from plastic configured to bend without breaking to conform to many different shapes.

In several embodiments, a third wall passes through the central axis to separate the second chamber from the third chamber. The third wall can separate a distal portion of the phase change system from a proximal portion of the phase change system. The third wall can be perpendicular to the central axis to separate the distal portion from the proximal portion. The third wall can also be perpendicular to the central axis to separate a left half of the phase change system from a right half of the phase change system.

Some embodiments include a first wall that separates the first chamber having the medicine from the second chamber having the first phase change material. A second wall can separate the first chamber having the medicine from the third chamber having the second phase change material. The first chamber, the second chamber, and the third chamber can extend distally parallel relative to each other. The first chamber, the second chamber, and the third chamber can be oriented such that they are located next to each other while being separated by walls.

In several embodiments, the insulated container comprises a vacuum flask having a cylindrical interior wall, which forms a cylindrical interior volume that is divided into chambers by walls that can be rigid or pliable. In some embodiments, phase change materials are located in compliant bags, the walls of which separate chambers. The medicine can be located inside the first chamber.

In several embodiments, the insulated container comprises a central axis, and the phase change system can be located in a central portion of the insulated container such that at least a majority of the central axis is located inside the phase change system (e.g., while a first medicine is located radially outward from at least a portion of the phase change system and a second medicine is located radially outward from at least the portion of the phase change system). A first wall can separate the first chamber having the medicine from the phase change system. A second wall can separate the phase change system from a fourth chamber. The storage system can also include a removable lid (e.g., a "screw-on" lid) coupled to the base such that removing the lid facilitates accessing both the first chamber and the fourth chamber such that an injection device can be removed from the fourth chamber.

In some embodiments, a chamber configured to hold medicine is configured to hold two medicines (e.g., two EpiPens).

In some embodiments, the first chamber can be located radially outward from the central axis on a first side of the phase change system. The fourth chamber can be located radially outward from the central axis on a second side of the phase change system. A third wall can pass through the central axis to separate the second chamber from the third chamber.

In several embodiments, storage systems include a phase change system comprising the first phase change material and the second phase change material such that the phase change system is configured to change phases at multiple temperatures greater than 40 degrees Fahrenheit and less than 100 degrees Fahrenheit. Some embodiments of phase change systems change phases at multiple temperatures greater than 34 degrees Fahrenheit and/or less than 110 degrees Fahrenheit; and/or change phases at multiple temperatures greater than 62 degrees Fahrenheit and/or less than 82 degrees Fahrenheit. The insulated container can comprise a central axis, and the first chamber can extend distally away from the opening such that at least a portion of the central axis is located inside the first chamber. The phase change system can be located inside the insulated container and can be located distally relative to the first chamber. The phase change system can comprise a second chamber having the first phase change material.

In some embodiments, the phase change system can comprise a third chamber. The second phase change material can be located inside the third chamber. The phase change system can comprise a wall located distally relative to the first chamber. The wall can separate the second chamber from the third chamber. The insulated container can comprise a vacuum flask having a cylindrical interior wall. The medicine can be located inside the first chamber.

In several embodiments, the storage system comprises a second chamber having the first phase change material. The second chamber can be located inside the insulated container. The opening can be coupled to the first chamber such that the opening is configurable to provide access to the first chamber to enable removing the medicine from the insulated container. Closing the opening can include using a lid or closing mechanism to shut the opening (in an air-tight or non-air-tight manner).

In some embodiments, the insulated container comprises a central axis, and the first chamber extends from the opening to a distal half of the insulated container. The storage system can also comprise a second chamber having the first phase change material and a third chamber having the second phase change material. The second chamber and the third chamber can be located outside of the first chamber and radially outward relative to the central axis.

In several embodiments, a first wall separates the first chamber from the second chamber, and a second wall separates the second chamber from the third chamber. The second chamber can be located distally or proximally relative to the third chamber while being located outside of the first chamber and radially outward relative to the central axis.

All of the apparatus and system embodiments described herein can be used with any of the methods described herein. Elements from one embodiment can be combined with elements of other embodiments.

Some embodiments include using a storage system having a first chamber configured to hold a medicine, a second chamber having a first phase change material, and a third chamber having a second phase change material. The first phase change material can have a first melting temperature that is greater than 40 degrees Fahrenheit and less than 74 degrees Fahrenheit. The second phase change material can have a second melting temperature that is greater than 74 degrees Fahrenheit and less than 100 degrees Fahrenheit. The first melting temperature can be at least four degrees Fahrenheit less than the second melting temperature (e.g., to ensure there is an adequate difference between the melting temperatures to reduce the likelihood of inappropriate melting and solidifying).

A manufacturer of the medicine can recommend a minimum storage temperature and a maximum storage temperature for the medicine. For example, the medicine can include instructions for use that state to store the medicine at 68 degrees Fahrenheit to 77 degrees Fahrenheit (as can be the case with EpiPens made by Meridian Medical Technologies, Inc., a Pfizer Company).

Some embodiments include obtaining the storage system. The storage system can have a first temperature. Embodiments can include placing the storage system inside a building having a first room temperature; leaving the storage system inside the building until the first phase change material is melted and the second phase change material is solidified; placing the medicine inside the first chamber and then closing (e.g., covering an opening) the first chamber from an external environment located outside of the storage system; moving the storage system to a cold environment that is colder than the first room temperature, colder than the first melting temperature, and/or colder than the minimum storage temperature of the medicine, then returning the storage system to a second room temperature before the first phase change material is completely solidified; and/or moving the storage system to a hot environment that is warmer than the first room temperature, warmer than the second melting temperature, and/or warmer than the maximum storage temperature of the medicine. Then, embodiments can include returning the storage system to a third room temperature before the second phase change material is completely melted.

As used herein, "room temperature" is used in a very broad sense, and can include a temperature inside a building and/or a temperature in a temperature-controlled building. The first, second, and third room temperatures can be equal to each other or different from each other. The first, second, and third room temperatures can be in the same building and/or room. The first, second, and third room temperatures can be in different buildings and/or rooms.

After returning the storage system to the second room temperature, some methods include exposing the storage system to the second room temperature until the first phase change material is melted before moving the storage system to a first extreme environment that is colder than the minimum recommended storage temperature. After returning the storage system to the third room temperature, some methods include exposing the storage system to the third room temperature until the second phase change material is solidified before moving the storage system to a second extreme environment that is hotter than the minimum recommended storage temperature.

Several embodiments include continuing to cover (e.g., covering an opening) the first chamber from the external environment from a first time the storage system leaves a fourth room temperature to move to the cold environment; while the storage system is located in the cold environment; and/or until returning the storage system to an environment having a fifth room temperature. Embodiments can also include opening the first chamber to the fifth room temperature in response to returning to the fifth room temperature. Several embodiments include continuing to open the first chamber to the fifth room temperature until the first phase change material is melted and the second phase change material is solidified.

As used herein, "cover" and "covering" are used in a very broad sense to mean covering an opening (e.g., by closing the opening or placing a lid in the opening). "Cover" and "covering" can include "seal" and "sealing," but in some embodiments, "cover" and "covering" might not form an air-tight seal. For example, a lid of a cooler can cover the opening to the cooler, but the lid does not necessarily form an airtight seal.

Several embodiments include obtaining the storage system; placing the storage system in a first inside environment; leaving the storage system in the first inside environment until the first phase change material is melted and the second phase change material is solidified; placing the medicine inside the first chamber and then closing the first chamber from an external environment (e.g., covering an opening leading to the first chamber), wherein the external environment is external relative to the storage system; moving the storage system to a cold outdoor environment that is colder than the first inside environment, colder than the first melting temperature, and/or colder than the minimum storage temperature of the medicine; and then returning the storage system to a second inside environment before the first phase change material is completely solidified. Some embodiments include moving the storage system to a hot outdoor environment that is warmer than the second inside environment, warmer than the second melting temperature, and/or warmer than the maximum storage temperature of the medicine, and then returning the storage system to a third inside environment before the second phase change material is completely melted.

As used herein, an environment is a cold outdoor environment if it is colder than the first inside environment. As used herein, an environment is a hot outdoor environment if it is hotter than the second inside environment. For example, a cold outdoor environment can be colder than a room temperature and a hot outdoor environment can be hotter than the room temperature.

In several embodiments, the medicine comprises a minimum storage temperature and a maximum storage temperature configured to avoid temperature-induced damage to the medicine. (The manufacturer of the medicine can recommend the minimum and maximum storage temperatures.) The first melting temperature can be equal to or within 7 degrees Fahrenheit greater than the minimum storage temperature. The second melting temperature can be equal to or within 7 degrees Fahrenheit less than the maximum storage temperature to reduce a temperature difference between the first chamber and an outside environment during a phase change of the first phase change material or the second phase change material.

In some embodiments, the first phase change material has a first melting temperature between 33 degrees Fahrenheit and 72 degrees Fahrenheit, and the second phase change material has a second melting temperature between 78 degrees Fahrenheit and 110 degrees Fahrenheit. The first chamber can be located at least partially between a second chamber and a third chamber. A first wall can separate the first chamber from the second chamber. A second wall can separate the first chamber from the third chamber. A first pliable bag can hold the first phase change material inside the second chamber. A second pliable bag can hold the second phase change material inside the third chamber. In some embodiments, the first pliable bag is the second chamber. In several embodiments, the first pliable bag is located within a chamber with rigid walls.

In several embodiments, the first chamber comprises a first central axis, the second chamber comprises a second central axis, and the third chamber comprises a third central axis. The first central axis, the second central axis, and/or the third central axis can be oriented parallel relative to each other.

In some embodiments, the first chamber can be located at least partially between a second chamber and a third chamber. The second chamber can be located radially outward from the first central axis on a first side of the first chamber. The third chamber can be located radially outward from the central axis on a second side of the first chamber.

In several embodiments, the first chamber, the second chamber, and the third chamber are located inside a cylindrical void of the insulated container. The cylindrical void can be an interior portion of a vacuum flask with a screw-on lid.

In some embodiments, a first wall separates the first chamber from the second chamber; a second wall separates the first chamber from the third chamber; a first pliable bag holds the first phase change material inside the second chamber; and/or a second pliable bag holds the second phase change material inside the third chamber. In several embodiments, the pliable bag forms a pliable chamber.

In several embodiments, a storage system comprises an insulated container having an opening; a lid configured to cover the opening; a phase change system located inside the insulated container; and a tube located inside the insulated container such that the tube is in fluid communication with the opening (to enable inserting a medicine through the opening and into the tube).

Many different types of insulated containers can be used. The insulated container can be a vacuum flask having stainless steel walls and a vacuum chamber located between the stainless steel walls. The insulated container can be a rigid shell surrounded by foam insulation. The insulated container can be a compliant bag made from fabric and insulated with any suitable insulation material.

In some embodiments, the phase change system comprises a first flexible bag having a first phase change material and a second flexible bag having a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

In some embodiments, the phase change system is configured to protect the medicine from a first external temperature less than a minimum recommended storage temperature and from a second external temperature greater than a maximum recommended storage temperature by utilizing phase changes to regulate a temperature of the medicine.

The medicine can be any type of medicine. In some embodiments, the medicine is an injection device having epinephrine. The injection device can be located in the tube.

In several embodiments, the first and second flexible bags are located inside the insulated container and are located outside the tube such that the first and second flexible bags are located between an inner wall of the insulated container and an outer wall of the tube.

In some embodiments, the first and second flexible bags are mechanically coupled to each other but fluidly isolate the first phase change material from the second phase change material. The first and second flexible bags can be made from one piece of film that has multiple chambers. Each chamber can hold a different type of phase change material. In some embodiments, twelve chambers hold a first phase change material and ten chambers hold a second phase change material. The flexible bags can be made from multiple layers of film. The separate chambers can be made by sealing portions of the film together.

In several embodiments, the outer wall of the tube comprises a first ventilation channel configured to enable airflow between an area inside the tube and the phase change system. The outer wall of the tube can comprise a second ventilation channel located on an opposite side of the tube relative to the first ventilation channel. (The insulated container can be insulated by a vacuum chamber.) The tube can include many ventilation channels that are oriented radially outward and have diverse shapes (e.g., round, square, rectangle). The ventilation channels can be configured to facilitate heat transfer between the medicine and the phase change system.

In some embodiments, the first flexible bag comprises at least two fluidly isolated chambers having the first phase change material. The second flexible bag can comprise at least two fluidly isolated chambers having the second phase change material. The first flexible bag can be wrapped at least partially around the tube. The second flexible bag can be wrapped at least partially around the tube.

In several embodiments, the first flexible bag is wrapped at least partially around the second flexible bag. In some embodiments, the second flexible bag is wrapped at least partially around the first flexible bag.

In several embodiments, the insulated container is insulated by a vacuum chamber, the phase change system is wrapped around the tube, the insulated container comprises a first central axis, the tube comprises a second central axis that is within 15 degrees of being aligned with the first central axis, and/or the tube extends from an upper half of the insulated container to a lower half of the insulated container. As used herein, "extends" means to continue in a specified direction or over a specified distance, but unless stated otherwise, typically does not mean to become longer.

In some embodiments, the tube is held inside the insulated container. At least one flex arm can be configured to hold the tube inside the insulated container. The flex arms can protrude farther radially outward than a narrowest section of an interior of the insulated container such that the flex arms are configured to flex radially inward in response to inserting the tube into the insulated container. The flex arms can be configured to contact a narrowing section of the interior to hold the tube inside the insulated container.

In several embodiments, the flex arm comprises a cantilever beam oriented within 80 degrees of a direction oriented (1) along a central axis of the tube and (2) towards the opening such that pulling the tube towards the opening increases a resistance of the flex arm to the pulling. This "engaging" structure can help prevent inadvertent removal of the tube from the insulated container. The tube and the flex arms can be molded plastic.

In some embodiments, the tube comprises at least one flex arm having a cantilever beam and a portion to engage an interior of the insulated container to hold the tube inside the insulated container. The portion can be oriented towards a narrowing portion of an interior of the insulated container. For example, the interior can be the widest in a region that holds the phase change system. The interior can be narrower in the opening than in the region that holds the phase change system. A narrowing portion is typically necessary to transition from the wider portion to the narrow portion of the interior. Engaging this narrowing portion can be particularly helpful in preventing the tube from falling out of the insulated container.

In some embodiments, the tube is coupled to a bracket that holds the tube inside the insulated container. Bracket embodiments can have diverse shapes and sizes.

In several embodiments, a maximum width of the opening is measured from a central axis of the insulated container in a direction perpendicular to the central axis. The tube can be coupled to a bracket having an outermost edge located farther from the central axis than the maximum width such that the bracket holds the tube inside the insulated container. In other words, the outermost edge can stick out so far that it cannot fit through the opening. (The bracket can flex to enable inserting the bracket into the insulated container.)

In several embodiments, a spring facilitates removing the medicine from the insulated container (e.g., by pushing the medicine towards the opening of the insulated container to help a user grasp a portion of the medicine).

In some embodiments, the spring is located in the insulated container. The spring can be configured to push the medicine towards the opening. A platform can be located inside the tube such that the spring pushes the platform towards the opening to push the medicine at least partially out of the opening so a user can pull the medicine out of the storage system.

In several embodiments, systems include a rotational release mechanism to guard against overtightening resulting in difficulty removing the lid of the storage system. The insulated container and/or the lid can comprise a rotational release mechanism configured such that the lid is rotatable relative to the insulated container in a first rotational direction that tightens the lid to the insulated container and in a second rotational direction that loosens the lid from the insulated container. The lid can comprise a first portion and a second portion. The first portion can comprise threads that couple the lid to the insulated container.

In some embodiments, the second portion of the lid is configured to rotate in the first rotational direction relative to the first portion of the lid in response to a first applied torque that exceeds a release threshold. The second portion of the lid can be configured to resist rotation in the second rotational direction relative to the first portion in a presence of a second applied torque that is at least thirty percent larger than a magnitude of the release threshold.

In several embodiments, the rotational release mechanism comprises an interface between the first portion and the second portion. The interface can have teeth slanted such that rotating the second portion relative to the first portion of the lid in the first rotational direction requires a lower torque than rotating the second portion relative to the first portion of the lid in the second rotational direction.

In several embodiments, a storage system comprises an insulated container having an opening; a lid configured to cover the opening; a phase change system located inside the insulated container; and a tube located inside the insulated container such that the tube is in fluid communication with the opening (to enable inserting a medicine through the opening and into the tube). The phase change system can comprise a first bag having a first phase change material. The first phase change material can have a first melting temperature greater than 40 degrees Fahrenheit and less than 74 degrees Fahrenheit. The insulated container can be a vacuum flask such that the insulated container is insulated by a vacuum chamber. The first bag can be located inside the insulated container and outside the tube such that the first bag is located between an inner wall of the insulated container and an outer wall of the tube. The tube can extend from an upper half of the insulated container to a lower half of the insulated container such that the storage system is configured to enable a user to remove the lid, insert the medicine through the opening and into the tube, replace the lid, and protect the medicine from temperatures below 40 degrees Fahrenheit.

In several embodiments, a storage system comprises an insulated container having an opening; a lid configured to cover the opening; a phase change system located inside the insulated container; and a tube located inside the insulated container such that the tube is in fluid communication with the opening (to enable inserting a medicine through the opening and into the tube). The phase change system can comprise a first bag having a first phase change material. The first phase change material can have a first melting temperature greater than 74 degrees Fahrenheit and less than 100 degrees Fahrenheit. The insulated container can be insulated by a vacuum chamber. The first bag can be located inside the insulated container and outside the tube such that the first bag is located between an inner wall of the insulated container and an outer wall of the tube. The tube can extend from an upper half of the insulated container to a lower half of the insulated container such that the storage system is configured to enable a user to remove the lid, insert the medicine through the opening and into the tube, replace the lid, and protect the medicine from temperatures above 100 degrees Fahrenheit.

In some embodiments, a storage system comprises an insulated container having an opening; a lid configured to cover the opening; a phase change system located inside the insulated container; and a tube located inside the insulated container such that the tube is in fluid communication with the opening (to enable inserting a medicine through the opening and into the tube). The phase change system can comprise a first phase change material and a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. The insulated container can be a vacuum flask.

In several embodiments, at least a portion of the phase change system is located between an inner wall of the insulated container and an outer wall of the tube such that the storage system is configured to enable a user to remove the lid, insert the medicine through the opening and into the tube, and replace the lid.

In some embodiments, an interior of the insulated container comprises a first cylindrical section and a second cylindrical section that is closer to the opening than the first cylindrical section. The second cylindrical section can have a second diameter that is smaller than a first diameter of the first cylindrical section. The first cylindrical section can have a first length measured along a central axis of the insulated container. The second cylindrical section can have a second length measured along the central axis of the insulated container. The first length can be at least twice as long as the second length.

In several embodiments, the tube comprises a third cylindrical section having a third diameter and a third length. The third length is measured along a central axis of the tube. The tube can comprise a fourth cylindrical section having a fourth diameter and a fourth length. The fourth length is measured along the central axis of the tube. The fourth cylindrical section can couple the third cylindrical section to the opening of the insulated container. The fourth diameter can be larger than the third diameter. The third length can be at least twice as long as the fourth length.

In some embodiments, threads of the storage system couple the insulated container to the lid. At least one of the second cylindrical section and a portion of the insulated container located radially outward from the second cylindrical section can comprise threads configured to couple the lid to the insulated container. A section can be cylindrical even if it has threads.

In several embodiments, seals are configured to limit or eliminate fluid communication between an environment outside the storage system and an interior of the storage system. The lid can comprise a distal compression seal, a proximal compression seal, and at least one axial seal located between the distal compression seal and the proximal compression seal. Seals can be wiper seals, o-rings, or any other suitable type of seal. Seals can be made from silicone or any other suitable material.

In some embodiments, a medicine storage system comprises an insulated container having an opening; a first lid configured to cover the opening; a phase change system located inside the insulated container; a medicine storage area located inside the insulated container; and a first retention member located inside the insulated container and configured to prevent the phase change system from blocking access to the medicine storage area. The storage system can be configured to provide access for inserting a medicine through the opening and into the medicine storage area.

In several embodiments, the phase change system comprises a first tube having a first phase change material and a second tube having a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

In some embodiments, the insulated container comprises a proximal portion and a distal portion. The distal portion is located farther from the opening than the proximal portion. The first retention member can be located inside the insulated container in the distal portion. The first retention member can comprise a protrusion between the first tube and the second tube.

In several embodiments, the first retention member comprises a cavity, the insulated container comprises a central axis that passes through the cavity, the cavity comprises a portion of the medicine storage area, the protrusion of the first retention member is oriented radially outward relative to the central axis, the first tube is oriented within 30 degrees of parallel to the central axis, and/or the second tube is oriented within 30 degrees of parallel to the first tube.

In some embodiments, the storage system comprises a second retention member located inside the insulated container and configured to prevent the phase change system from blocking access to the medicine storage area. The insulated container can comprise a central axis. The second retention member can be located inside the insulated container in the proximal portion. The first and second retention members can hold the first and second tubes within 30 degrees of parallel to the central axis.

In several embodiments, the insulated container comprises a central axis. The storage system can have a plurality of tubes comprising the first tube and the second tube. The plurality of tubes can be spaced around an outer perimeter of the medicine storage area such that the plurality of tubes are located radially outward, relative to the central axis, from the medicine storage area.

In some embodiments, the first retention member secures the plurality of tubes radially outward from the medicine storage area and radially inward from an inner wall of a vacuum chamber that insulates the insulated container. The first retention member can comprise a cavity. The central axis of the insulated container can pass through the cavity. The cavity can comprise a portion of the medicine storage area. The first tube can be oriented within 30 degrees of parallel to the central axis. The second tube can be oriented within 30 degrees of parallel to the first tube. In some embodiments, the tubes are oriented parallel to the central axis.

In several embodiments, the first retention member comprises a protrusion oriented radially outward relative to the central axis. The protrusion can be located between the first tube and the second tube.

In some embodiments, the first retention member comprises a first wall located between the inner wall and the first tube. The first retention member can comprise a second wall located between the first tube and the medicine storage area.

In several embodiments, the first retention member comprises a first hoop and a second hoop. The first tube can be located at least partially in the first hoop. The second tube can be located at least partially in the second hoop.

In some embodiments, retention members can deform to fit through a narrow opening of the insulated container. Once inside the insulated container, the retention members can spring back to a larger shape (than could fit through the opening without deformation). The first retention member can comprise a maximum diameter measured radially outward relative to the central axis. The opening can comprise a minimum diameter measured radially outward relative to the central axis. The maximum diameter of the first retention member can be larger than the minimum diameter of the opening. The first retention member can be configured to change shape in a reversible manner to reduce the maximum diameter to enable inserting the first retention member through the opening. The first retention member can be configured to return to a shape having the maximum diameter after the first retention member has passed through the opening.

In several embodiments, the first tube comprises a first cylindrical portion at least partially filled with the first phase change material, and the second tube comprises a second cylindrical portion at least partially filled with the second phase change material. The first tube can be oriented parallel to the central axis, and the second tube can be oriented parallel to the central axis.

In some embodiments, the first tube comprises outer dimensions characterized by a thickness and a width. The first tube has a maximum thickness measured in a direction radially outward from the central axis of the insulated container. The first tube comprises a maximum width measured perpendicular to the maximum thickness and perpendicular to the central axis. In several embodiments, the maximum width is at least two times larger than the maximum thickness. The first tube can be a portion of a wedge shape (e.g., with rounded edges). This shape can help fit several tubes around a perimeter of a circle or oval shaped medicine storage area. The tube can include a lid configured to cover an opening to the tube. The lid can be laser welded to the tube. The lid can be coupled to the tube using processes used to attach lids to aluminum soda cans and/or processes used to attach lids to "tin cans" (which can be made from steel, aluminum, tin, or any other suitable metal).

In some embodiments, the first tube comprises at least one of fins, valleys, and detents configured increase a surface area of the first tube to promote heat transfer. The first retention member can comprise ventilation channels configured to enable airflow between the medicine storage area and the phase change system.

In several embodiments, the insulated container comprises a first central axis, the first tube comprises a second central axis, the second tube comprises a third central axis, and the medicine comprises a fourth central axis. The first retention member can orient the second, third, and fourth central axes within 30 degrees of parallel to the first central axis of the insulated container. The second, third, and fourth central axes can be located radially outward relative to the first central axis of the insulated container.

In some embodiments, the first tube comprises a cross section that is perpendicular to the second central axis. The cross section can have three outermost points that form a triangle. Walls of the first tube that connect the three outermost points can be at least one of straight and curved.

In several embodiments, a medicine storage system comprises an insulated container having an opening; a first lid configured to cover the opening; a phase change system located inside the insulated container; a medicine storage area located inside the insulated container; and a first retention member located inside the insulated container and configured to prevent the phase change system from blocking access to the medicine storage area. The storage system can be configured to provide access for inserting a medicine through the opening and into the medicine storage area.

In several embodiments, the phase change system comprises a first container having a first phase change material and a second container having a second phase change material. The first and second containers can be spherical, cylindrical, or any other suitable shape. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

In some embodiments, the first retention member comprises a tube located inside the insulated container such that the tube is in fluid communication with the opening. The storage system can be configured to enable inserting the medicine through the opening and into the tube. The tube can extend from a distal portion of the insulated container to a proximal portion of the insulated container. The first and second containers can be located between an inner wall of the insulated container and an outer wall of the tube.

In several embodiments, the storage system further comprises a plurality of containers at least partially filled with at least one of the first phase change material and the second phase change material. In some embodiments, the plurality of containers are not coupled to each other such that the plurality of containers are movable within an area between the inner wall of the insulated container and the outer wall of the tube.

In some embodiments, a storage system comprises a thermometer configured to measure a temperature of an interior area of the insulated container; a wireless communication system communicatively coupled with a remote computing device; and a first wireless communication sent from the medicine storage system to the remote computing device in response to at least one of (1) the temperature falling below a predetermined minimum temperature threshold, (2) the temperature rising above a predetermined maximum temperature threshold, (3) falling below a first predetermined amount of time until the temperature is predicted to fall below the predetermined minimum temperature threshold, and (4) falling below a second predetermined amount of time until the temperature is predicted to rise above the predetermined maximum temperature threshold.

In some embodiments, a storage system comprises a thermometer configured to measure a temperature of an interior area of the insulated container; and a computing system configured to emit at least one of a visual indicator and an audio indicator in response to at least one of (1) the temperature falling below a predetermined minimum temperature threshold, (2) the temperature rising above a predetermined maximum temperature threshold, (3) falling below a first predetermined amount of time until the temperature is predicted to fall below the predetermined minimum temperature threshold, and (4) falling below a second predetermined amount of time until the temperature is predicted to rise above the predetermined maximum temperature threshold.

In several embodiments, a storage system has a lid configured to cover an opening of an insulated container. The lid can comprise a thermometer system configured to measure a temperature of an interior area of the insulated container. The lid can comprise a display configured to show the temperature. The lid can comprise an inward portion and an outward portion. The inward portion can be located closer to the medicine storage area than the outward portion of the lid. A portion of the thermometer system can be coupled to the inward portion of the lid such that the portion of the thermometer system is configured to sense the temperature of the interior area. The display can be located on an outward facing side of the lid such that the display is configured to show the temperature even when the lid is screwed onto the insulated container. The thermometer system and the display can be electrically coupled to a computing system configured to enable the storage system to measure the temperature and show the temperature on the display.

BRIEF DESCRIPTION OF THE DRAWINGS

These and other features, aspects, and advantages are described below with reference to the drawings, which are intended to illustrate but not to limit the invention. In the drawings, like reference characters denote corresponding features consistently throughout similar embodiments.

FIG. 43 illustrates a side view of a tubular retention member, according to some embodiments.

FIG. 44 illustrates a top view of a tubular retention member, according to some embodiments.

FIG. 45 illustrates a perspective view of a tubular retention member, according to some embodiments.

FIG. 76 illustrates a side view of a lid, according to some embodiments.

FIG. 77 illustrates an enlarged view of the area indicated by circle R in FIG. 78, according to some embodiments.

FIG. 78 illustrates a cross-sectional view taken along line 78-78 from FIG. 76, according to some embodiments.

DETAILED DESCRIPTION

Figure 1:
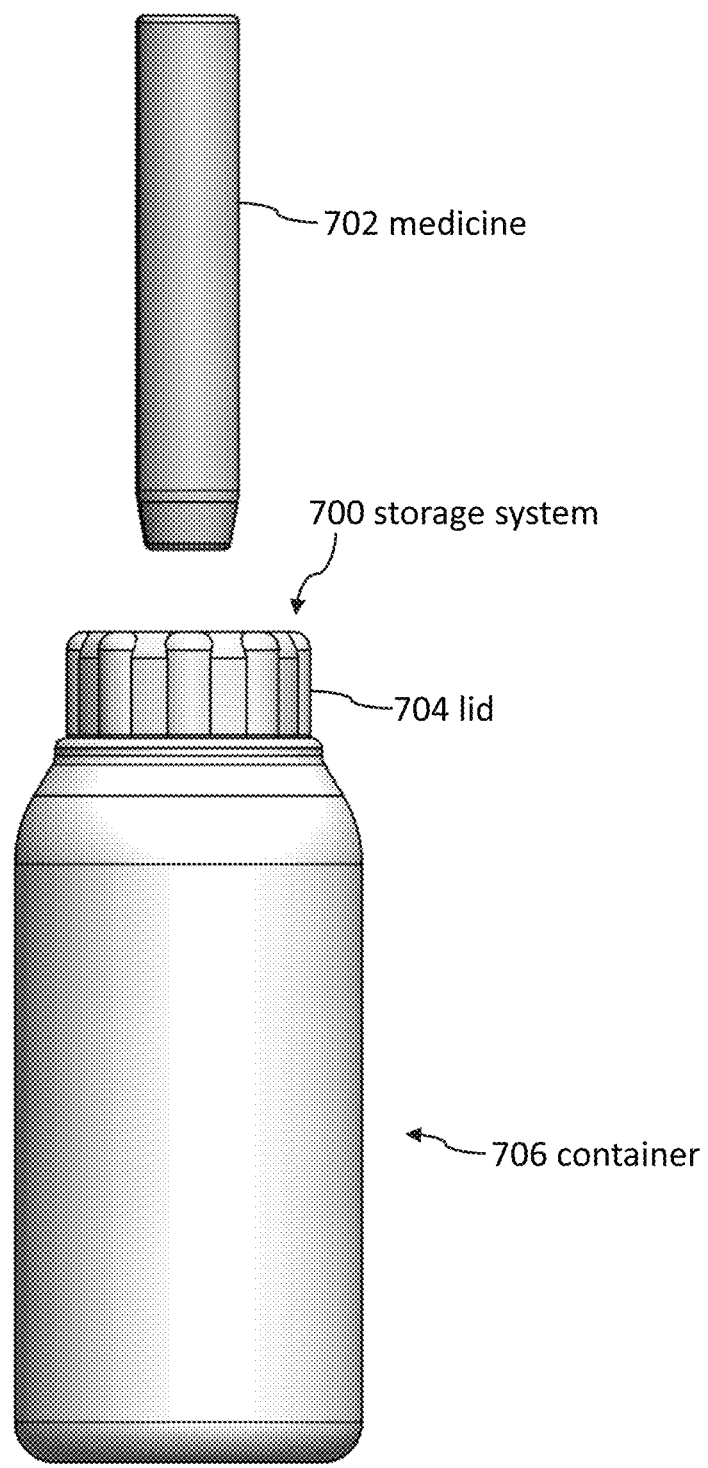
FIG. 1 illustrates a side view of a storage system, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. The features of each embodiment can be combined with the other embodiments.

People can damage their medicines by taking them outside in hot or cold weather. On the other hand, some people need to carry their medicines with them wherever they go (even if the weather is extremely hot or cold). Specially constructed storage systems can protect medicines from damage due to hot and cold weather without requiring bulky structures or expensive components that consume electricity to regulate temperature.

Any of the embodiments illustrated herein and/or incorporated by reference can include a storage system comprising a phase change system; a first container configured to hold at least a portion of the phase change system; and a first chamber located within the first container and configured to hold a medicine. As explained herein, phase change systems can comprise a first phase change material and/or a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. Thus, the phase change system can protect the medicine from temperatures above and below room temperature.

Refrigeration systems typically are large, expensive, fragile, and use electricity to regulate temperature. In contrast, phase change systems can be configured to protect medicine from a first external temperature less than a minimum recommended storage temperature and from a second external temperature greater than a maximum recommended storage temperature by utilizing phase changes to regulate a temperature of the medicine. Because phase change systems do not require electronics and pumps, they are very robust and can be built for a small fraction of the cost of refrigeration systems. Imagine a child who needs an epinephrine injector having to carry even a small refrigerator wherever she goes to prevent hot temperatures from ruining her potentially life-saving epinephrine.

In stark contrast, the child could easily carry a medicine storage system that relies on the phase change systems described herein, which can even be designed to protect against both hot and cold temperatures to eliminate the need for the child to have to guess which temperature protection components she will need for a trip. For example, if the child goes camping, she may need to protect her medicine against both hot afternoon temperatures and cold nighttime temperatures.

Containers can come in many different shapes and sizes. Some containers are vacuum flasks. Vacuum flasks can prevent high heat transfer rates to enable minimizing the amount of phase change material necessary to adequately protect a medicine. Thus, the system can be smaller than would be the case without a vacuum flask.

On the other hand, vacuum flasks often have rigid outer walls, which can make carrying them uncomfortable. Some containers are compliant bags with flexible walls. Compliant bags can be very comfortable to carry. Their flexible outer walls can facilitate fitting them into backpacks and purses (by enabling them to conform to various shapes).

FIG. 1 illustrates a side view of a storage system 700. FIG. 1 shows a medicine 702 (e.g., an EpiPen). A lid 704 can be removed (e.g., unscrewed) from the container 706 to facilitate placing the medicine 702 include the storage system 700.

Figure 2:
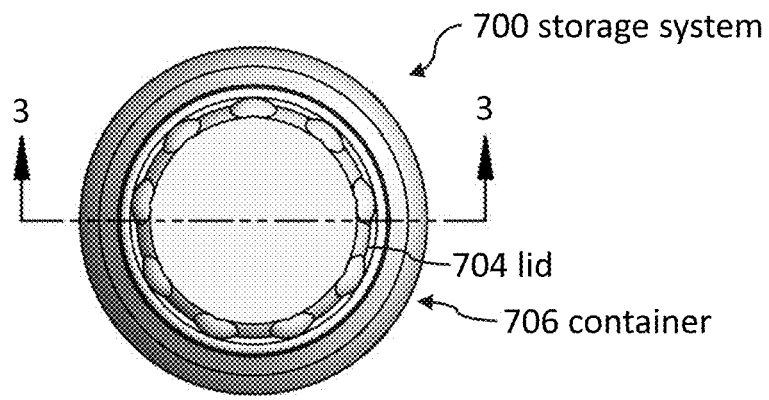
FIG. 2 illustrates a top view of a storage system, according to some embodiments.
Figure 3:
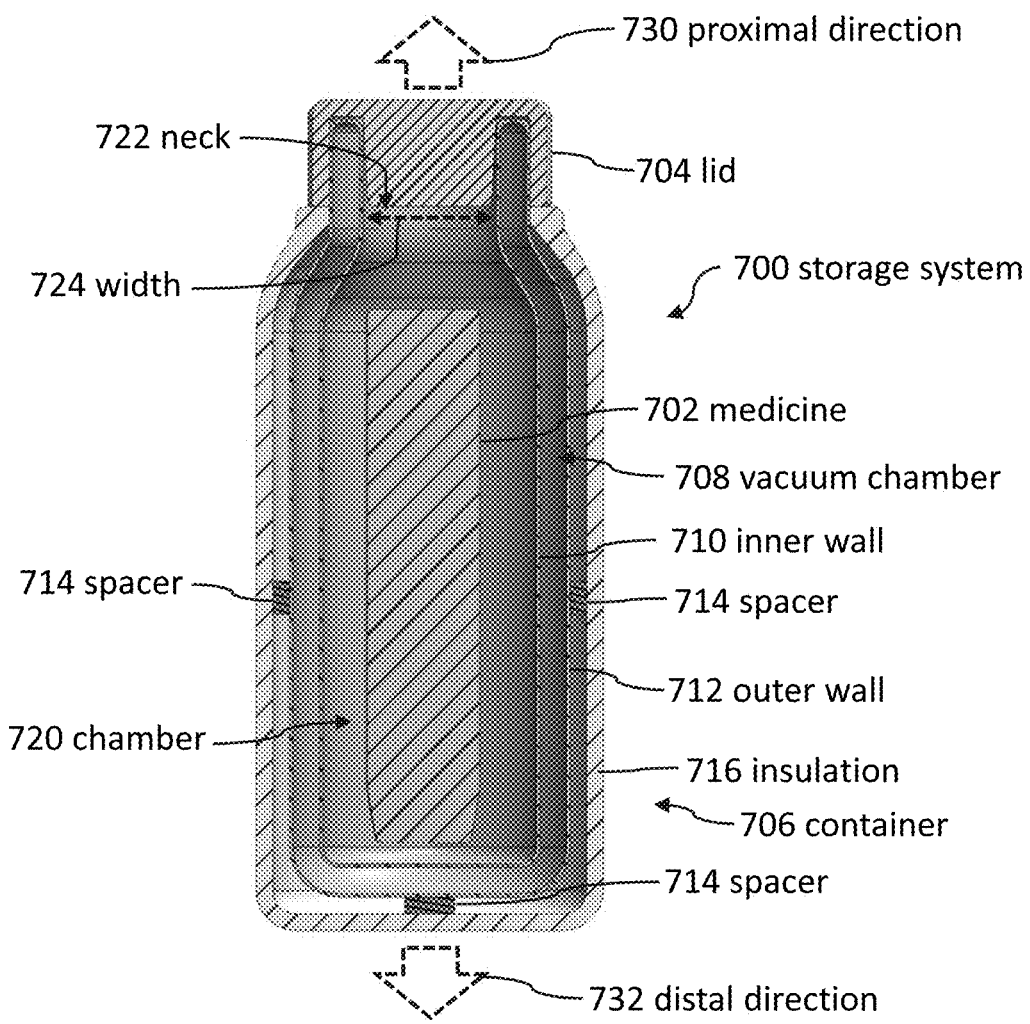
FIG. 3 illustrates a cross-sectional view of a storage system along line 3-3 from FIG. 2, according to some embodiments.

FIG. 2 illustrates a top view of the storage system 700. FIG. 3 illustrates a cross-sectional view of the storage system 700 along line 3-3 from FIG. 2. The storage system 700 can include a vacuum chamber 708 formed by an inner wall 710 and an outer wall 712 (such that the vacuum chamber 708 is located between the walls 710, 712). The inner wall 710 and the outer wall 712 can be cylindrical or any other suitable shape.

The vacuum chamber 708 can at least partially surround a chamber 720 that holds the medicine 702. As illustrated in FIG. 3, an opening in the chamber 720 is plugged by the lid 704.

Insulating spacers 714 can couple an outer wall 712 of the vacuum chamber 708 to an outer insulated layer 716, which can be rigid or flexible. Some embodiments do not include the inner wall 710, the outer wall 712, and the vacuum chamber 708 (e.g., to facilitate making a storage system that is more flexible).

Some embodiments use portions (e.g., the insulation 716) that are made using rotational molding to create hollow parts. The hollow portions can be filled with insulation (e.g., injected with foam insulation). Portions (e.g., exterior walls) can be made from polyethylene.

Some embodiments use containers that are blow-molded. These blow-molded containers can form PCM chambers, which can hold phase change materials. The phase change materials can have any of the melting temperatures described herein or any other suitable melting temperature. Some containers have one, two, three, five, ten, or any other suitable number of PCM chambers.

Many embodiments of phase change systems can be added to the storage system 700. In several embodiments, the phase change systems are added such that they are located inside the container 706, inside the outer insulated layer 716, and/or inside the vacuum chamber 708.

One challenge of inserting a phase change system is that the width 724 of the neck 722 leading into the chamber 720 can be narrower than a distal portion of the chamber 720. As a result, some phase change systems cannot fit through the neck 722. The phase change system embodiments described herein use unique structures and assembly techniques to enable them to fit through the neck 722. As a result, the systems are highly space efficient and enable cost-effective high-volume manufacturing.

Figure 57:
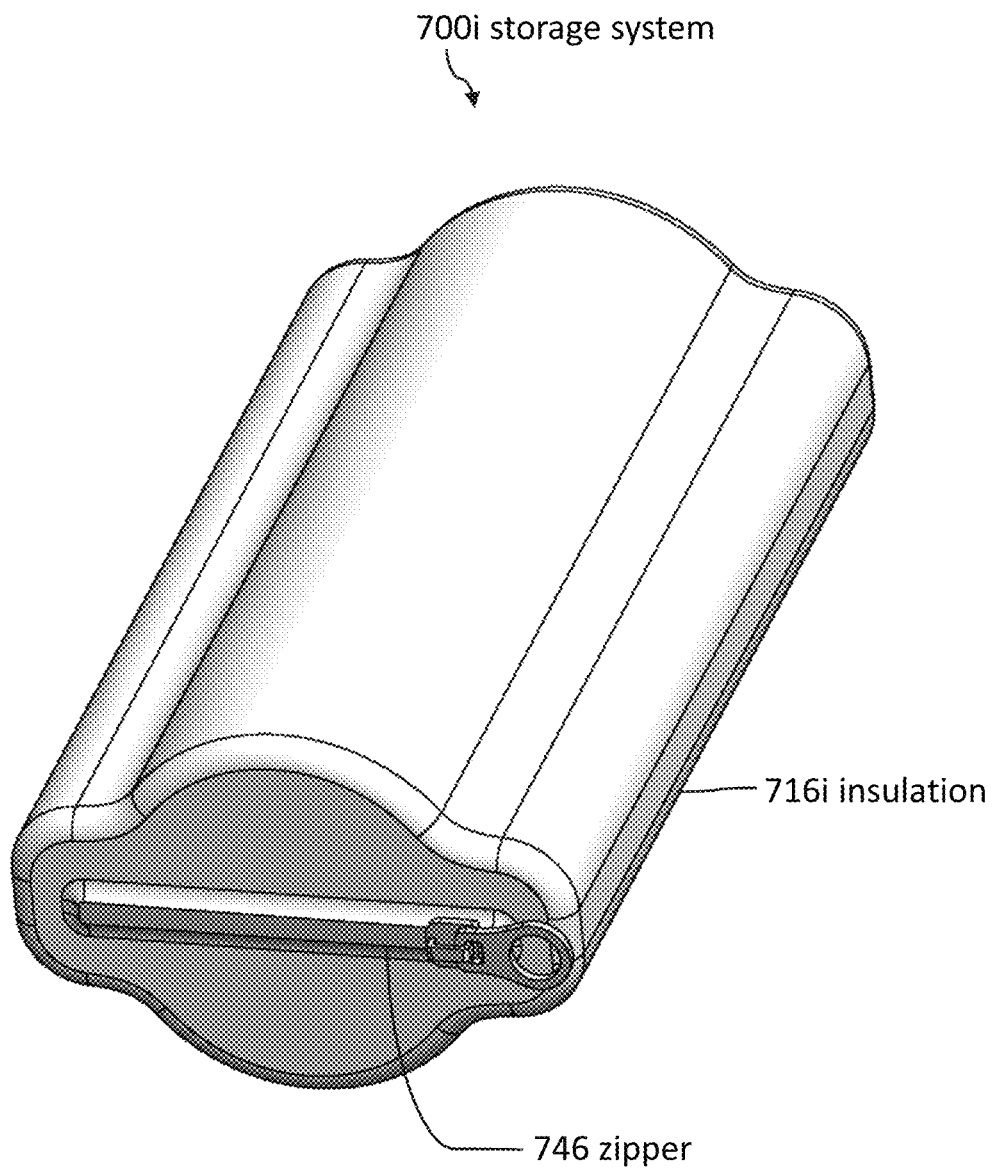
FIG. 57 illustrates a perspective view of a storage system having a flexible outer housing, according to some embodiments.

The phase change systems described herein can be added to the storage system 700 shown in FIG. 3 and to the storage system 700*i* shown in FIG. 57. The phase change systems described herein can comprise a first phase change material and/or a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. Thus, the phase change system can protect the medicine from temperatures above and below room temperature.

The phase change systems described herein can comprise a first phase change material having a first melting temperature greater than 40 degrees Fahrenheit and less than 74 degrees Fahrenheit; a second phase change material having a second melting temperature greater than the first melting temperature and less than 74 degrees Fahrenheit; a third phase change material having a third melting temperature greater than 74 degrees Fahrenheit and less than 100 degrees Fahrenheit; and/or a fourth phase change material having a fourth melting temperature greater than the third melting temperature and less than 100 degrees Fahrenheit.

Figure 4:
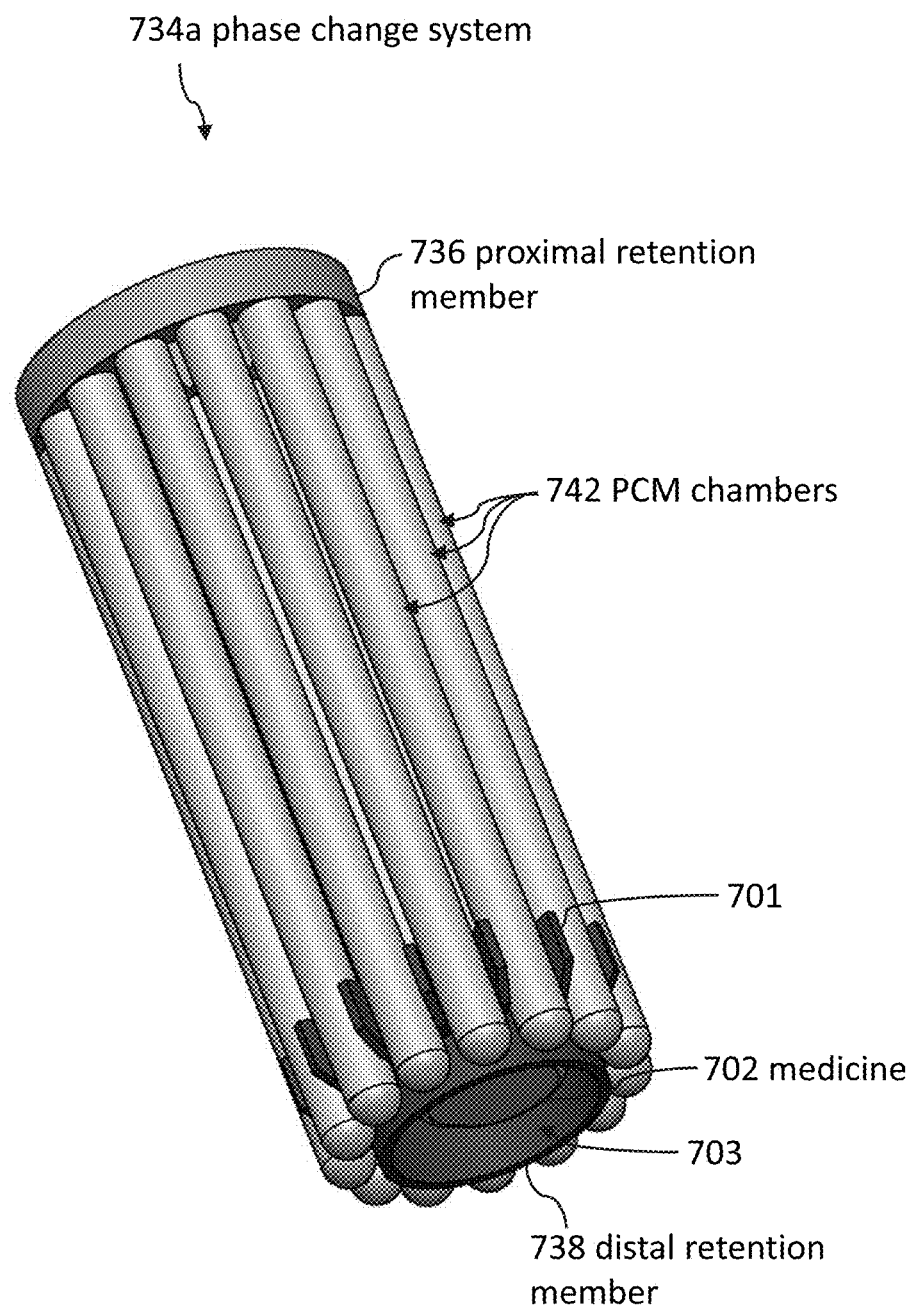
FIG. 4 illustrates a perspective view of a phase change system, according to some embodiments.

FIG. 4 illustrates a perspective view of a phase change system 734a configured to hold any combination of the phase change materials described herein. The phase change system 734a includes a proximal retention member 736 and a distal retention member 738 that secure phase change material ("PCM") chambers 742 around a perimeter of a chamber 740 configured to hold the medicine 702.

Each PCM chamber 742 can be filled with any of the phase change materials described herein (or incorporated by reference) and can be sealed to prevent leaking. The PCM chambers 742 can be hollow molded plastic tubes filled with PCM and then sealed.

The PCM chambers 742 can be hollow metal tubes filled with PCM and then hermetically sealed by a lid. The PCM chambers 742 can be made from aluminum, tin, steel, or any other suitable metal. The lid can be coupled to the tube using the same processes used to couple a lid to an aluminum soda can. The lid can be coupled to the tube by an "open top can sealer" sold by House of Cans, Inc. The can sealer can be manual or electric.

The lid can include protrusions to strengthen the lid. For example, the lid does not need to be flat, but instead can include ridges, bumps, and protrusions to strengthen the lid. Strengthening the lid can help make the PCM chamber 742 strong enough to tolerate the expansion and contraction typical of freezing and thawing PCMs.

The PCM chambers 742 can be formed by computer numerical control ("CNC") machining with wall thicknesses between 0.3 millimeters and 1.5 millimeters.

The PCM chambers 742 can be formed using processes typically used to form aluminum soda cans. Example processes include blanking, deep drawing, wall-ironing, end forming, trimming, washing, outside coating (e.g., to protect against corrosion), printing, drying, internal coating (e.g., to protect the metal and/or to protect the PCM from contamination), necking, flanging, end coating, testing for holes, and testing for internal defects. The PCM chambers 742 can be made from aluminum and then coated to guard against corrosion.

In some embodiments, the PCM chambers 742 have a diameter of at least 8 millimeters, at least 12 millimeters, less than 22 millimeters, and/or less than 30 millimeters. In some embodiments, the PCM chambers 742 have a length of at least 40 millimeters, at least 80 millimeters, less than 170 millimeters, and/or less than 185 millimeters.

The distal retention member 738 can be molded from compliant rubber that enables the distal retention member 738 to deform to enable a person to insert each PCM chamber.

Figure 5:
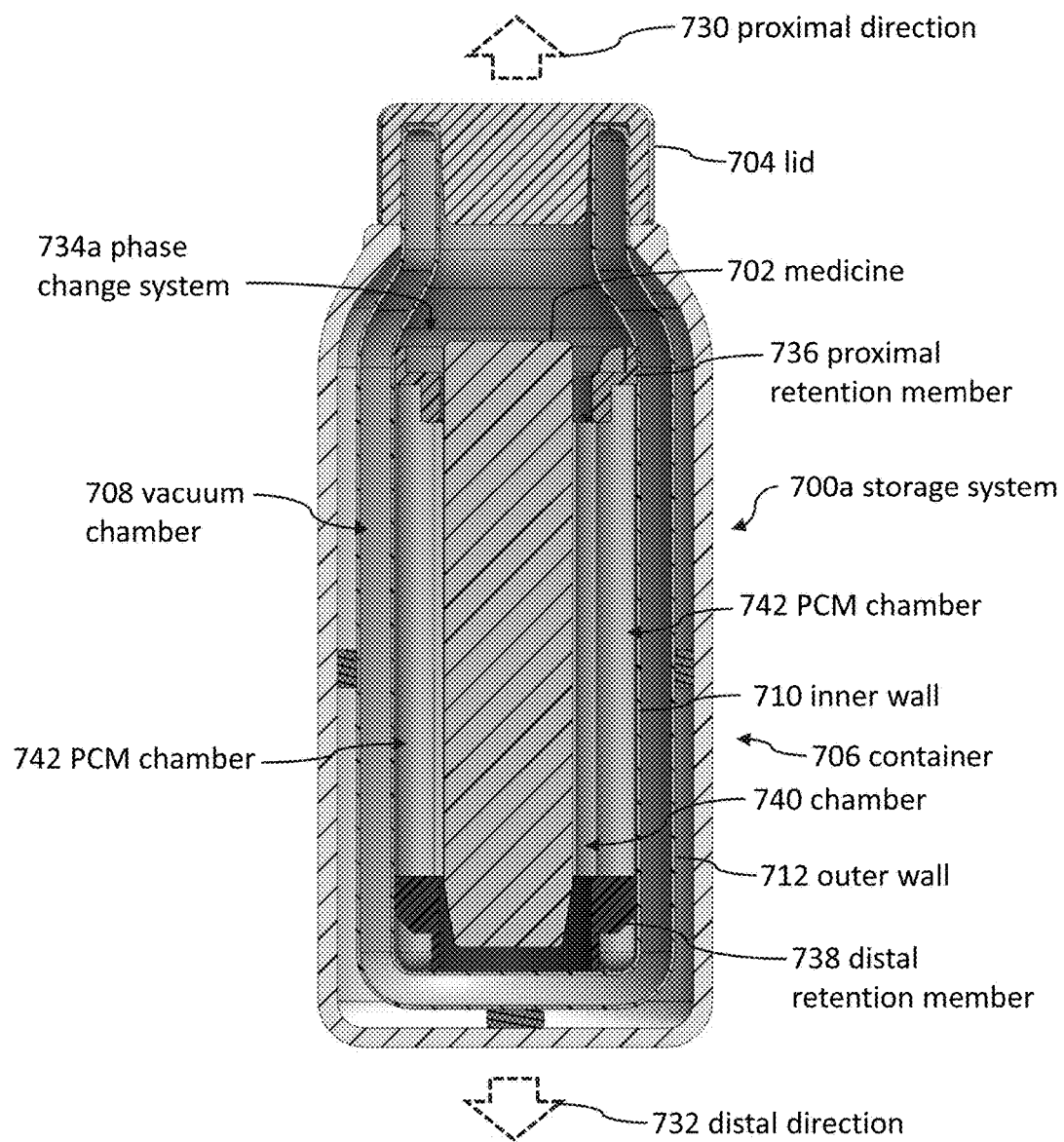
FIG. 5 illustrates the same cross section as FIG. 3 except that a phase change system is shown, according to some embodiments.
Figure 6:
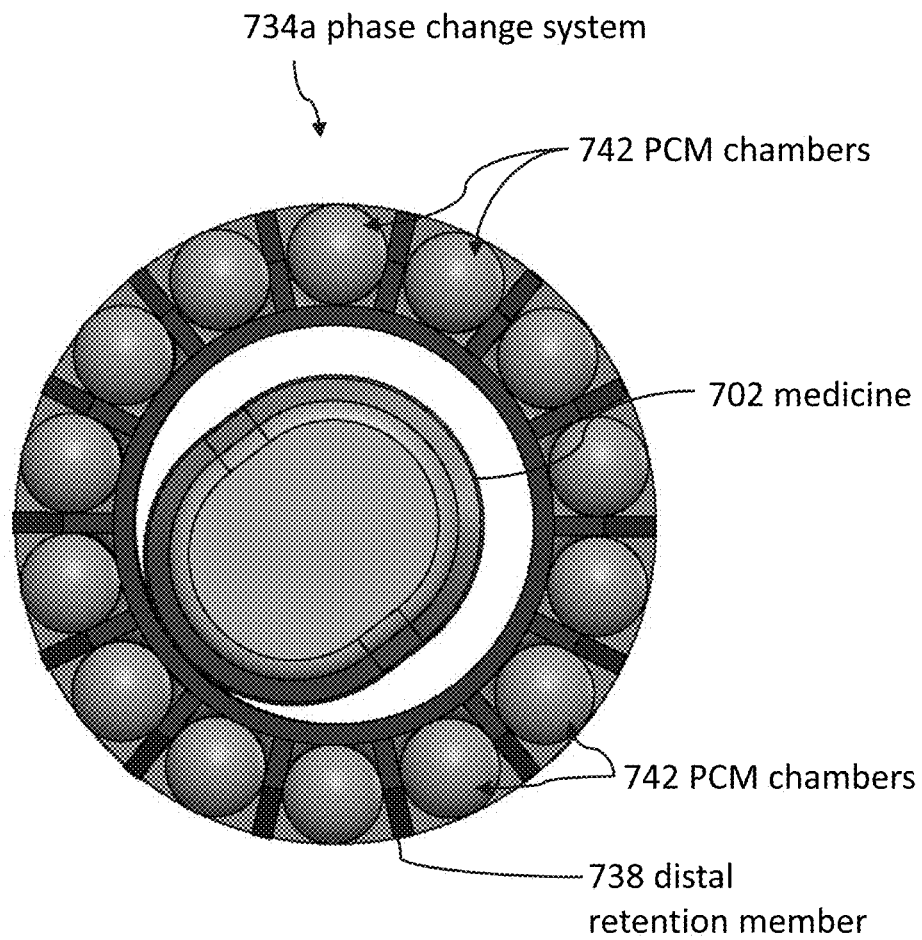
FIG. 6 illustrates a bottom view of a medicine at least partially surrounded by a phase change system, according to some embodiments.
Figure 7:
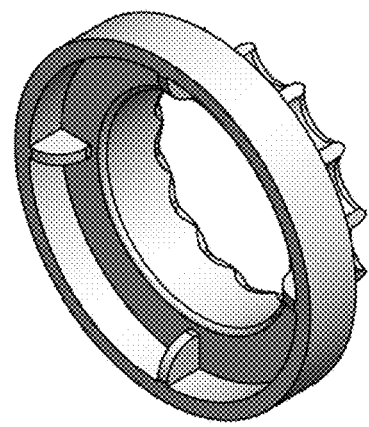
FIG. 7 illustrates a perspective view of a proximal retention member, according to some embodiments.
Figure 8:
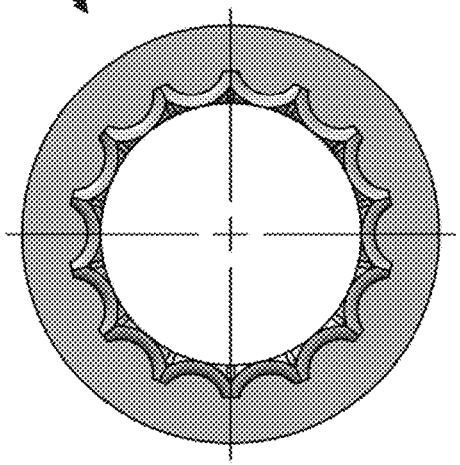
FIG. 8 illustrates a bottom view of a proximal retention member, according to some embodiments.
Figure 9:
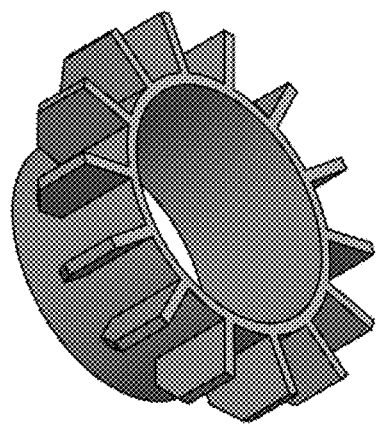
FIGS. 9 and 10 illustrate perspective views of a distal retention member, according to some embodiments.
Figure 10:
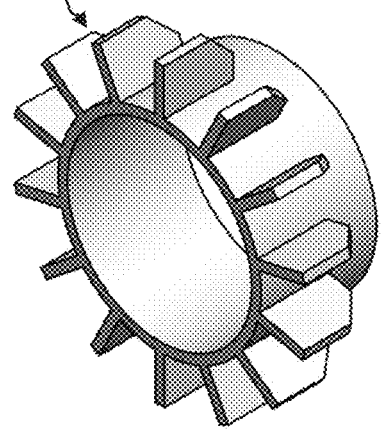

FIG. 5 illustrates the same cross section as FIG. 3 except that the phase change system 734a is shown. The storage system 700a can be assembled by inserting the distal retention member 738, inserting each PCM chamber 724 (e.g., one at a time), and then securing the proximal ends of the PCM chambers 724 by pressing the proximal retention member 736 through the neck 722 (labeled in FIG. 3). The proximal retention member 736 can be molded from flexible rubber to enable the proximal retention member to deform elastically to a small enough shape to fit through the neck 722. Then, once the proximal retention member 736 has moved distally past the neck 722, the proximal retention member 736 can spring back to essentially its original shape.

Phase change materials can be held in many different types of containers. Some embodiments use molded plastic containers to hold phase change materials. A phase change material can be poured into a container (e.g., while the phase change material is in a liquid state). The container can be sealed with a plastic lid that is coupled to the opening of the container.

Some embodiments use film pouches to hold phase change materials. The pouches can be hermetically sealed to prevent leakage.

The surface area of the container can be increased by molding fins, valleys, detents, concave features, convex features, etc. into the walls of the container. Increasing the surface area of the container's walls can increase the rate of heat transfer to and from the phase change material inside the container, which can reduce temperature differences between the medicine and the phase change material.

Vesl, LLC, which has an office in Melbourne, Fla., makes the following containers to hold a wide variety of phase change materials: BlockVesl (a stackable container with domed walls to increase heat transfer), MacroVesl (a blow-molded sphere having many chambers that hold phase change materials), MicroVesl (a spherical container having a multi-layer polymer structure), PackVesl (a highly flexible pouch made from multiple layered film and hermetically sealed to prevent leakage or intrusion), TubeVesl (a tube sealed with a lid), CanVesl (a metal cylinder), and MatVesl (a multi-layer barrier film sheet having blisters filled with PCM).

Phase Change Energy Solutions, which has an office in Asheboro, N.C., also makes containers that hold phase change material. Microtek Laboratories, Inc., having an office in Dayton, Ohio, also makes containers that hold phase change material.

Figure 11:
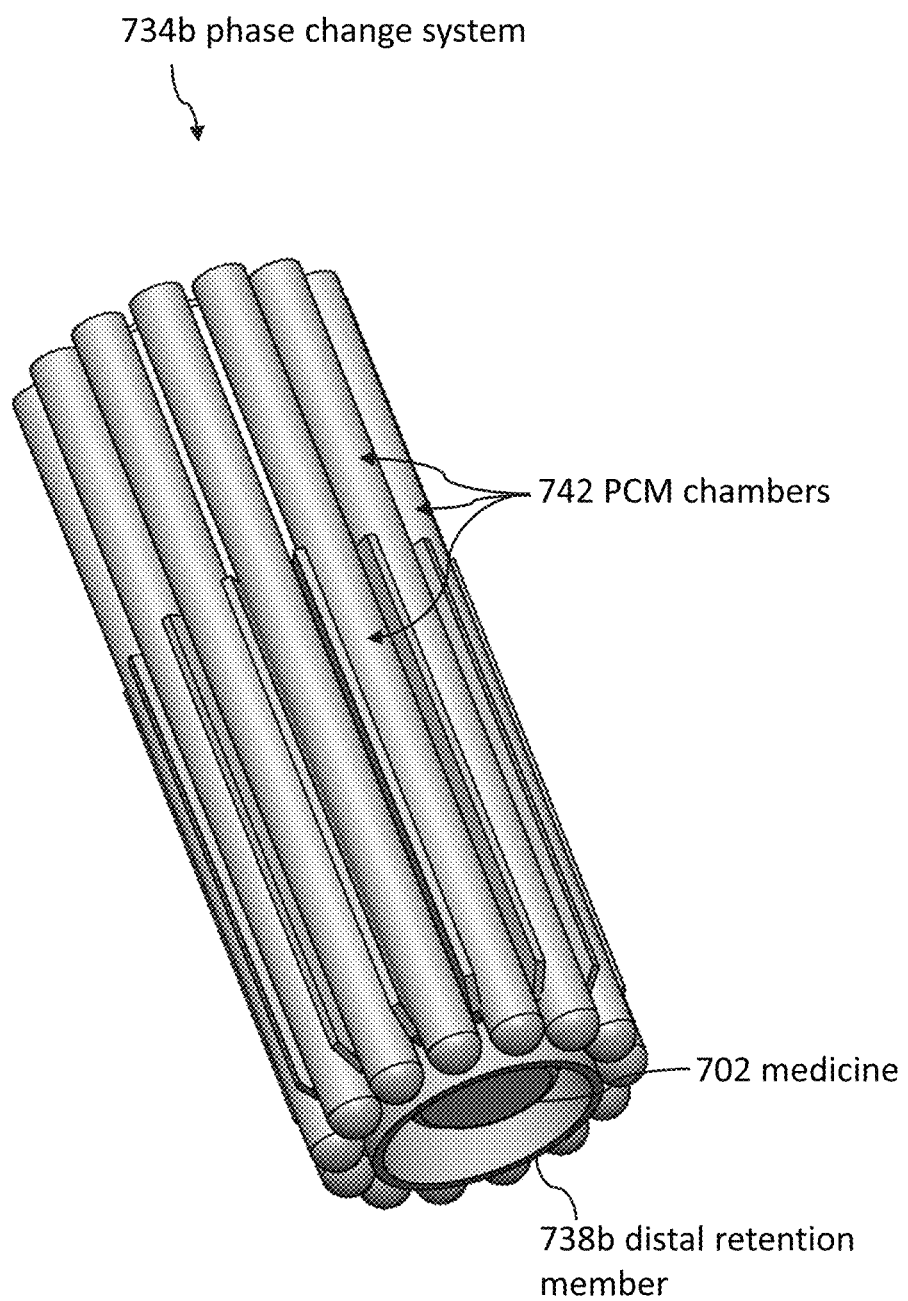
FIG. 11 illustrates a perspective view of a phase change system having PCM chambers in tubular containers that extend from a distal portion of the storage system to a proximal portion of the storage system, according to some embodiments.
Figure 12:
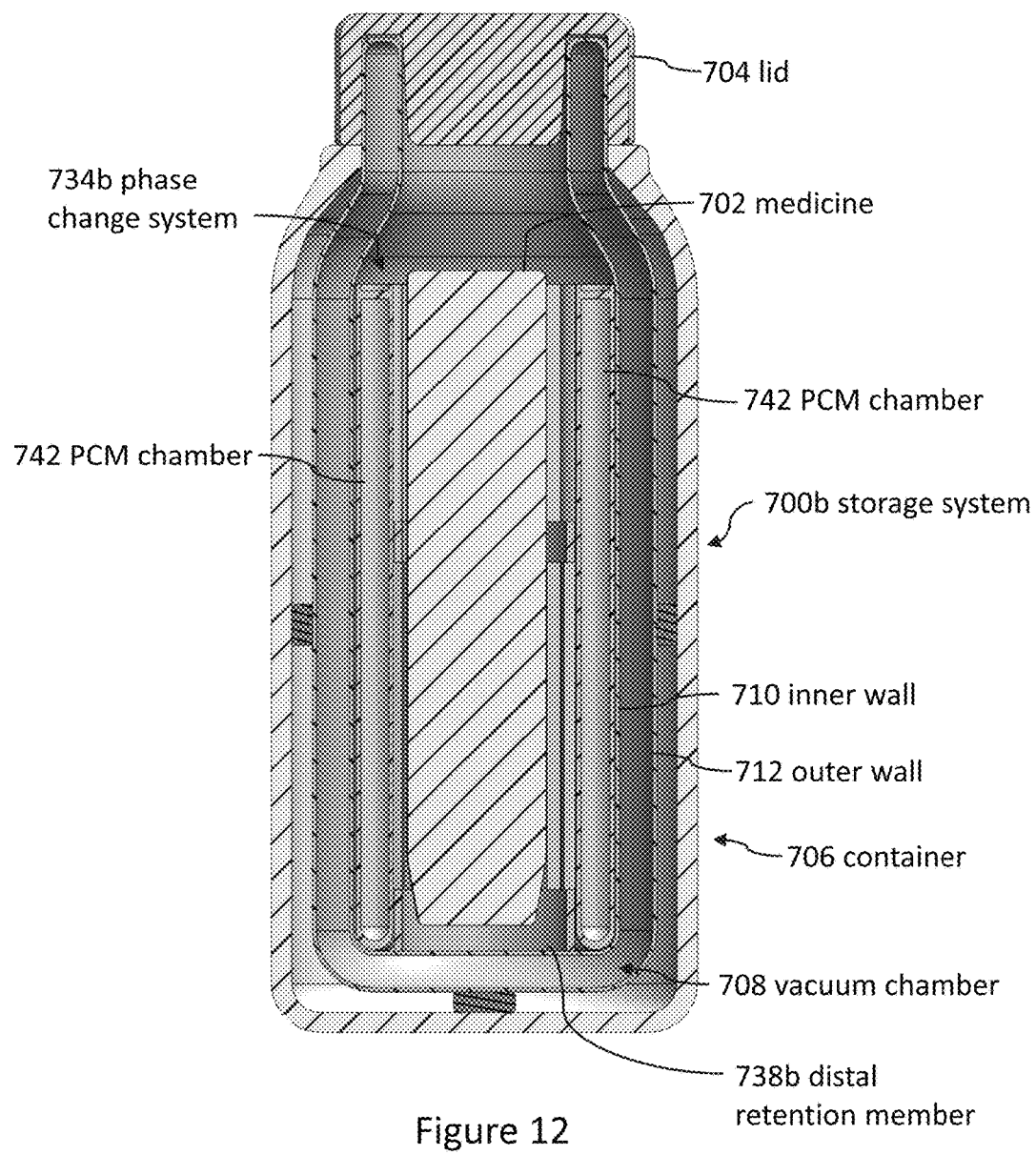
FIG. 12 illustrates the same cross section as FIG. 3 except that a phase change system is shown, according to some embodiments.

FIG. 11 illustrates a perspective view of a phase change system 734b having PCM chambers 742 in tubular containers that extend from a distal portion of the storage system 700b to a proximal portion of the storage system 700b (as shown in FIG. 12).

As used herein, "extends" means to continue in a specified direction or over a specified distance, but unless stated otherwise, typically does not mean to become longer.

The PCM chambers can alternate between a first PCM and a second PCM around the perimeter of the distal retention member 738b. For example, a first PCM chamber 742 can include a first phase change material, a second PCM chamber 742 that is adjacent to the first PCM chamber 742 can include a second phase change material with a higher melting temperature than the first phase change material, and a third PCM chamber 742 that is adjacent to the second PCM chamber 742 can include the first phase change material. Thus, in some embodiments, first and second phase change materials are approximately evenly spread around the perimeter of the distal retention member 738*b* to minimize temperature differences inside the container 706 (shown in FIG. 12).

Figure 13:
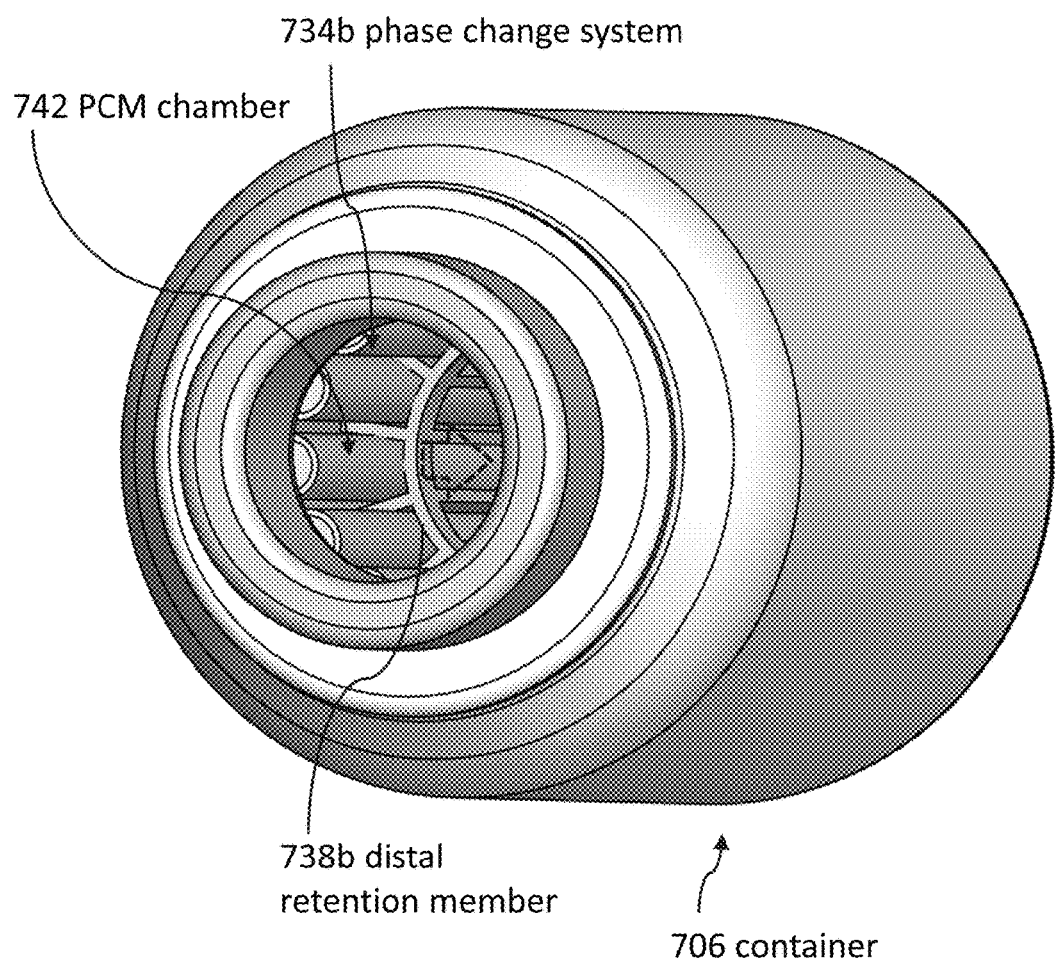
FIG. 13 illustrates a perspective view of a container without a lid, according to some embodiments.

FIG. 12 illustrates the same cross section as FIG. 3 except that the phase change system 734*b* is shown. FIG. 13 illustrates a perspective view of the container 706 without the lid 704 (shown in FIG. 1). The distal retention member 738*b* can be molded from a flexible material (such as a rubber with a hardness of 60 to 95 shore A). An inner wall (e.g., a portion of an inner hoop) can flex radially inward as shown by the arrow in FIG. 13. This elastic deformation can enable inserting a PCM chamber container through a narrow neck.

Figure 14:
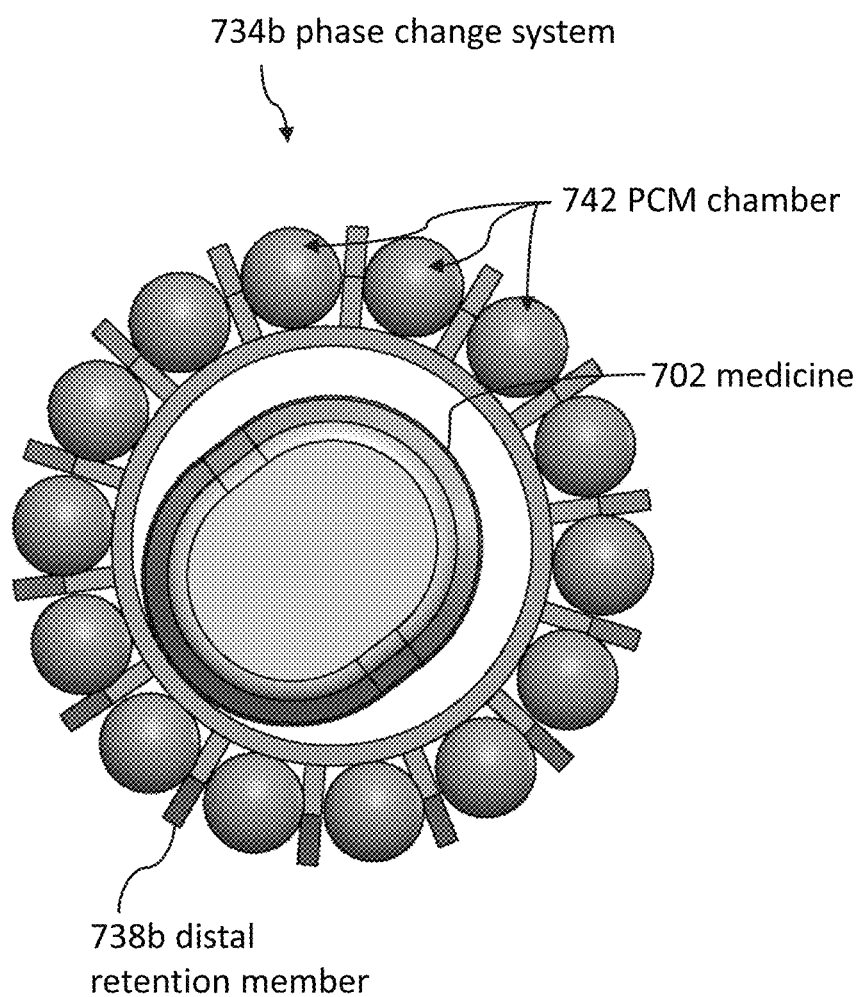
FIG. 14 illustrates a bottom view of a medicine and a phase change system, according to some embodiments.
Figure 15:
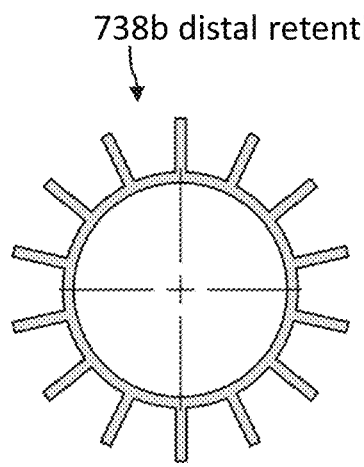
FIG. 15 illustrates a top view of a distal retention member, according to some embodiments.
Figure 16:
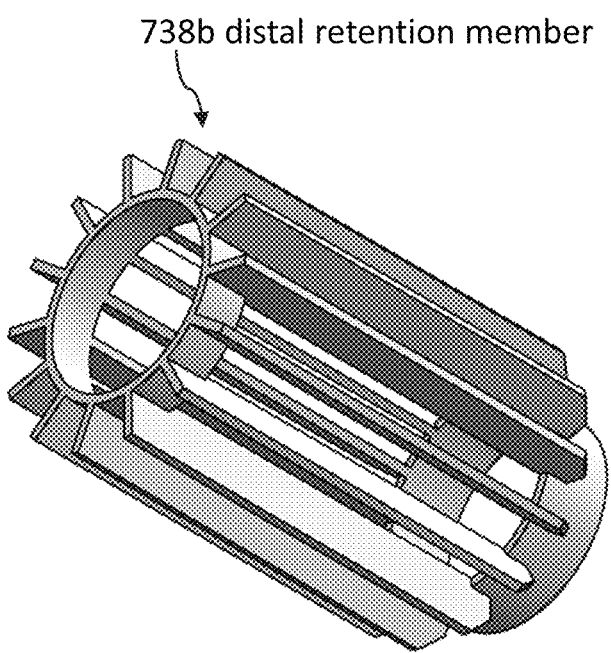
FIG. 16 illustrates a perspective view of a distal retention member, according to some embodiments.
Figure 17:
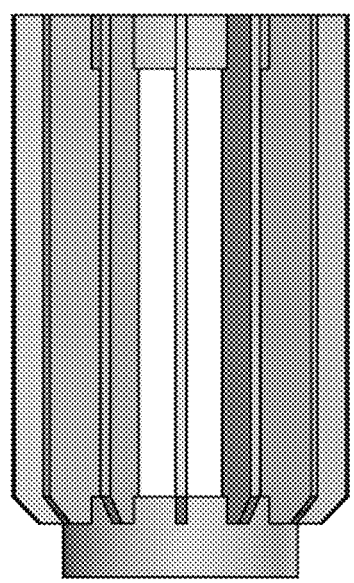
FIG. 17 illustrates a side view of a distal retention member, according to some embodiments.
Figures 18, 19:
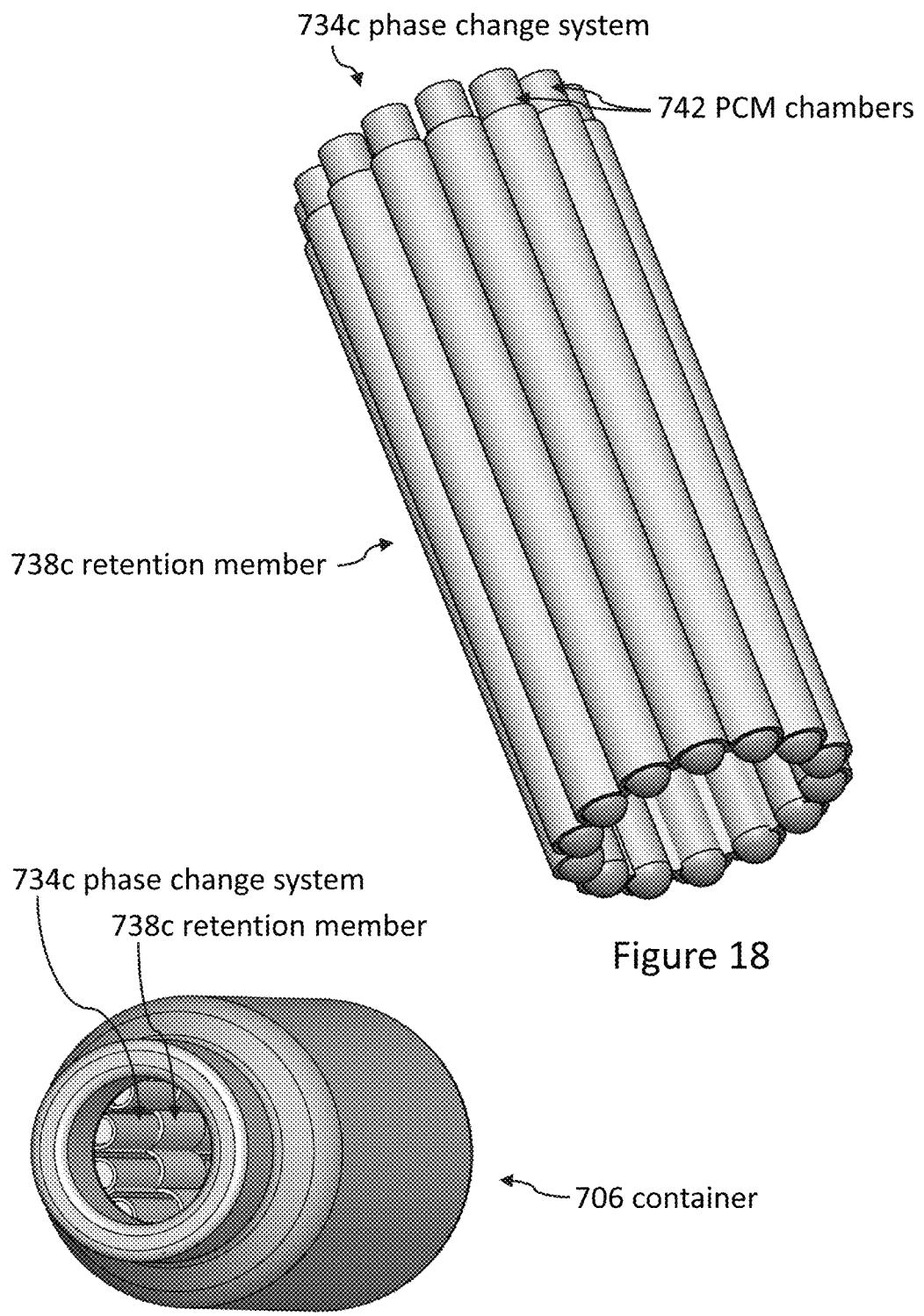
FIG. 18 illustrates a perspective view of a phase change system, according to some embodiments.
FIG. 19 illustrates a perspective view of a container without a lid, according to some embodiments.
Figure 20:
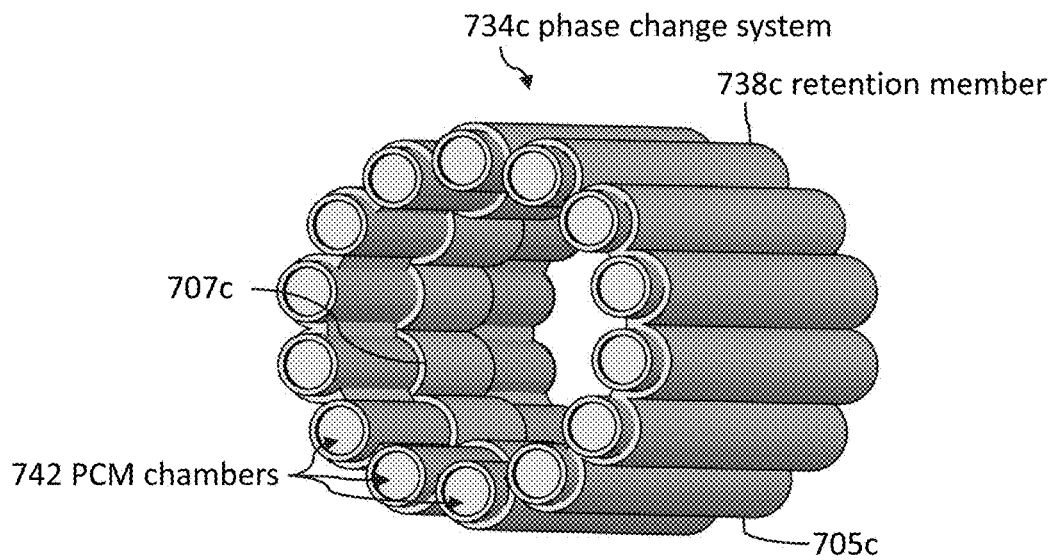
FIG. 20 illustrates a perspective view of a phase change system, according to some embodiments.
Figure 21:
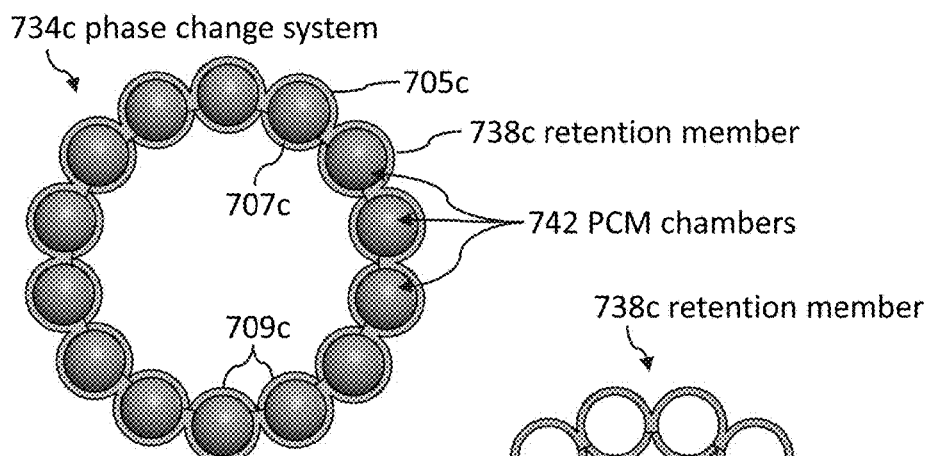
FIG. 21 illustrates a bottom view of a phase change system, according to some embodiments.
Figure 22:
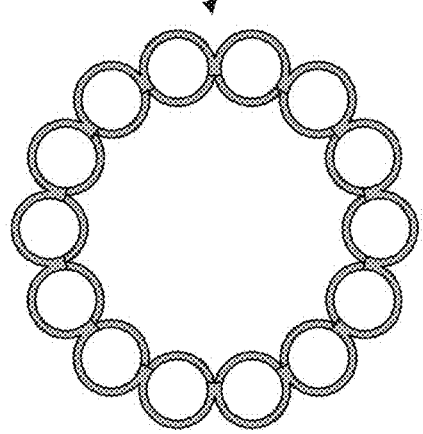
FIG. 22 illustrates a bottom view of a retention member, according to some embodiments.

FIG. 14 illustrates a bottom view of the phase change system 734*b*. FIGS. 15-17 illustrate various views of the distal retention member 738*b* shown in FIG. 11.

Figure 79:
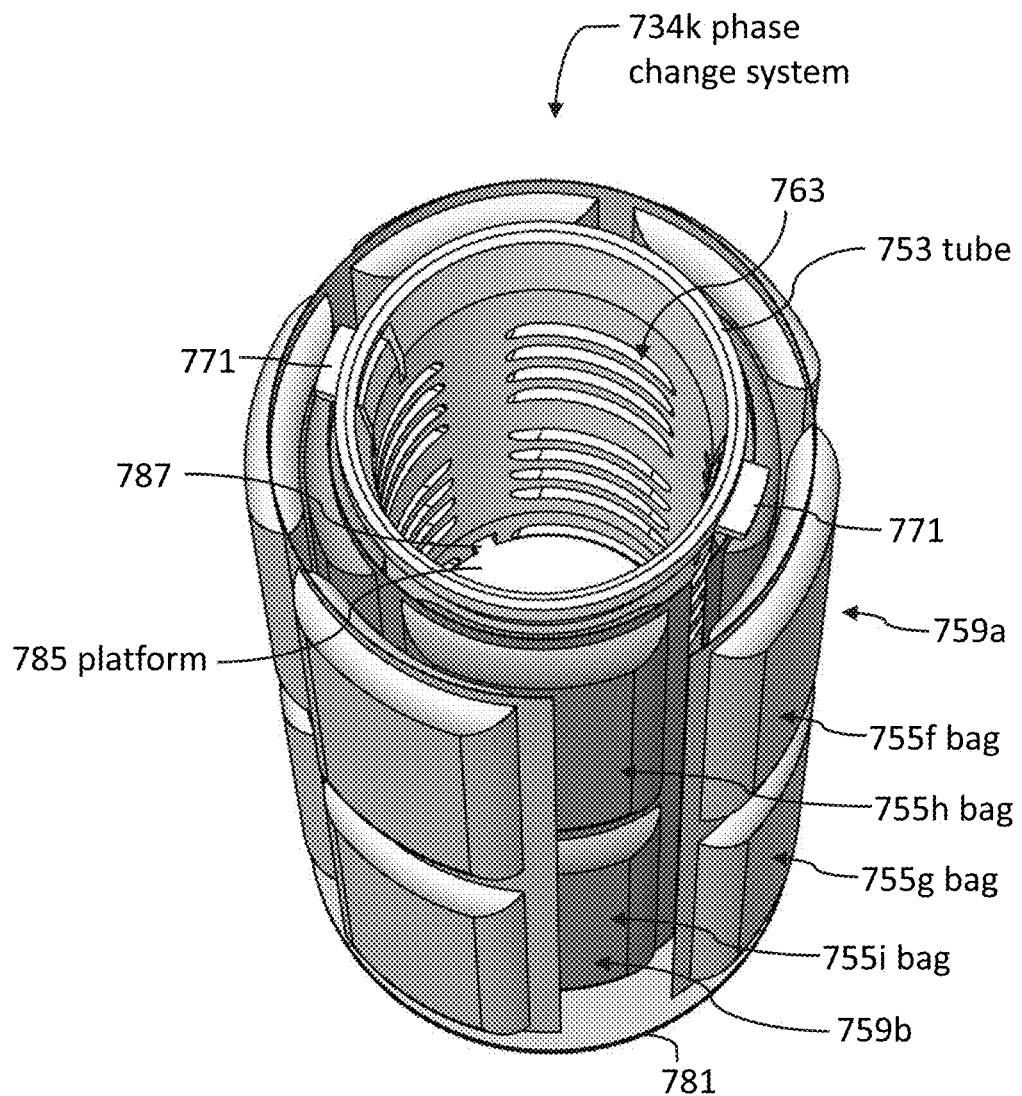
FIG. 79 illustrates a perspective view of a phase change system, according to some embodiments.

As shown in FIGS. 4-79, in some embodiments, a medicine storage system comprises an insulated container having an opening; a first lid configured to cover the opening; a phase change system located inside the insulated container; a medicine storage area located inside the insulated container; and a first retention member located inside the insulated container and configured to prevent the phase change system from blocking access to the medicine storage area. The storage system can be configured to provide access for inserting a medicine through the opening and into the medicine storage area.

As shown in FIGS. 4-6, 11-14, 18-21, 31-37, and 49-54, in several embodiments, the phase change system comprises a first tube having a first phase change material and a second tube having a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

The PCM chambers 742, 742*e*, 742*h* in FIGS. 4-6, 11-14, 18-21, 31-37, 49, 50, and 52-54 are located inside hollow metal tubes at least partially filled with PCM and sealed with a lid. The metal tubes can be extruded and/or machined tubes. The tubes can have any suitable shape. The tubes can have circular cross sections, crescent cross sections, and/or triangular cross sections. In some embodiments, the tube shape varies along a central axis of the tube such that a first cross section at one distance from a distal end of the tube has a different shape than a second cross section at another distance from the distal end.

Referring mainly to FIG. 5, but also to FIGS. 4, 6, 11-14, 18-21, 31-37, and 49-54, the insulated container comprises a proximal portion and a distal portion. The distal portion is located farther from the opening (covered by the lid 704 in FIG. 5) than the proximal portion. The first retention member (e.g., 738, 738*b*, 738*c*, 738*e*, 738*h*) can be located inside the insulated container 706 in the distal portion. The first retention member can comprise a protrusion (e.g., 701) between the first tube and the second tube.

In several embodiments, the first retention member comprises a cavity (e.g., 703), the insulated container comprises a central axis that passes through the cavity, the cavity comprises a portion of the medicine storage area, the protrusion of the first retention member is oriented radially outward relative to the central axis, the first tube is oriented within 30 degrees of parallel to the central axis, and/or the second tube is oriented within 30 degrees of parallel to the first tube.

In some embodiments, the storage system comprises a second retention member (e.g., 736) located inside the insulated container and configured to prevent the phase change system from blocking access to the medicine storage area. The insulated container can comprise a central axis. The second retention member can be located inside the insulated container in the proximal portion. The first and second retention members can hold the first and second tubes within 30 degrees of parallel to the central axis (e.g., as shown in FIG. 5).

In several embodiments, the insulated container comprises a central axis. The storage system can have a plurality of tubes comprising the first tube and the second tube. The plurality of tubes can be spaced around an outer perimeter of the medicine storage area such that the plurality of tubes are located radially outward, relative to the central axis, from the medicine storage area (e.g., as shown in FIGS. 4-6, 11, 12, 14, 18-21, and 31-33).

In some embodiments, the first retention member secures the plurality of tubes radially outward from the medicine storage area and radially inward from an inner wall of a vacuum chamber that insulates the insulated container (e.g., as shown in FIGS. 4-6, 11, 12, 14, 18-21, and 31-33). The first retention member can comprise a cavity. The central axis of the insulated container can pass through the cavity. The cavity can comprise a portion of the medicine storage area (e.g., as shown in FIGS. 4-6, 11, 12, 14, 18-21, and 31-33). The first tube can be oriented within 30 degrees of parallel to the central axis. The second tube can be oriented within 30 degrees of parallel to the first tube. In some embodiments, the tubes are oriented parallel to the central axis (e.g., as shown in FIGS. 4-6, 11, 12, 14, 18-21, and 31-33).

In several embodiments, the first retention member comprises a protrusion oriented radially outward relative to the central axis. The protrusion can be located between the first tube and the second tube.

Referring now to FIGS. 20, 21, 50, and 52, in some embodiments, the first retention member 738*h* comprises a first wall 705*c*, 705*h* located between the inner wall 710 and the first tube (e.g., 742*h*). The first retention member 738*h* can comprise a second wall 707*c*, 707*h* located between the first tube and the medicine storage area (e.g., 750).

In several embodiments, the first retention member comprises a first hoop 709*c* and a second hoop 709*c*. The first tube can be located at least partially in the first hoop. The second tube can be located at least partially in the second hoop.

Referring now to FIGS. 4-56 and 69-79, in some embodiments, retention members (e.g., 736, 738, 738*b*, 738*c*, 738*d*, 738*e*, 738*f*, 738*h*, 753, 781) can deform to fit through a narrow opening of the insulated container. Once inside the insulated container, the retention members can spring back to a larger shape (than could fit through the opening without deformation). The first retention member can comprise a maximum diameter measured radially outward relative to the central axis. The opening can comprise a minimum diameter measured radially outward relative to the central axis. The maximum diameter of the first retention member can be larger than the minimum diameter of the opening. The first retention member can be configured to change shape in a reversible manner to reduce the maximum diameter to enable inserting the first retention member through the opening. The first retention member can be configured to return to a shape having the maximum diameter after the first retention member has passed through the opening.

In several embodiments, the first tube comprises a first cylindrical portion at least partially filled with the first phase change material, and the second tube comprises a second cylindrical portion at least partially filled with the second phase change material. The first tube can be oriented parallel to the central axis, and the second tube can be oriented parallel to the central axis.

Referring now to FIGS. 31-37 and 49-54, in some embodiments, the first tube comprises outer dimensions characterized by a thickness and a width. The first tube has a maximum thickness measured in a direction radially outward from the central axis of the insulated container. The first tube comprises a maximum width measured perpendicular to the maximum thickness and perpendicular to the central axis. In several embodiments, the maximum width is at least two times larger than the maximum thickness.

Referring now to FIGS. 31-37, the first tube can be a portion of a wedge shape (e.g., with rounded edges). This shape can help fit several tubes around a perimeter of a circle or oval shaped medicine storage area.

The tube can include a lid configured to cover an opening to the tube. The lid can be laser welded to the tube. The lid can be coupled to the tube using processes used to attach lids to aluminum soda cans and/or processes used to attach lids to "tin cans" (which can be made from steel, aluminum, tin, or any other suitable metal).

Figure 31:
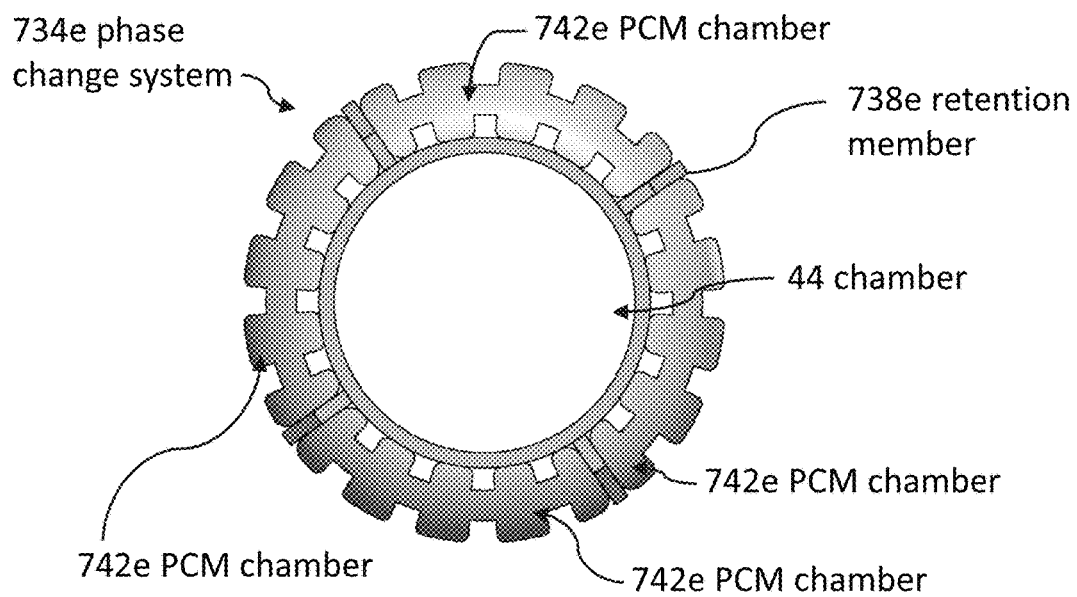
FIG. 31 illustrates a bottom view of a phase change system that includes a retention member that has radially outward protrusions that separate containers having PCM chambers, according to some embodiments.

In some embodiments, the first tube comprises at least one of fins, valleys, and detents (e.g., as shown in FIG. 31) configured increase a surface area of the first tube to promote heat transfer. The first retention member can comprise ventilation channels configured to enable airflow between the medicine storage area and the phase change system.

Figure 49:
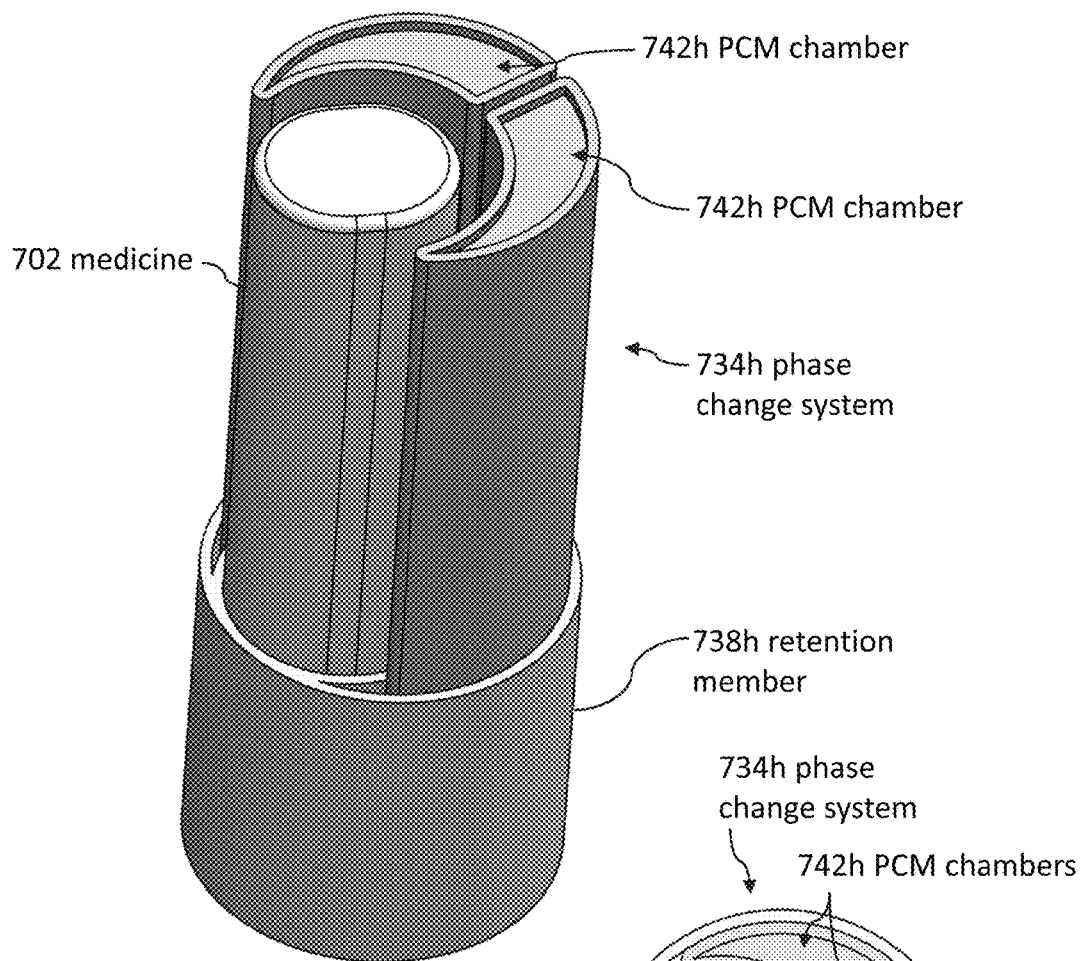
FIG. 49 illustrates a perspective view of a phase change system that has a radially offset cavity to hold medicine, according to some embodiments.
Figure 50:
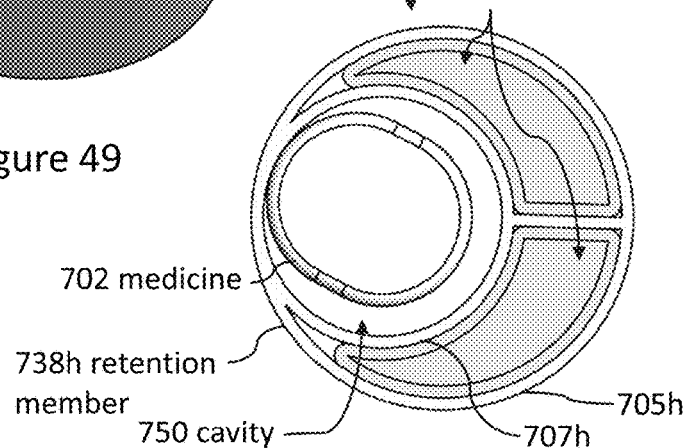
FIG. 50 illustrates a top view of the phase change system shown in FIG. 49, according to some embodiments.

Referring now to FIGS. 49-54, in several embodiments, the insulated container comprises a first central axis, the first tube comprises a second central axis, the second tube comprises a third central axis, and the medicine comprises a fourth central axis. The first retention member can orient the second, third, and fourth central axes within 30 degrees of parallel to the first central axis of the insulated container (e.g., as shown in FIG. 49-52). The second, third, and fourth central axes can be located radially outward relative to the first central axis of the insulated container (e.g., as shown in FIG. 50 where the retention member 738*h* is concentric with the central axis of the insulated container shown in FIGS. 51 and 52).

Figure 52:
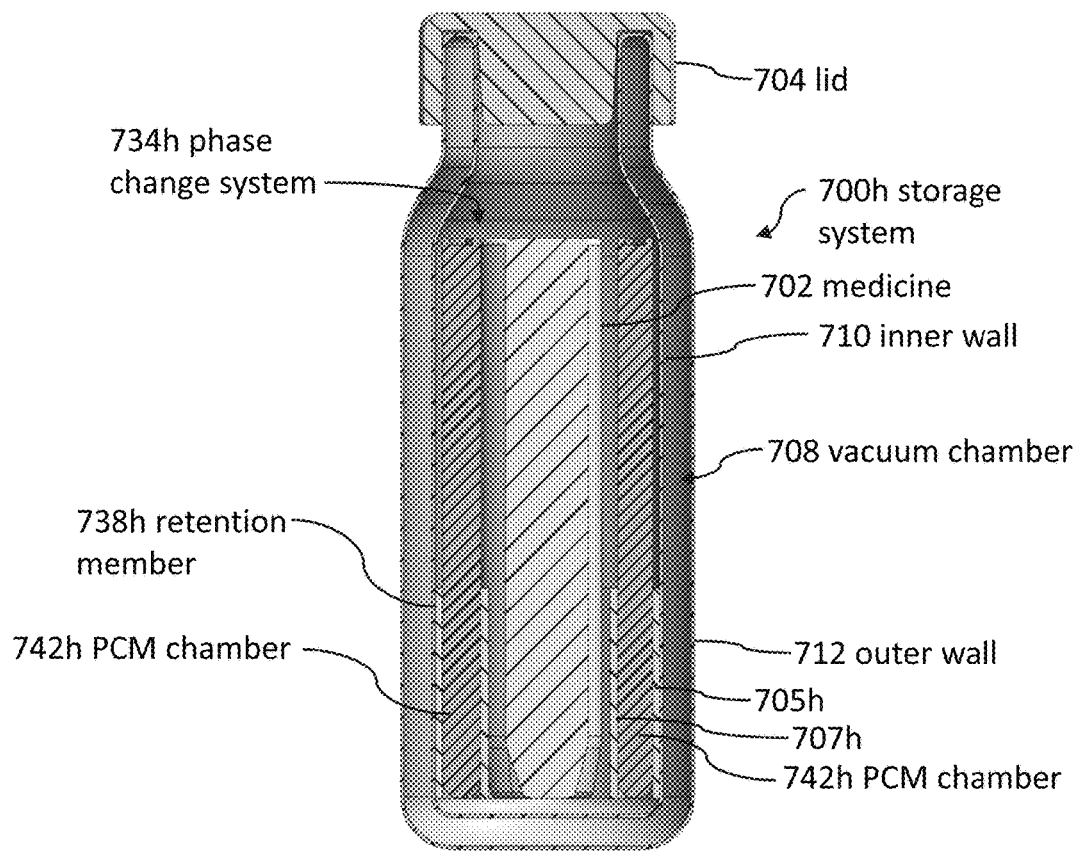
FIG. 52 illustrates a cross-sectional view taken along line 52-52 in FIG. 51, according to some embodiments.

In some embodiments, the first tube comprises a cross section that is perpendicular to the second central axis. As shown in FIG. 52, the cross section can have three outermost points 711 that form a triangle. Walls 713 of the first tube that connect the three outermost points 711 can be at least one of straight and curved. As shown in FIG. 52, the tubes are a portion of a crescent shape. The tubes have a cross section that is a portion of a crescent shape.

Figure 23:
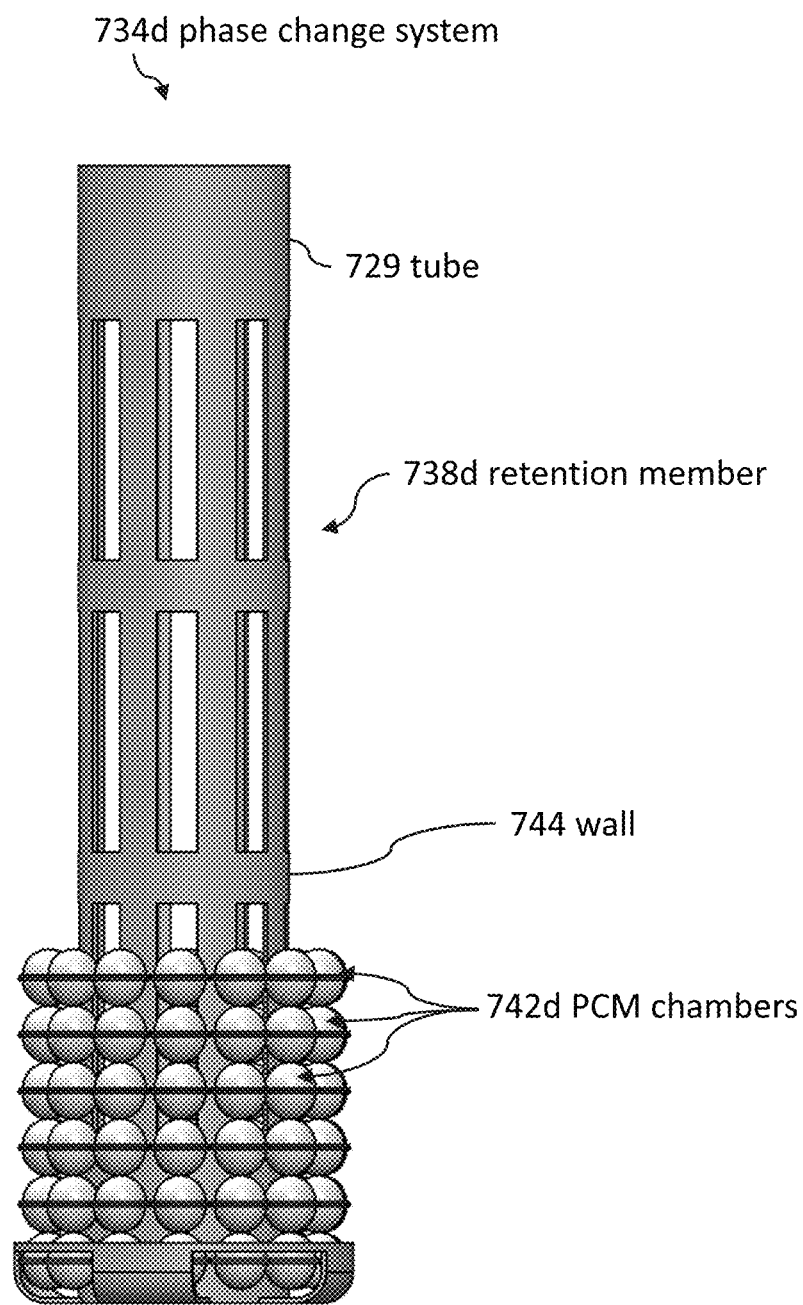
FIG. 23 illustrates a side view of a phase change system that includes a retention member and dome-shaped PCM chambers, according to some embodiments.

FIG. 23 illustrates a side view of a phase change system 734*d* that includes a retention member 738*d* (which includes a tube 729) and dome-shaped PCM chambers 742*d*. In some embodiments, the PCM-chambers 742*d* are MicroVesls (a spherical container having a multi-layer polymer structure) made by Vesl, LLC. The dome-shaped PCM chambers 742*d* can include fins, ridges, detents, and/or valleys configured to increase the surface area of the PCM chambers 742*d* to promote rapid heat transfer from the PCMs to the medicine.

Figure 24:
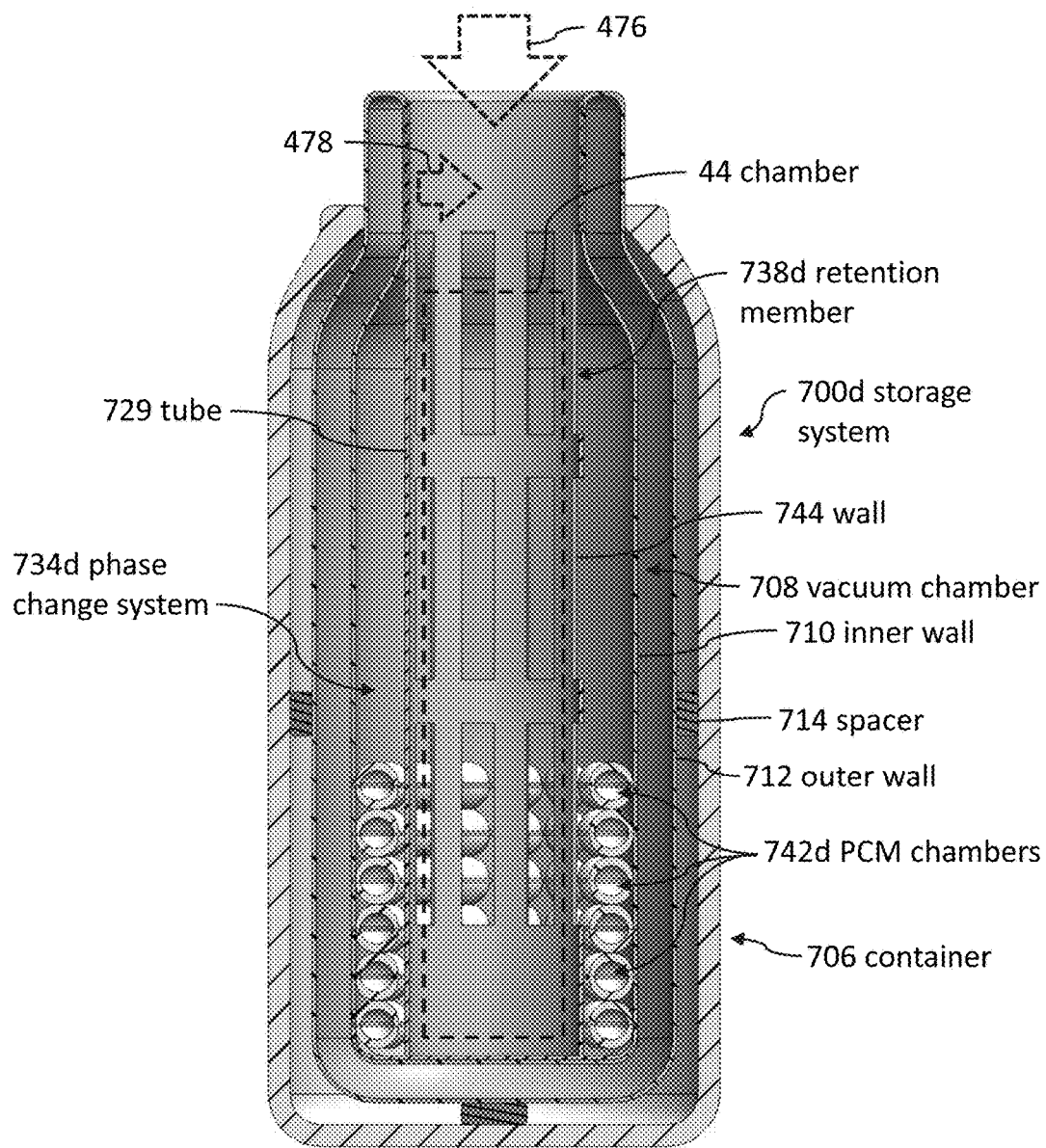
FIG. 24 illustrates the same cross section as FIG. 3 except that a phase change system is shown, according to some embodiments.

FIG. 24 illustrates the same cross section as FIG. 3 except that the phase change system 734*d* is shown. The dome-shaped PCM chambers 742*d* are located (e.g., captured) between a wall 744 of the retention member 738*d* and the inner wall 710 of the vacuum chamber 708. Many embodiments include more PCM chambers 742*d* than are shown in FIG. 24. (Not all of the PCM chambers 742*d* are labeled in the figures.) An inner portion of the retention member 738*d* is a chamber 44 to hold the medicine 702 (shown in FIG. 1).

The retention member 738*d* can be more flexible than the containers that form the PCM chambers 742*d* such that a proximal portion of the retention member 738*d* in the neck area of the storage system 700*d* can elastically deform radially inward (as shown by arrow 478). When the proximal portion of the retention member 738*d* is deformed radially inward, the PCM chambers 742*d* can be inserted in the area between the wall 744 (of the retention member 738*d*) and the vacuum chamber 708. The PCM chambers 742*d* can be free to move relative to each other (e.g., "rattle around").

Figure 25:
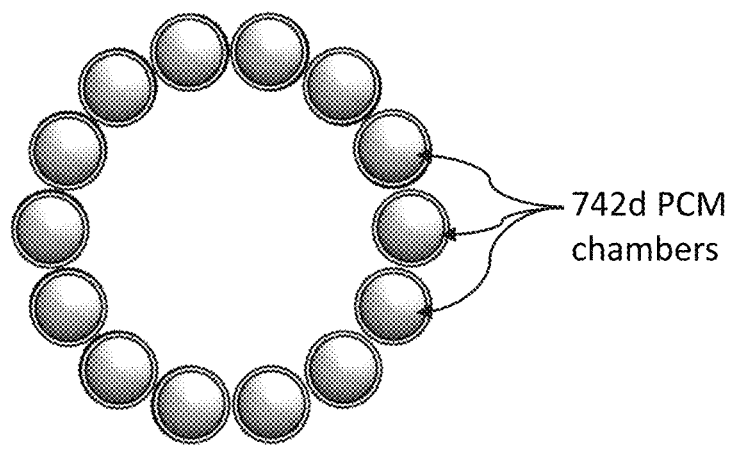
FIG. 25 illustrates a top view of dome-shaped PCM chambers, according to some embodiments.
Figure 26:
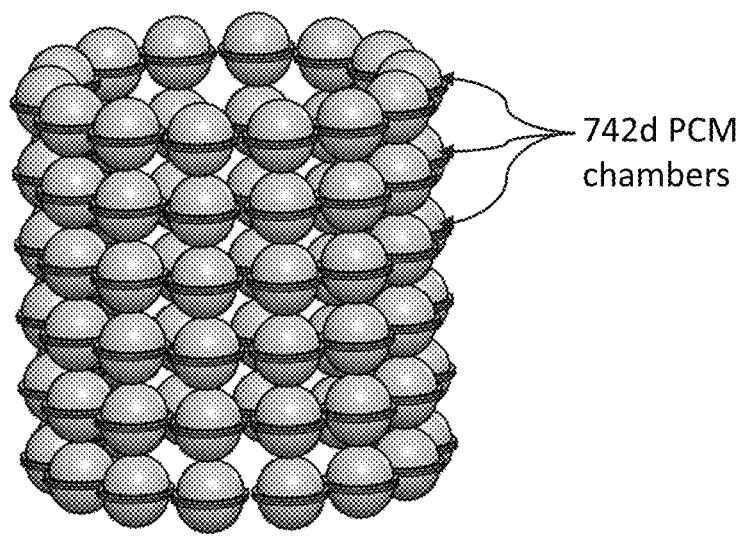
FIG. 26 illustrates a perspective view of many PCM chambers, according to some embodiments.
Figure 27:
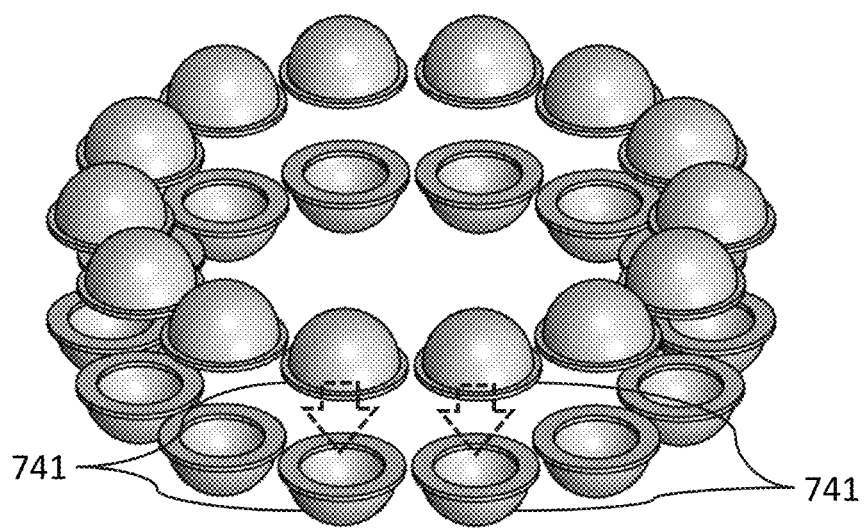
FIG. 27 illustrates dome-shaped PCM chambers prior to each half of each PCM chamber being coupled together, according to some embodiments.

FIG. 25 illustrates a top view of dome-shaped PCM chambers 742*d*. FIG. 26 illustrates a perspective view of many PCM chambers 742*d*. FIG. 27 illustrates the dome-shaped PCM chambers 742*d* prior to each half 741 of each PCM chamber 742*d* being coupled together (as indicated by the arrows in FIG. 27). Each PCM chamber 742*d* can be filled with PCM. Then, the two sides of the PCM chamber 742*d* can be coupled together (e.g., via a heating process).

Figure 28:
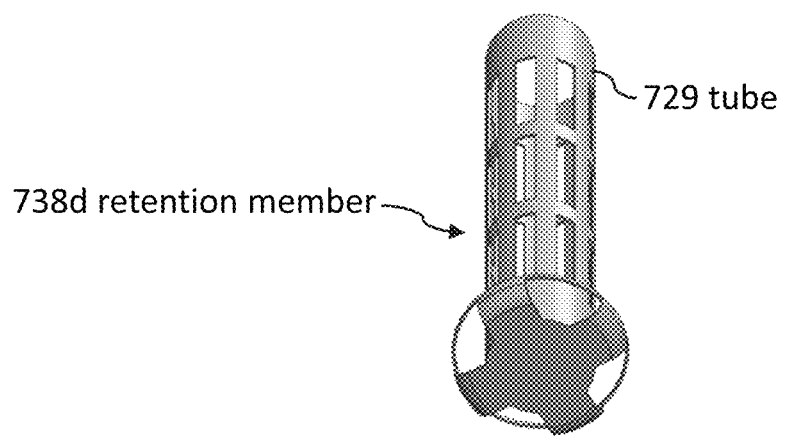
FIGS. 28-30 illustrate various perspective views of a retention member having a tube, according to some embodiments.
Figure 29:
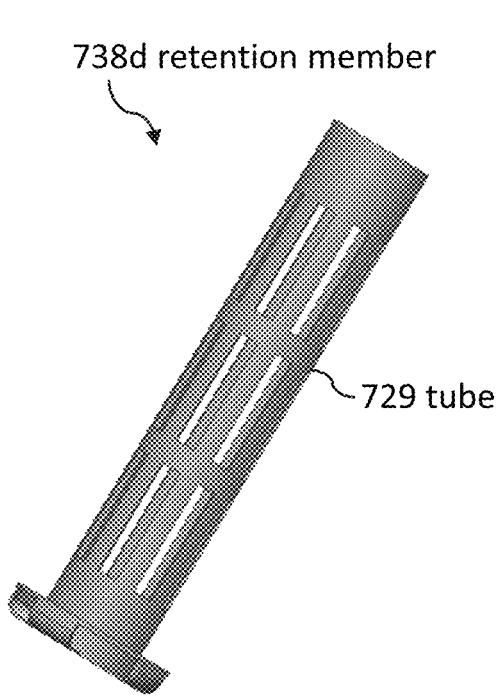
Figure 30:
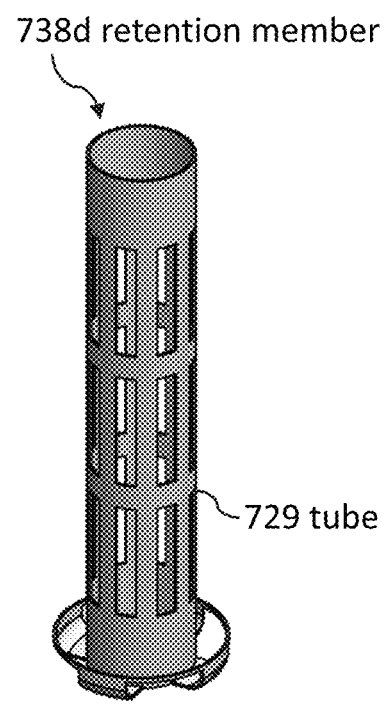

FIGS. 28-30 illustrate various perspective views of the retention member 738*d*. A distal portion of the retention member 738*d* can be wider than the neck's width 724 (shown in FIG. 3), but can be flexible to enable elastic deformation. This elastic deformation permits the distal portion of the retention member 738*d* to move through the neck 722 (shown in FIG. 3) and then spring radially outward to a width that is wider than the width 724 of the neck 722.

Figure 67:
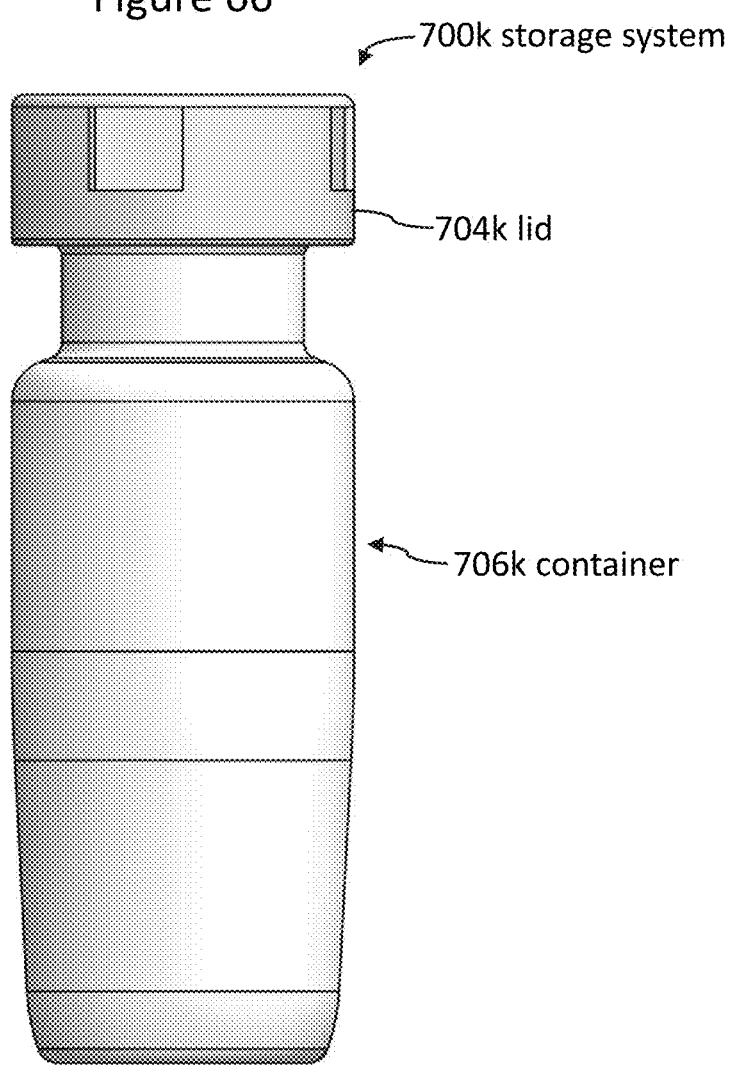
FIGS. 67 and 68 illustrate side views of a storage system, according to some embodiments.

Referring now to FIGS. 23-30, in several embodiments, a medicine storage system 700*d* comprises an insulated container 706 having an opening; a first lid 704, 704*k* (shown in FIGS. 3 and 67) configured to cover the opening; a phase change system 734*d* located inside the insulated container; a medicine storage area (e.g., 44) located inside the insulated container; and a first retention member 738*d* located inside the insulated container 706 and configured to prevent the phase change system 734*d* from blocking access to the medicine storage area. For example, if the PCM chambers 742*d* fall into the medicine storage area, the PCM chambers 742*d* can block a user from inserting the medicine into the medicine storage area (which can be a cavity inside the tube 729). As shown in FIG. 24, the storage system 700*d* can be configured to provide access for inserting a medicine through the opening and into the medicine storage area.

The spheres shown in FIG. 25 are containers that form PCM chambers 742*d*. The phase change system 734*d* (shown in FIGS. 23 and 24) comprises a first container having a first phase change material and a second container having a second phase change material. The first and second containers can be spherical, cylindrical, or any other suitable shape. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

In some embodiments, the first retention member comprises a tube 729 located inside the insulated container 706 such that the tube 729 is in fluid communication with the opening. The storage system 700*d* can be configured to enable inserting the medicine through the opening and into the tube 729. The tube 729 can extend from a distal portion of the insulated container 706 to a proximal portion of the insulated container 706. The first and second containers can be located between an inner wall 710 of the insulated container and an outer wall of the tube 729.

In several embodiments, the storage system further comprises a plurality of containers at least partially filled with at least one of the first phase change material and the second phase change material. As shown in FIGS. 23, 24, and 26, the plurality of containers are not coupled to each other such that the plurality of containers are movable within an area between the inner wall 710 of the insulated container and the outer wall of the tube 729.

FIG. 31 illustrates a bottom view of a phase change system 734e that includes a retention member 738e that has radially outward protrusions that separate containers having PCM chambers 742e. The containers having PCM chambers 742e can include fins, valleys, detents, and other features to increase the surface area of the PCM chambers 742e (to promote heat transfer).

Figure 33:
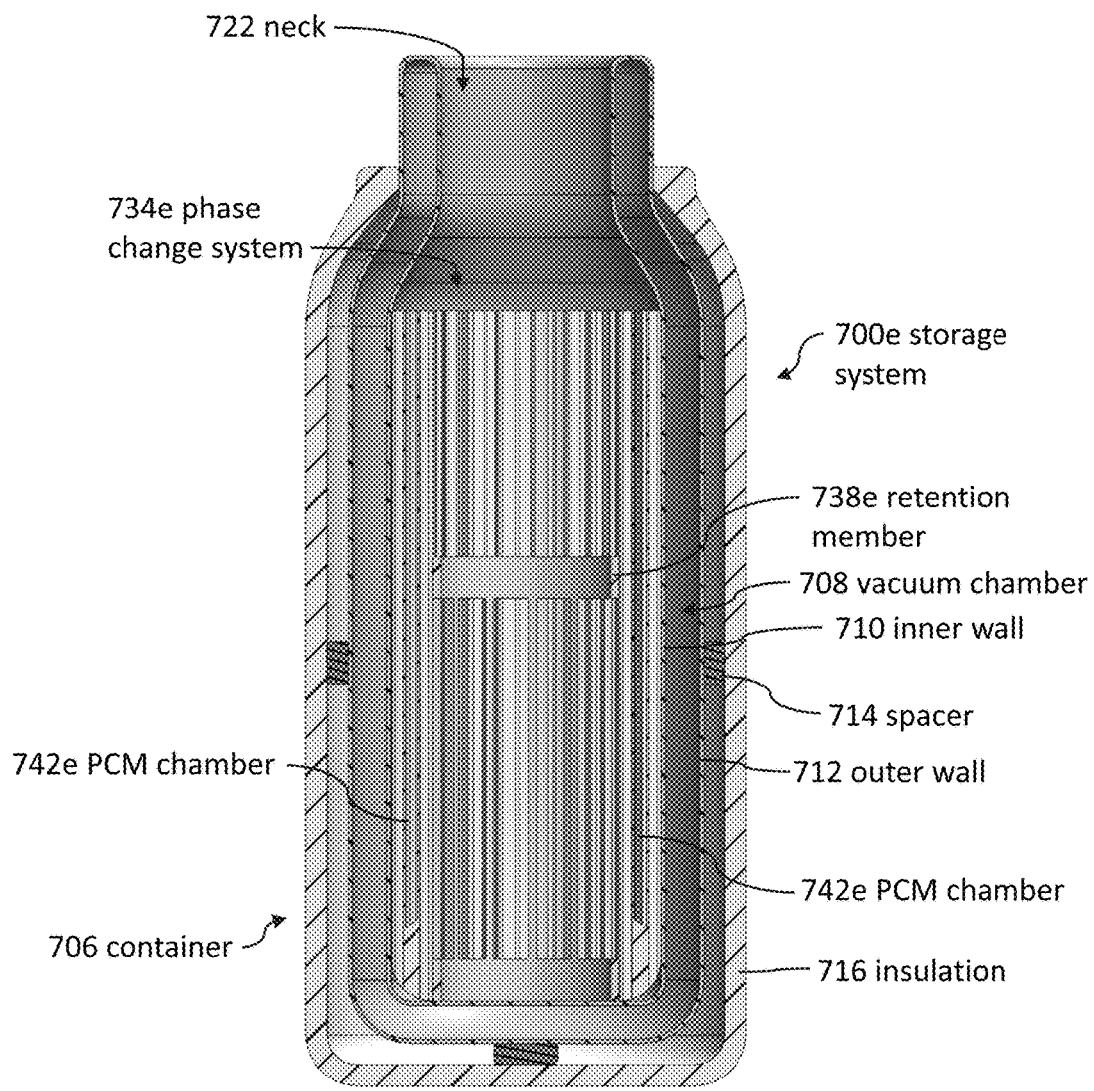
FIG. 33 illustrates the same cross section as FIG. 3 except that a phase change system is shown and the lid is hidden, according to some embodiments.

The retention member 738e can be more flexible than the containers having PCM chambers 742e to enable the retention member 738e to deform during insertion of the containers having PCM chambers 742e through the neck 722 and into an interior portion of the storage system 700e (shown in FIG. 33). In some embodiments, the containers having PCM chambers 742e are flexible to enable the PCM chambers 742e to deform during insertion of the containers having PCM chambers 742e through the neck 722 and into an interior portion of the storage system 700e.

Figure 32:
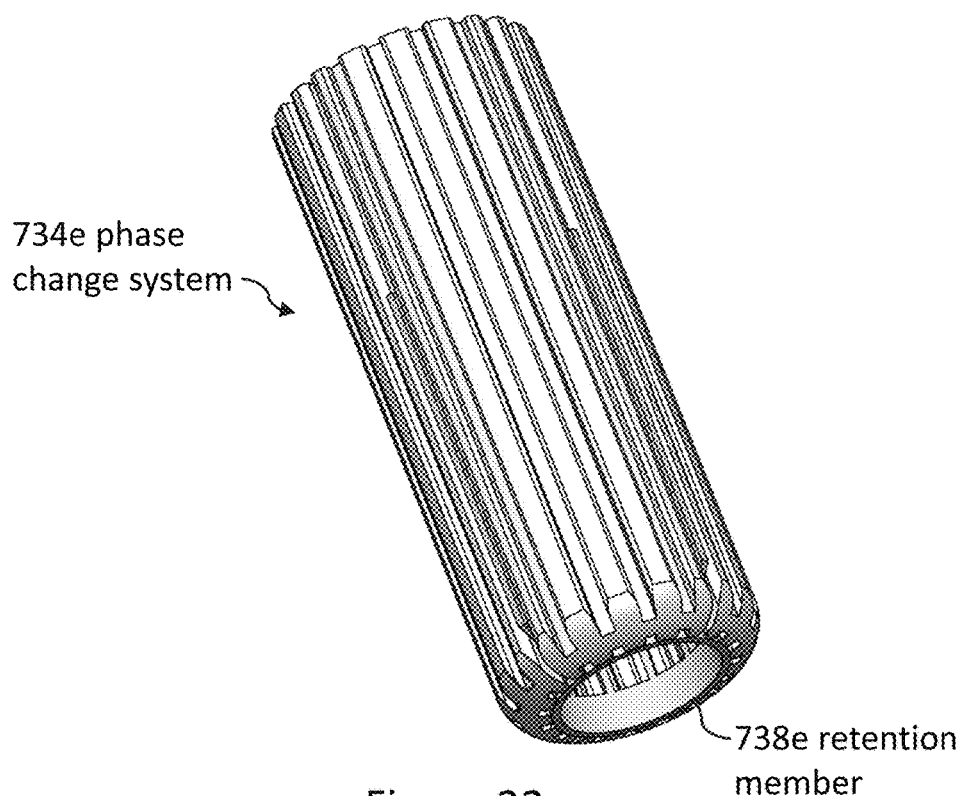
FIG. 32 illustrates a perspective view of a phase change system, according to some embodiments.

FIG. 32 illustrates a perspective view of the phase change system 734e. FIG. 33 illustrates the same cross section as FIG. 3 except that the phase change system 734e is shown and the lid 704 is hidden. The embodiment shown in FIG. 33 can use the lid 704k shown in FIGS. 66, 69, 70, and 75-78.

Figure 34:
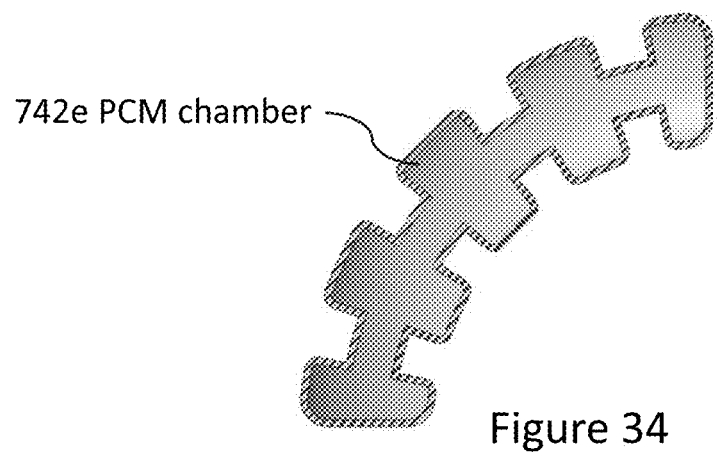
FIG. 34 illustrates a cross-sectional view taken along line 34-34 from FIG. 35, according to some embodiments.
Figure 35:
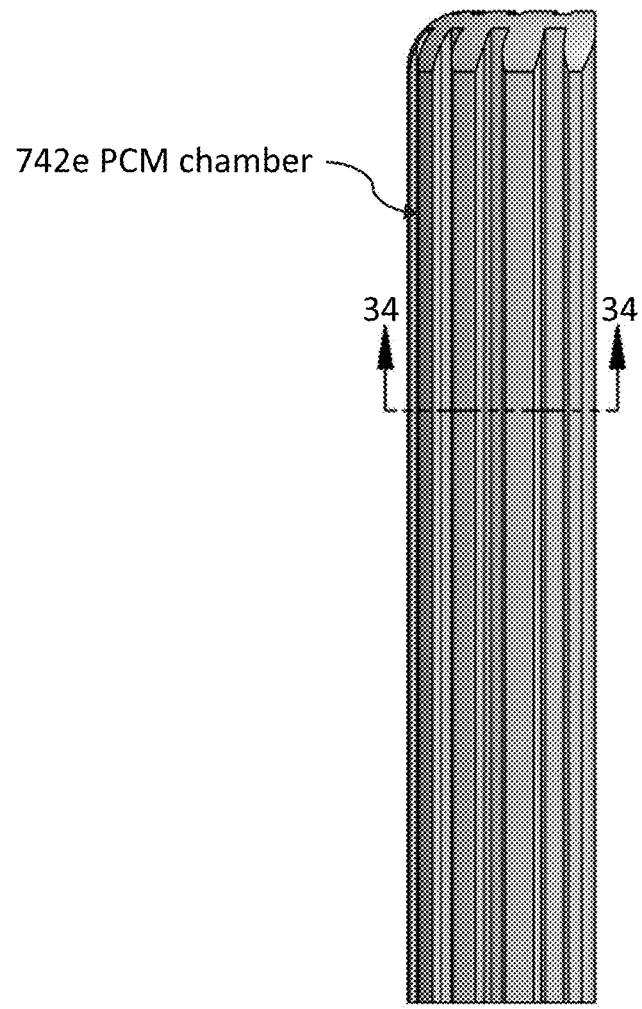
FIG. 35 illustrates a side view of a container having a PCM chamber, according to some embodiments.
Figure 36:
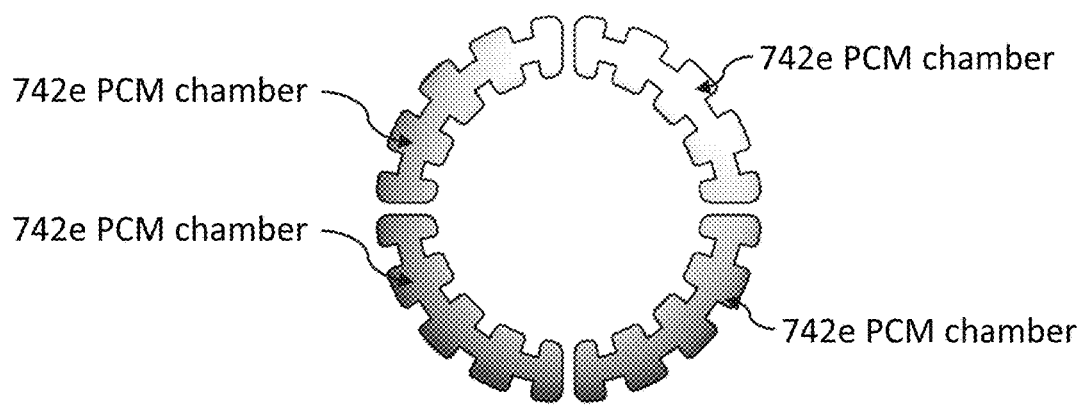
FIG. 36 illustrates a bottom view of four containers, according to some embodiments.
Figure 37:
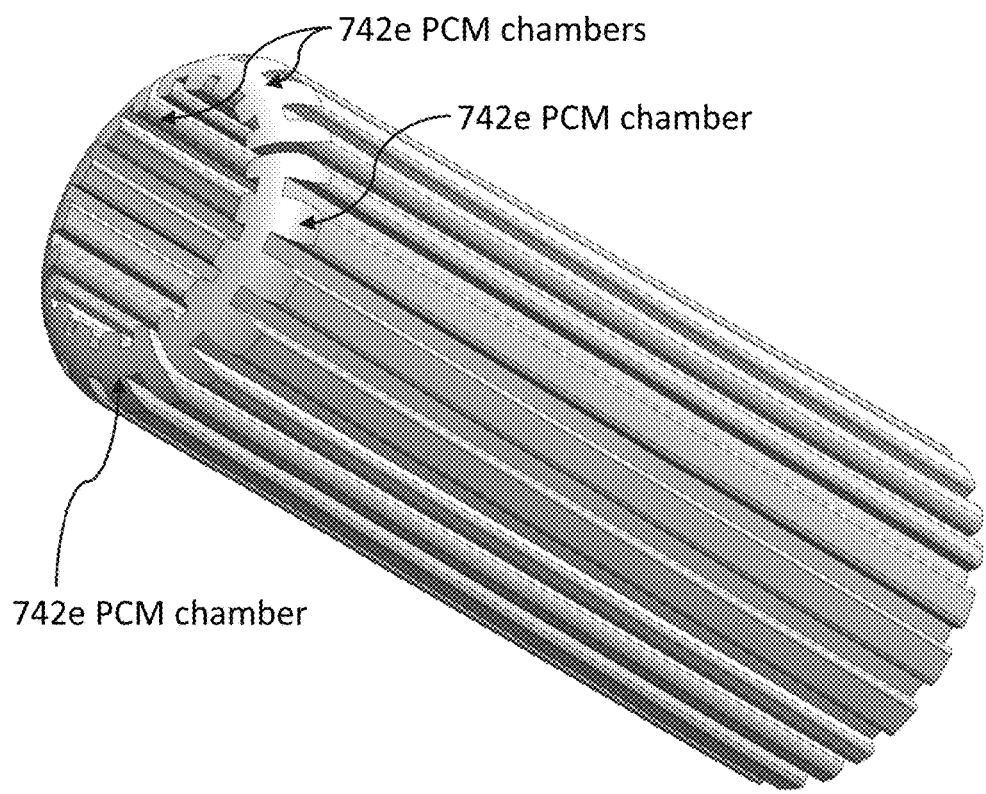
FIG. 37 illustrates a perspective view of containers shown in FIG. 36, according to some embodiments.
Figure 38:
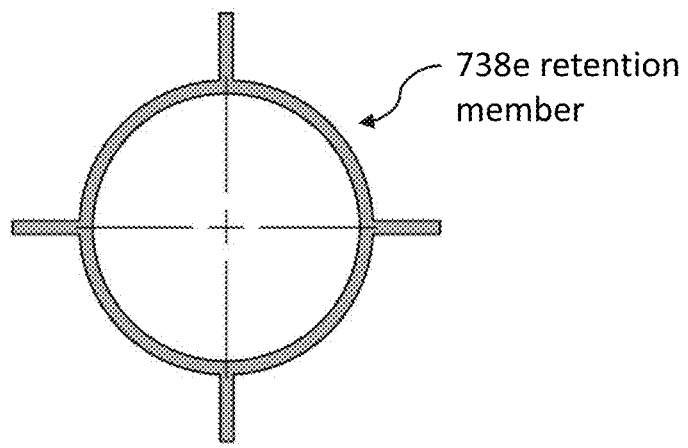
FIG. 38 illustrates a top view of a retention member, according to some embodiments.
Figure 39:
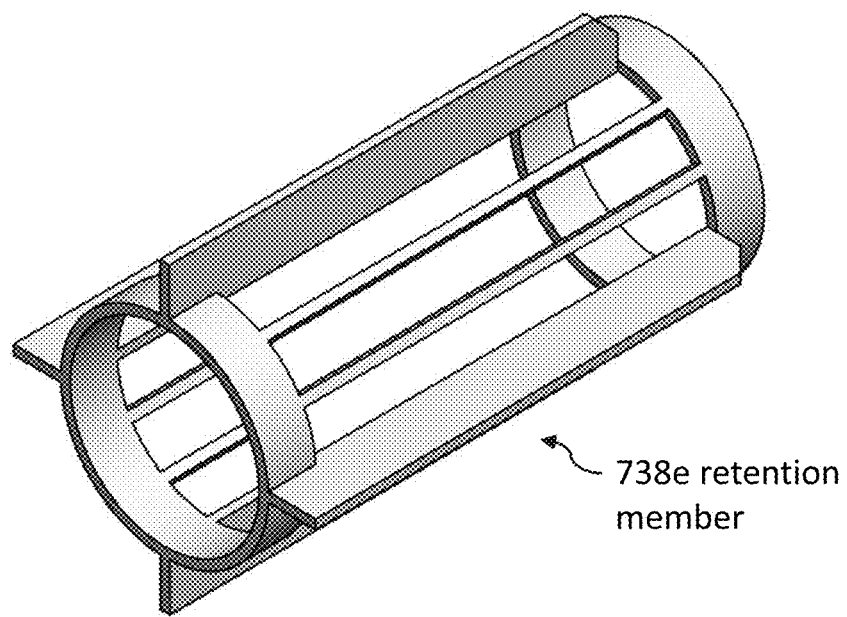
FIG. 39 illustrates a perspective view of a retention member, according to some embodiments.

FIG. 34 illustrates a cross-sectional view taken along line 34-34 from FIG. 35. FIG. 34 shows that the surface area is increased by the surface features of the container having the PCM chamber 742e. FIG. 35 illustrates a side view of the container having the PCM chamber 742e. FIG. 36 illustrates a bottom view of four containers. Each container has at least one PCM chamber 742e. FIG. 37 illustrates a perspective view of the containers shown in FIG. 36. FIG. 38 illustrates a top view of the retention member 738e shown in FIGS. 31-33. FIG. 39 illustrates a perspective view of the retention member 738e.

Figure 40:
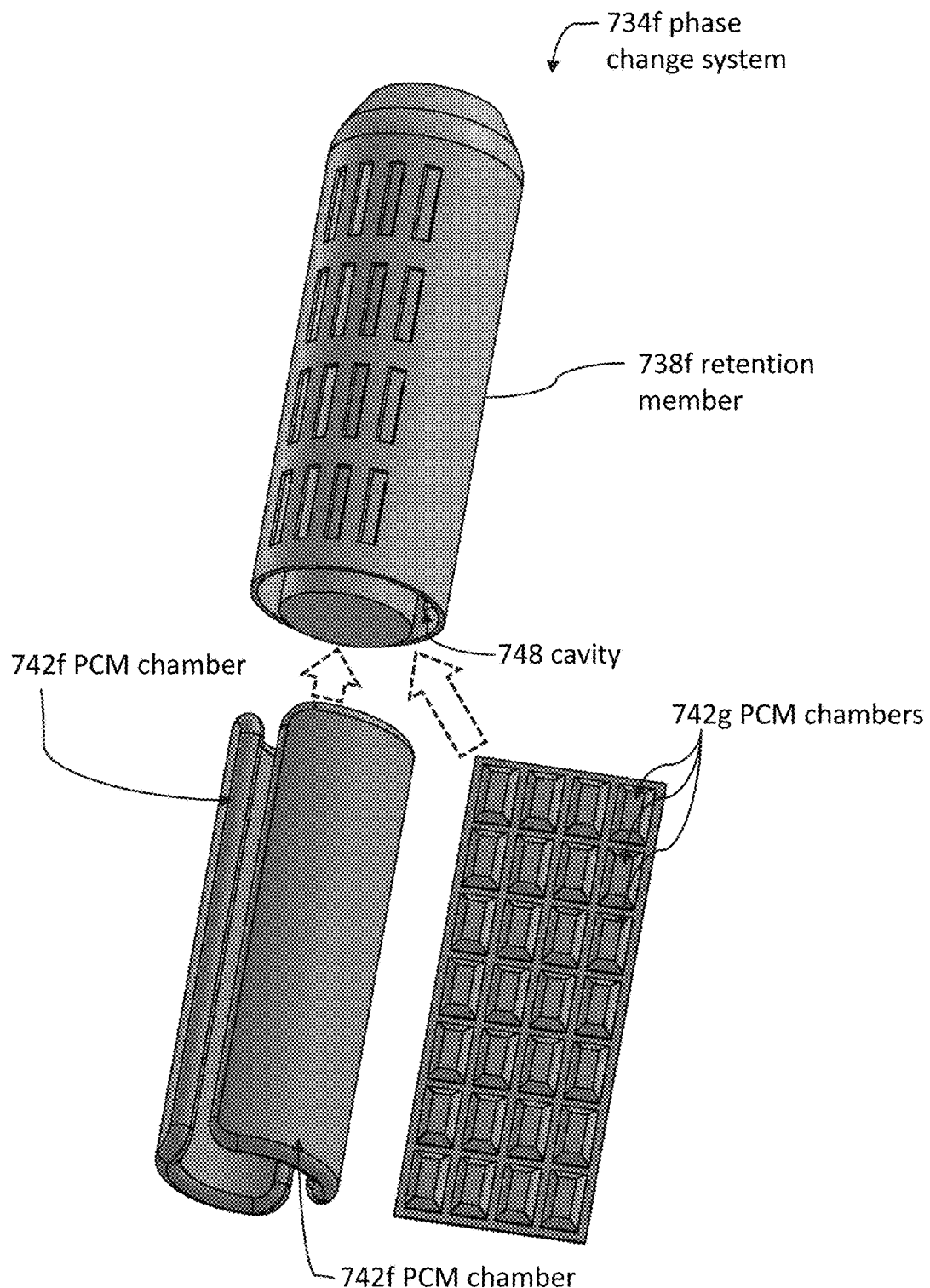
FIG. 40 illustrates a perspective view of a phase change system that includes a tubular retention member that has holes to promote airflow and heat transfer from an area having the medicine to an area having the PCM chambers, according to some embodiments.
Figure 41:
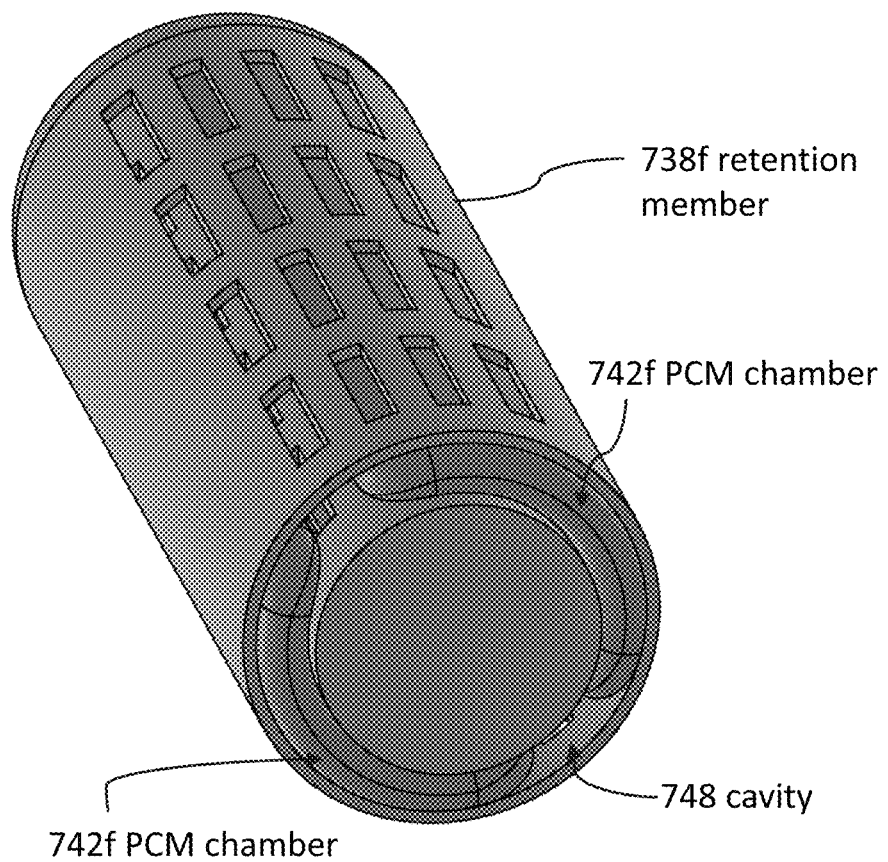
FIG. 41 illustrates a perspective view of a bag filled with PCM and inserted into a cavity of a retention member, according to some embodiments.
Figure 42:
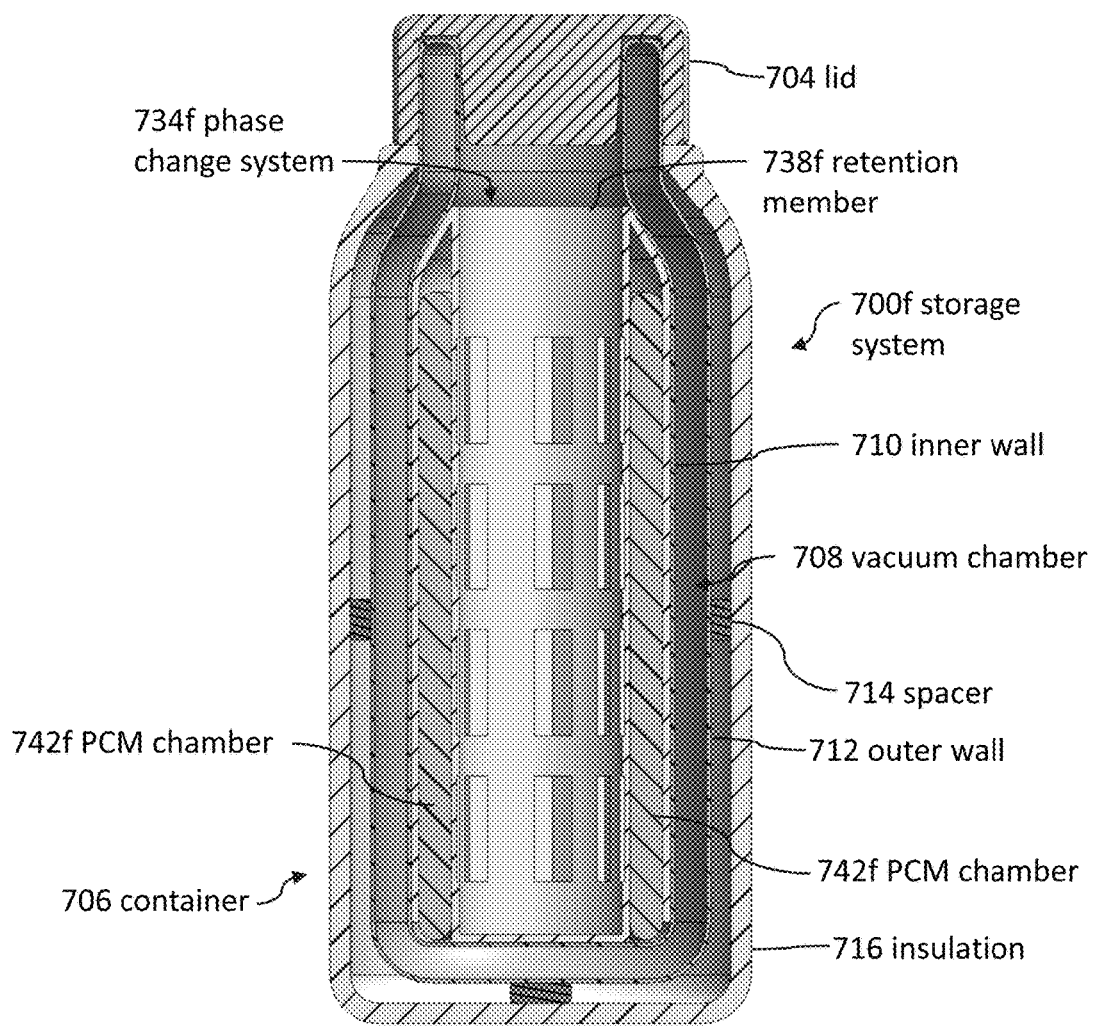
FIG. 42 illustrates the same cross section as FIG. 3 except that a phase change system is shown, according to some embodiments.

FIG. 40 illustrates a perspective view of a phase change system 734f that includes a retention member 738f that has holes to promote airflow and heat transfer from an area having the medicine 702 (shown in FIG. 3) to an area having the PCM chambers 742f and/or the PCM chambers 742g. The PCM chambers 742f and/or the PCM chambers 742g can fit inside a cavity 748 of the retention member 738f (e.g., as shown in FIGS. 41 and 42).

The PCM chamber 742f can be a highly flexible pouch made from multiple layered film, filled with PCM, and hermetically sealed to prevent leakage or intrusion (e.g., a PackVesl made by Vesl, LLC). The PCM chamber 742g can be a highly-flexible, multi-layer barrier film sheet having blisters filled with PCM and hermetically sealed to prevent leakage or intrusion (e.g., a MatVesl made by Vesl, LLC).

The PCM chamber 742g can be any suitable dimension. In some embodiments, each pouch (e.g., each PCM chamber 742g) can have a width of at least 15 millimeters and/or less than 45 millimeters. In some embodiments, each pouch (e.g., each PCM chamber 742g) can have a length of at least 30 millimeters, less than 80 millimeters, and/or less than 200 millimeters.

The PCM chamber 742f can be much larger than the PCM chamber 742g. In embodiments, the PCM chamber 742f has a width of at least 40 millimeters and/or less than 150 millimeters. In several embodiments, the PCM chamber 742f has a length of at least 80 millimeters and/or less than 200 millimeters.

FIG. 41 illustrates a perspective view of a pouch filled with PCM inserted into a cavity 748 of the retention member 738f. The PCM chambers 742f, 742g shown in FIG. 40 can be inserted into the cavity 748 as shown in FIG. 41.

Figure 46:
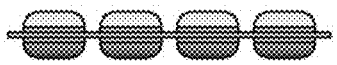
FIGS. 46-48 illustrate various views of PCM chambers made from a highly-flexible, multi-layer barrier film sheet having blister-style bags filled with PCM and hermetically sealed to prevent leakage or intrusion, according to some embodiments.
Figure 47:
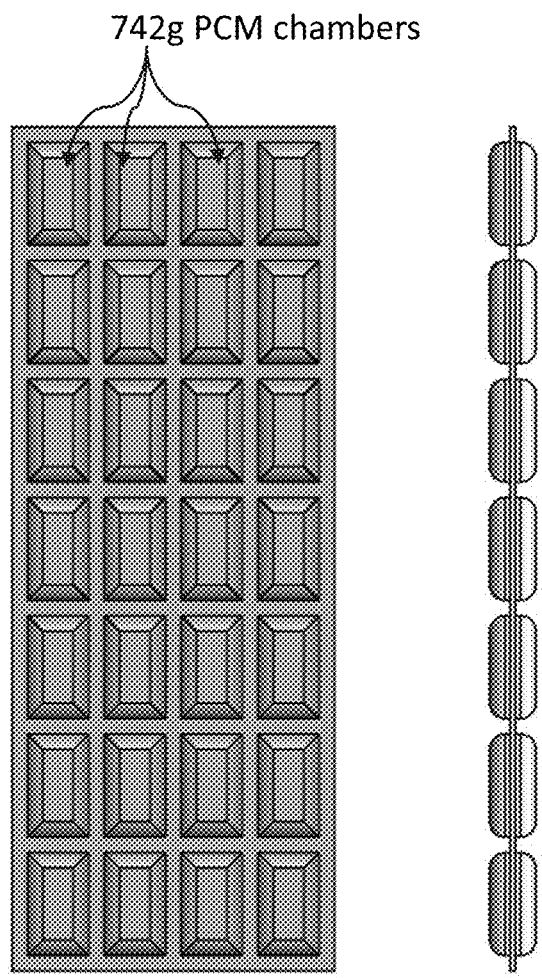
Figure 48:

FIG. 42 illustrates the same cross section as FIG. 3 except that the phase change system 734f is shown. FIGS. 43-45 illustrate various views of the retention member 738f. FIGS. 46-48 illustrate various views of PCM chambers 742g made from a highly-flexible, multi-layer barrier film sheet having blisters filled with PCM and hermetically sealed to prevent leakage or intrusion (e.g., a MatVesl made by Vesl, LLC).

Referring now to FIG. 47, some of the chambers 742g can be filled with a first PCM and some of the chambers 742g can be filled with a second PCM that has a different melting temperature than the melting temperature of the first PCM. In several embodiments, some of the chambers 742g are filled with PureTemp 18 (having a melting temperature of approximately 18 degrees Celsius) and some of the chambers 742g are filled with PureTemp 28 (having a melting temperature of approximately 28 degrees Celsius). Thus, one flexible sheet can contain pouches having two different types of PCMs that are fluidly isolated from each other but are mechanically coupled.

At least one of the PCMs can be colored (e.g., via a dye) to help people visually differentiate one PCM type having a first color from another PCM type having a second color. Thus, factory workers can see what type of PCM is located in a chamber 742g of a clear pouch.

Referring now to FIG. 40, several embodiments include a first flexible sheet with PCM chambers 742g (e.g., having a first PCM type) and include a second flexible sheet with PCM chambers 742g (e.g., having a second PCM type). Both flexible sheets can be held in place by a retention member 738f such that the flexible sheets are located at least partially between the retention member 738f and an inner wall 710 of a vacuum flask (e.g., as shown in FIG. 42).

FIG. 49 illustrates a perspective view of a phase change system 734h that has an offset hole to hold the medicine 702. FIG. 50 illustrates a top view of the phase change system 734h shown in FIG. 49. The hole (e.g., a cavity 750) in which at least a portion of the medicine is located is radially offset from a center of the storage system 700h shown in FIG. 52.

Figure 51:
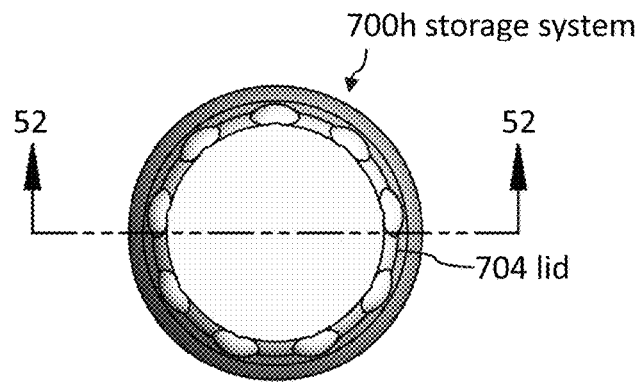
FIG. 51 illustrates a top view of a storage system, according to some embodiments.

FIG. 51 illustrates a top view of the storage system 700h. FIG. 52 illustrates a cross-sectional view taken along line 52-52 in FIG. 51.

Figure 53:
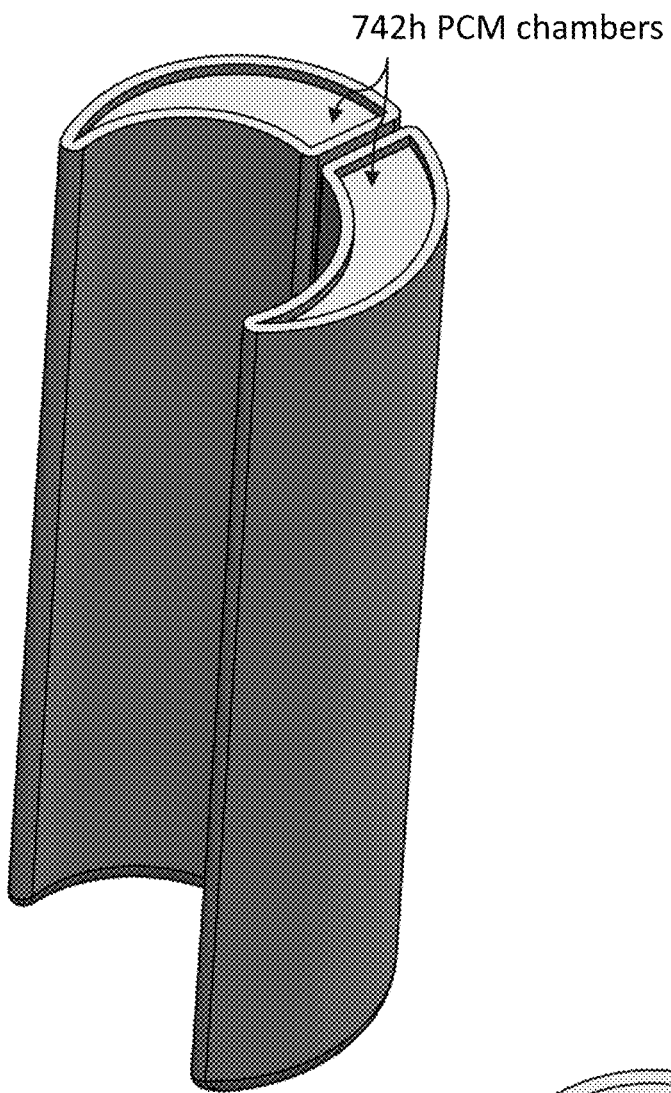
FIG. 53 illustrates a perspective view of two containers, according to some embodiments.
Figure 54:
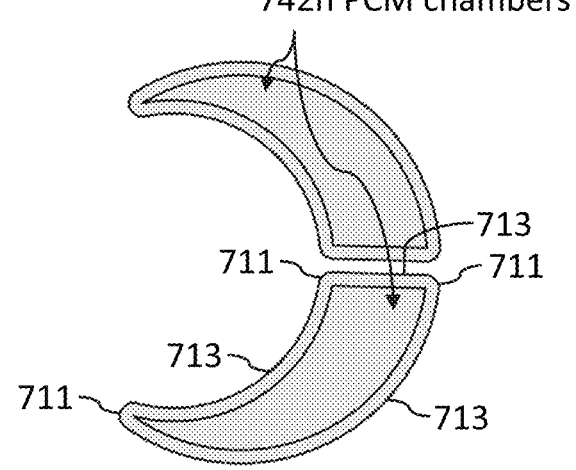
FIG. 54 illustrates a top view of PCM containers, according to some embodiments.
Figure 55:
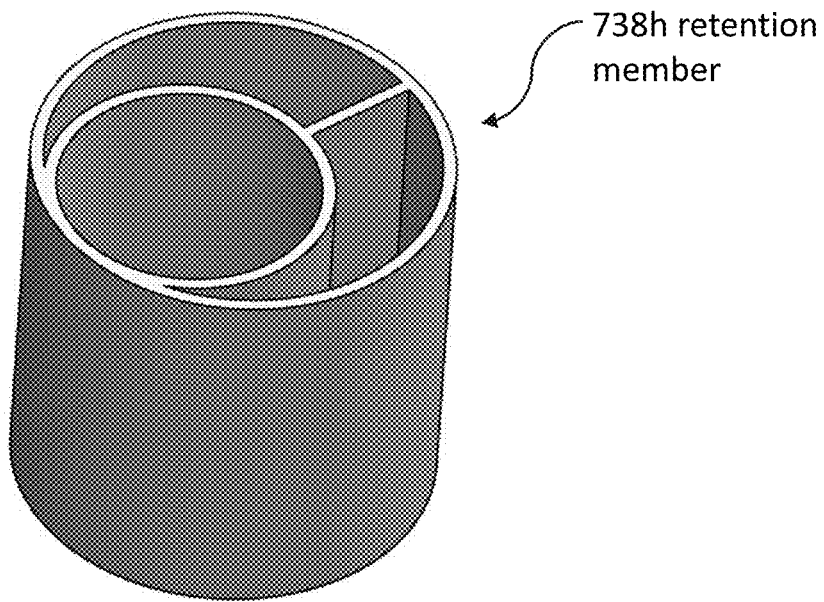
FIG. 55 illustrates a perspective view of a retention member, according to some embodiments.
Figure 56:
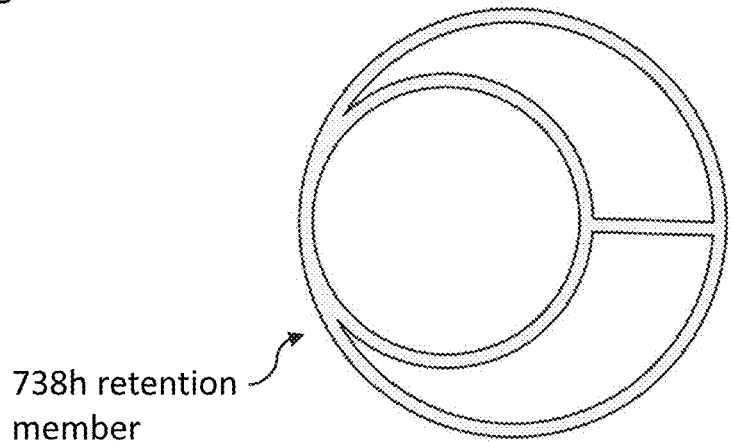
FIG. 56 illustrates a top view of a retention member, according to some embodiments.

FIG. 53 illustrates a perspective view of two containers. Each container includes a PCM chamber 742h. The PCM chambers 742h can have PCMs with the same melting temperature or different melting temperatures. FIG. 54 illustrates a top view of the containers shown in FIG. 53. FIG. 55 illustrates a perspective view of the retention member 738h shown in FIG. 49. FIG. 56 illustrates a top view of the retention member 738h shown in FIG. 49.

Any of the embodiments described herein can include a rigid outer housing or a flexible outer housing. In some cases, people prefer a flexible outer housing. In some cases, people prefer a rigid outer housing.

FIG. 57 illustrates a perspective view of a storage system 700i having a flexible outer housing, which can be made from fabric, rubber, neoprene, urethane, vinyl, nylon, and/or polyester. In some embodiments, the outer housing is thermoplastic polyurethane coated nylon with radio frequency welded seams. The storage system 700i can also include ethylene vinyl acetate foam.

Figure 58:
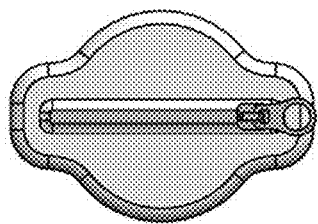
FIG. 58 illustrates a top view of a storage system, according to some embodiments.
Figure 59:
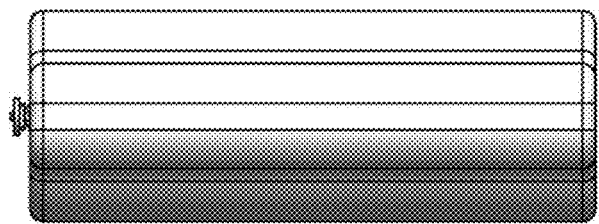
FIG. 59 illustrates a side view of a storage system, according to some embodiments.
Figure 60:
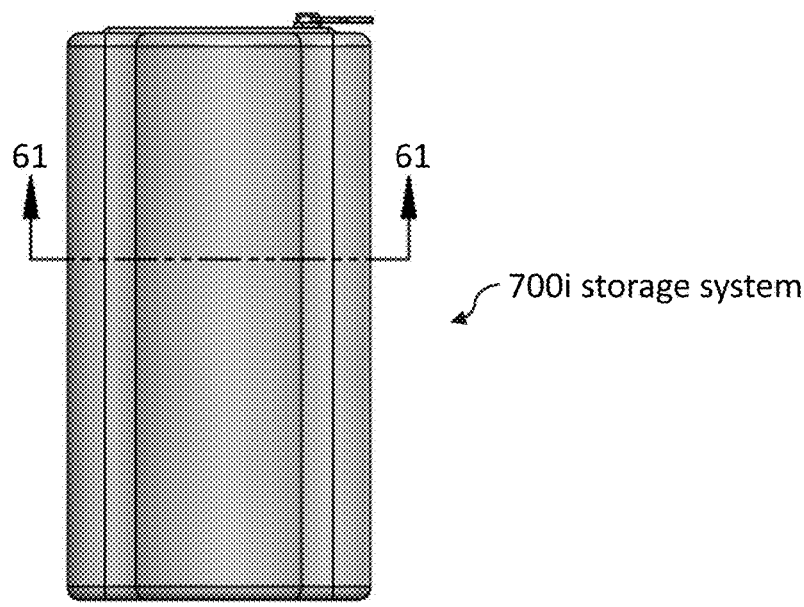
FIG. 60 illustrates a front view of a storage system, according to some embodiments.

The storage system 700i includes a waterproof zipper 746. Opening the zipper 746 provides access to the medicine chamber 44i shown in FIG. 61. FIG. 58 illustrates a top view of the storage system 700i. FIG. 59 illustrates a side view of the storage system 700i. FIG. 60 illustrates a front view of the storage system 700i.

Figure 61:
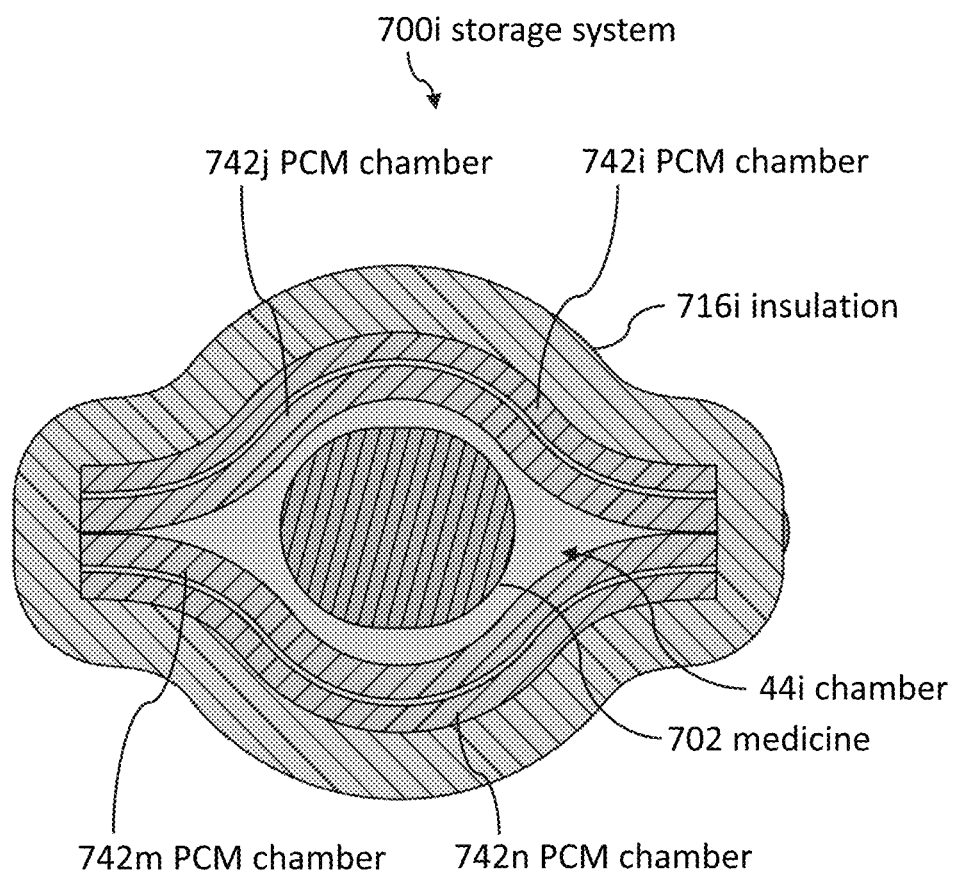
FIG. 61 illustrates a cross-sectional view taken along line 61-61 shown in FIG. 60, according to some embodiments.

FIG. 61 illustrates a cross-sectional view taken along line 61-61 shown in FIG. 60. Embodiments of the storage system 700i can include a first PCM on a first side of the medicine 702 and a second PCM on a second side of the medicine 702. The embodiment shown in FIG. 61 includes PCM in PCM chambers 742j, 742m, which can have lower melting temperatures than PCM in PCM chambers 742i, 742n. PCM in PCM chambers 742j, 742m can have melting temperatures greater than 40 degrees Fahrenheit and less than 74 degrees Fahrenheit. PCM in PCM chambers 742i, 742n can have melting temperatures greater than 74 degrees Fahrenheit and less than 100 degrees Fahrenheit.

PCM in PCM chambers 742i, 742n can be located radially outward from PCM in PCM chambers 742j, 742m such that, at 74 degrees Fahrenheit (e.g., room temperature), the PCM at least partially surrounding the chamber 44i having the medicine 702 is liquid and the PCM located radially outward from the liquid PCM is frozen. In some cases, this configuration is advantageous because the medicine 702 and/or the user's fingers are protected from frozen PCM (which is hard) by liquid PCM (which is comfortably compliant).

Figure 62:
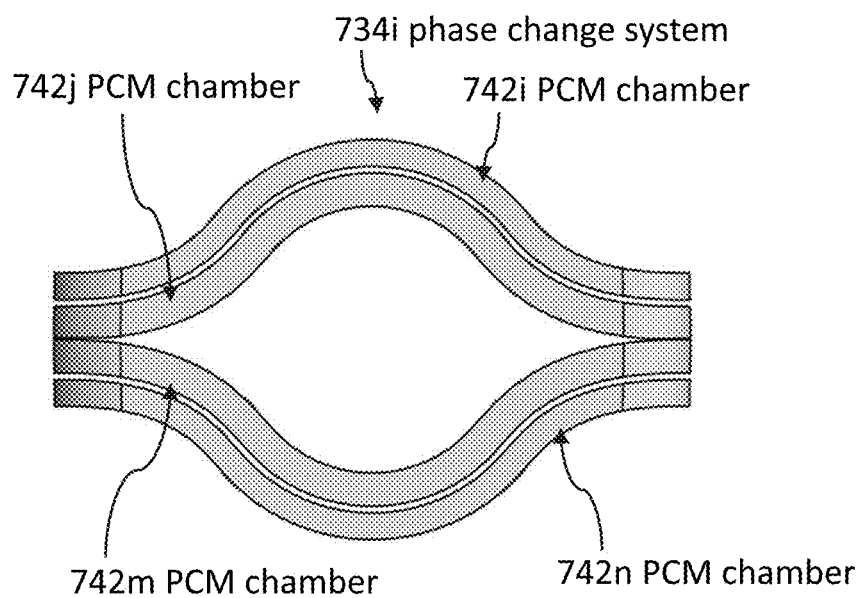
FIG. 62 illustrates a top view of PCM chambers, which can be located in pouches, according to some embodiments.
Figure 63:
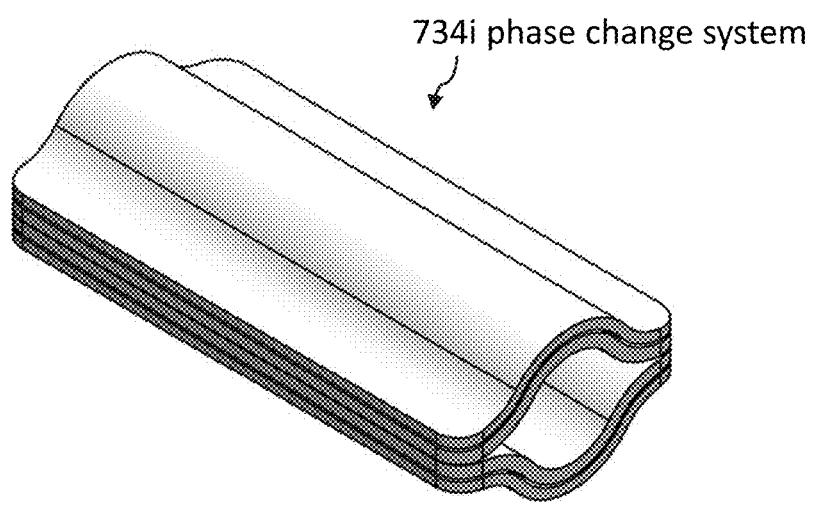
FIG. 63 illustrates a perspective view of a phase change system, according to some embodiments.

FIG. 62 illustrates a top view of the PCM chambers 742i, 742n, 742j, 742m, which can be located in pouches. The pouches can be made from multiple layered film, filled with PCM, and hermetically sealed to prevent leakage or intrusion (e.g., a PackVesl made by Vesl, LLC). The PCM chambers 742i, 742n, 742j, 742m can be formed by a highly-flexible, multi-layer barrier film sheet having blisters filled with PCM and hermetically sealed to prevent leakage or intrusion (e.g., a MatVesl made by Vesl, LLC). FIG. 63 illustrates a perspective view of the phase change system 734i.

Figure 64:
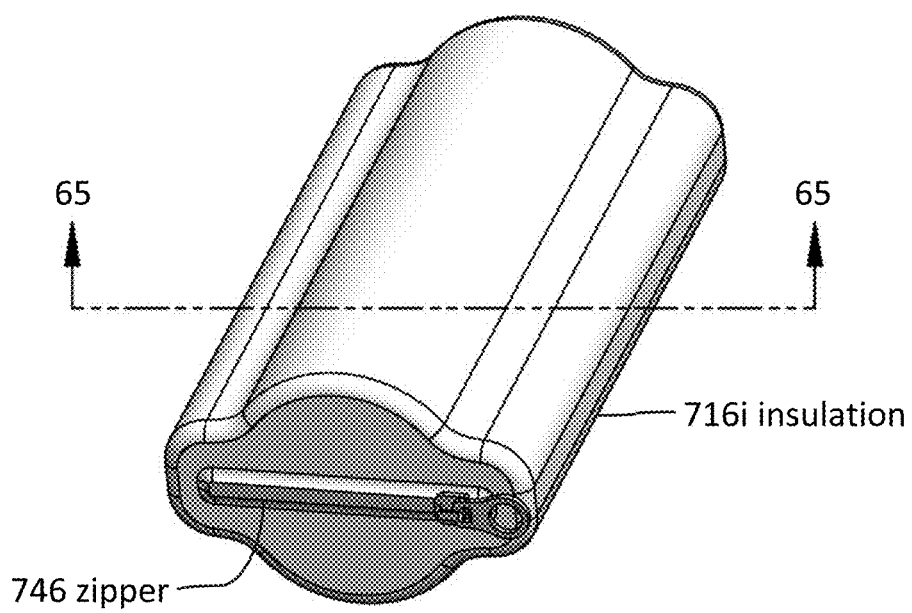
FIG. 64 illustrates a perspective view of insulation and a zipper, according to some embodiments.
Figure 65:
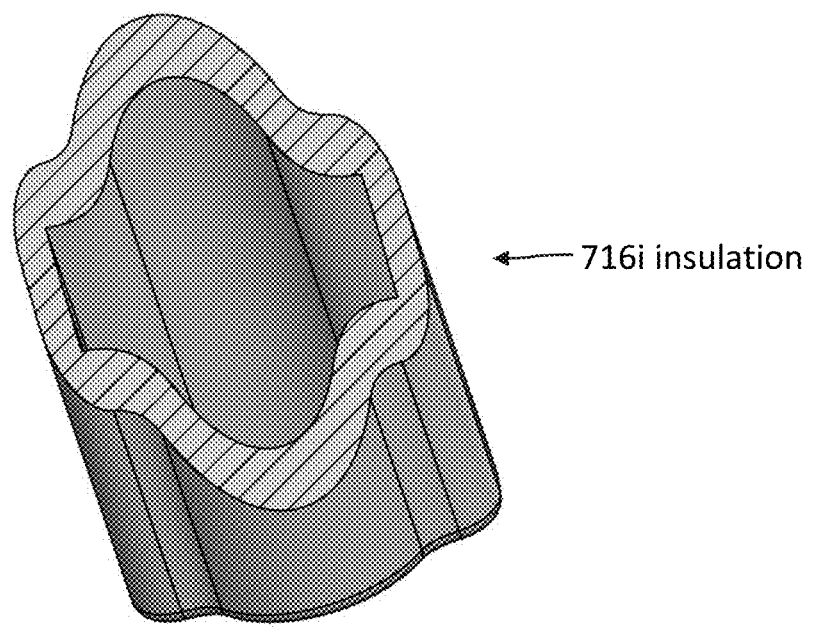
FIG. 65 illustrates a cross-sectional view taken along line 65-65 from FIG. 64, according to some embodiments.

FIG. 64 illustrates a perspective view of the insulation 716i and the zipper 746. FIG. 65 illustrates a cross-sectional view taken along line 65-65 from FIG. 64.

FIGS. 66-79 illustrate various embodiments that can be combined with any features, elements, structures, assemblies, chemistries, steps, methods, and innovations described in the contexts of other embodiments described herein and/or incorporated by reference herein.

A container 706k can be insulated by a vacuum chamber, insulation, and/or by any other suitable insulation. A lid 704k can cover an opening of the container 706k. The lid 704k can include features configured to enable a user to apply an unscrewing torque that is greater than the a screwing torque to increase the likelihood that a user will be able to unscrew the lid 704k from the container 706k. The lid 704k can include unique sealing and insulation structures to reduce the heat transfer permitted by the lid 704k.

The container 706k can also include a narrow neck area to reduce the area that is not insulated by the container 706k (e.g., not insulated by a vacuum chamber). The narrow neck can greatly improve the overall thermal performance of the storage system 700k. The flexible nature of various components inside the container 706k can enable the components to be inserted through the narrow neck and then expand into place once inside an interior of the container 706k. The interior can have a larger diameter than the neck.

Figures 68, 69:
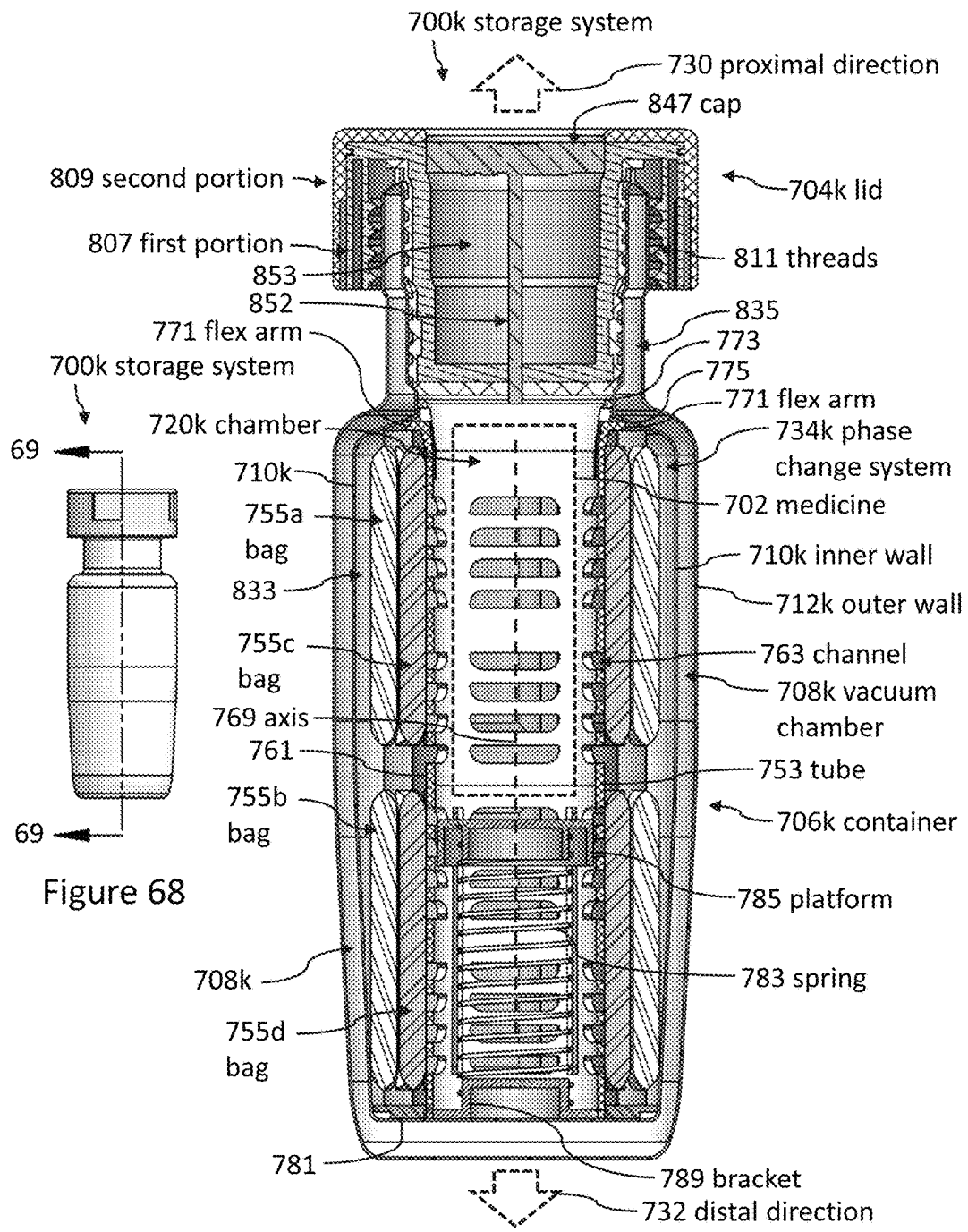
FIG. 69 illustrates a cross-sectional view taken along line 69-69 from FIG. 68, according to some embodiments.
Figure 70:
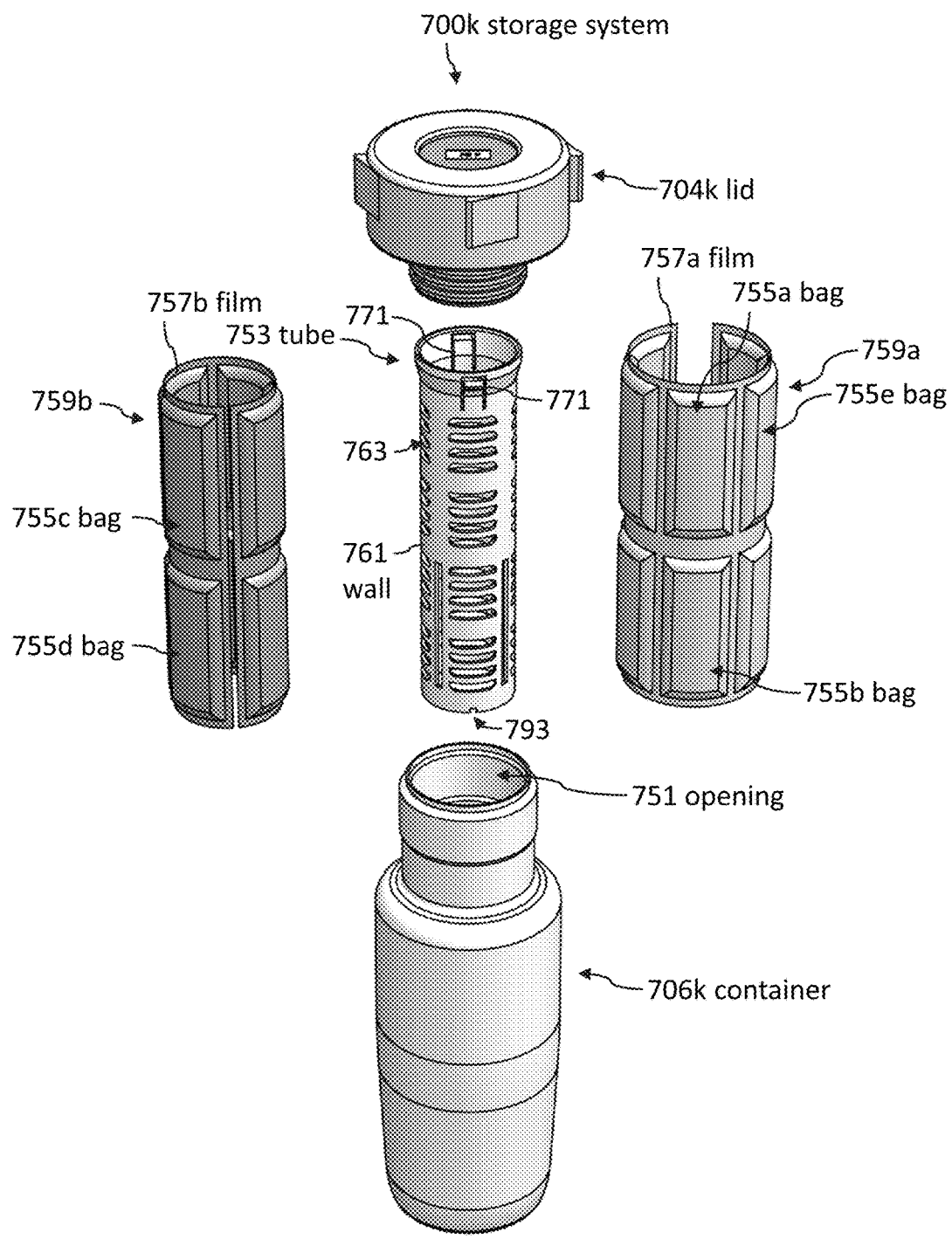
FIG. 70 illustrates a perspective view of a storage system in a disassembled state, according to some embodiments.

FIG. 68 illustrates a side view of the storage system 700k. FIG. 69 illustrates a cross-sectional view taken along line 69-69 in FIG. 68. FIG. 70 illustrates a perspective view of the storage system 700k in a disassembled configuration.

Referring now to FIGS. 69 and 70, the storage system 700k comprises an insulated container 706k having an opening 751. A lid 704k is configured to cover the opening 751.

Referring now to FIG. 69, the storage system 700k also comprises a phase change system 734k and a tube 753. The tube 753 can be rigid or flexible. The tube 753 can be molded from plastic.

The phase change system 734k is located inside the insulated container 706k. The tube 753 is located inside the insulated container 706k such that the tube 753 is in fluid communication with the opening 751 (shown in FIG. 70) to enable inserting a medicine 702 through the opening 751 and into the tube 753.

Many different types of insulated containers can be used. The insulated container 706k can be a vacuum flask having stainless steel walls and a vacuum chamber 708k located between the stainless steel walls (e.g., between the inner wall 710k and the outer wall 712k). The insulated container 706k can be a rigid shell surrounded by foam insulation. The insulated container 706k can be a compliant bag made from fabric and insulated with any suitable insulation material.

FIG. 70 illustrates flexible bags 755a-e, which can be at least partially filled with any of the phase change materials described herein. In some embodiments, some of these flexible bags 755a-e are filled with a first phase change material that has a first melting temperature greater than 40 degrees Fahrenheit and less than 74 degrees Fahrenheit; and the rest of the flexible bags 755a-e are filled with a second phase change material that has a second melting temperature greater than 74 degrees Fahrenheit and less than 100 degrees Fahrenheit. (Not all of the flexible bags are labeled to increase the clarity of the figures.)

In some embodiments, a flexible bag 755a is filled with a first phase change material that has a first melting temperature greater than 40 degrees Fahrenheit and less than 74 degrees Fahrenheit, and flexible bags 755b, 755e are filled with a second phase change material that has a second melting temperature greater than 74 degrees Fahrenheit and less than 100 degrees Fahrenheit. In this embodiment, flexible bags 755a, 755b, 755e are mechanically coupled to each other, but fluidly isolate the first phase change material from the second phase change material.

In some embodiments, flexible bags 755a, 755b, 755e are filled with a first phase change material that has a first melting temperature greater than 40 degrees Fahrenheit and less than 74 degrees Fahrenheit, and flexible bags 755c, 755d are filled with a second phase change material that has a second melting temperature greater than 74 degrees Fahrenheit and less than 100 degrees Fahrenheit.

In some embodiments, flexible bags 755c, 755d are filled with a first phase change material that has a first melting temperature greater than 40 degrees Fahrenheit and less than 74 degrees Fahrenheit, and flexible bags 755a, 755b, 755e are filled with a second phase change material that has a second melting temperature greater than 74 degrees Fahrenheit and less than 100 degrees Fahrenheit.

The flexible bags 755a, 755b, 755e (or 755c, 755d) can be made from one piece of film 757a (or 757b) that has multiple chambers at least partially filled with PCM. Each bag 755a-e has a PCM chamber. Each chamber can hold a different type of phase change material. In some embodiments, twelve chambers hold a first PCM and ten chambers hold a second type of PCM. The flexible bags can be made from multiple layers of film. The separate chambers can be made by sealing portions of the film together. The film can be a sheet of any waterproof material.

The film 757a, which forms the bags (e.g., 755a, 755b, 755e) can create a PCM blanket 759a that is flexible and rollable. The blanket 759a has PCM chambers and very thin sections of film that do not include PCM. The film sheets can enable the first blanket 759a to be rolled (e.g., moved from a flat orientation to a rolled orientation) to facilitate inserting the blanket 759a into a narrow opening 751. Once the blanket 759a has passed through the narrow opening 751, the blanket 759 can expand (e.g., at least partially unroll) to enable inserting the tube 753 into a middle portion of the container 706k such that the blanket 759a at least partially wraps around the tube 753.

The film 757b, which forms the bags (e.g., 755c, 755d) can create a PCM blanket 759b that is flexible and rollable. The blanket 759b has PCM chambers and very thin sections of film that do not include PCM. After the first blanket 759a is inserted into the container 706k, the second blanket 759b can be inserted into the container 706k (e.g., prior to inserting the tube 753 into the container 706k). The second blanket 759b can be located at least partially between the tube 753 and the first blanket 759a such that the second PCM blanket 759b at least partially wraps around the tube 753 and such that the first PCM blanket 759a at least partially wraps around the second PCM blanket 759b and at least partially wraps around the tube 753.

In some embodiments, the phase change system 706k comprises a first flexible bag 755a having a first phase change material and a second flexible bag 755c having a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

In some embodiments, the phase change system is configured to protect the medicine 702 (shown in FIG. 69) from a first external temperature less than a minimum recommended storage temperature and from a second external temperature greater than a maximum recommended storage temperature by utilizing phase changes to regulate a temperature of the medicine 702.

Referring now to FIG. 69, the medicine 702 can be any type of medicine. In some embodiments, the medicine 702 is an injection device having epinephrine. The injection device can be located in the tube 753.

In several embodiments, the first flexible bag 755a and the second flexible bag 755c are located inside the insulated container 706k and are located outside the tube 753 such that the first flexible bag 755a and the second flexible bag 755c are located between an inner wall 710k of the insulated container 706k and an outer wall 761 of the tube 753.

Figure 71:
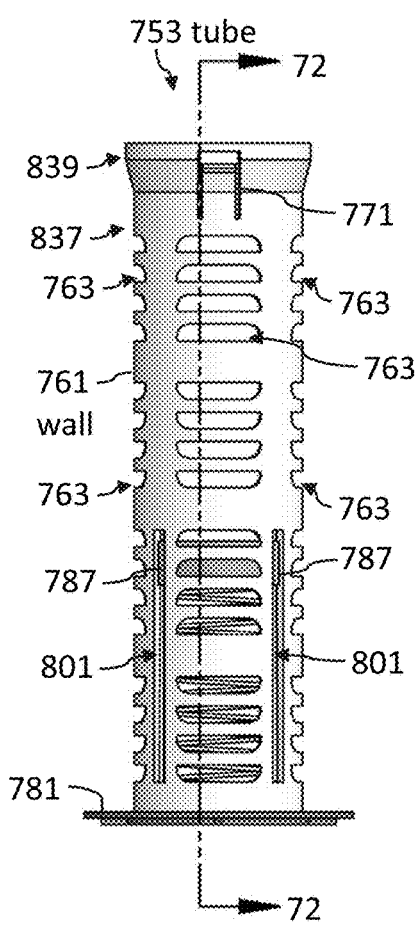
FIG. 71 illustrates a side view of a tube, according to some embodiments.
Figure 72:
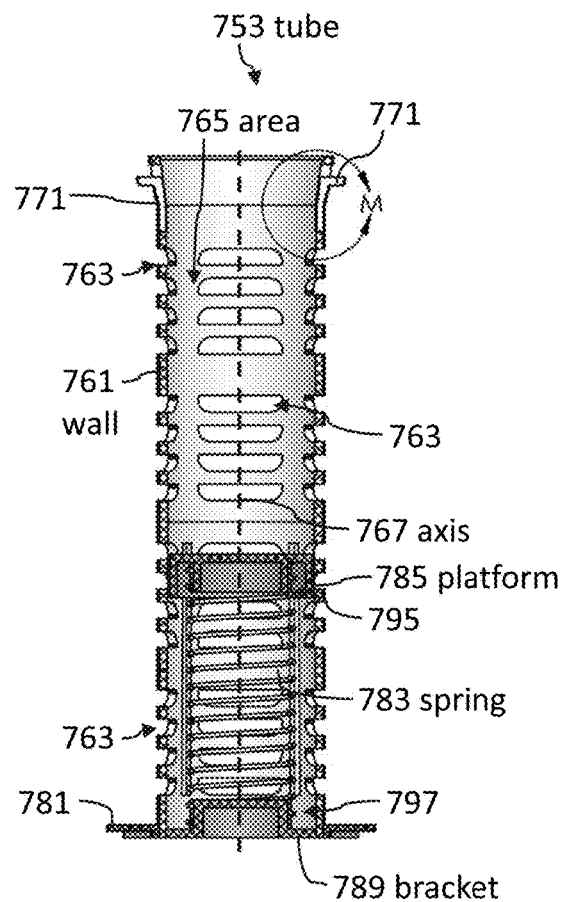
FIG. 72 illustrates a cross-sectional view taken along line 72-72 from FIG. 71, according to some embodiments.

Referring now to FIGS. 71 and 72, the outer wall 761 of the tube 753 comprises many ventilation channels 763. To increase the clarity of the figures, not all of the ventilation channels are labeled.

The ventilation channels 763 are configured to enable airflow between an area 765 inside the tube 753 and the phase change system 734k (labeled in FIG. 69). The area 765 inside the tube 753 can be where the medicine 702 is stored inside the system 700k (shown in FIG. 69).

The outer wall 761 of the tube 753 can comprise a second ventilation channel 763 located on an opposite side of the tube 753 relative to a first ventilation channel 763. The tube 753 can include many ventilation channels 763 that are oriented radially outward (e.g., relative to a central axis 767 of the tube 753). The ventilation channels 763 can have diverse shapes (e.g., round, square, rectangle). As shown in FIG. 69, the ventilation channels 763 can be configured to facilitate heat transfer between the medicine 702 and the phase change system 734k.

Referring now to FIGS. 69 and 70, the bags 755a-e can be flexible such that they are configured to conform to fit in an area between the tube 753 and an interior wall 710k of the insulated container 706k. In some embodiments, the bags 755a-e are "highly flexible" such that when drained of PCM, a first end of each bag can be bent 180 degrees relative to an opposite end of the bag without causing any damage to the bag. Conformable bags 755a-e can be helpful during the assembly through the narrow opening 751.

In some embodiments, a first flexible bag comprises at least two fluidly isolated chambers (e.g., 755a, 755b, 755e) having a first phase change material. The second flexible bag can comprise at least two fluidly isolated chambers (e.g., 755c, 755d) having a second phase change material.

As shown in FIG. 69, the first flexible bag (e.g., 755a, 755b) can be wrapped at least partially around the tube 753. The second flexible bag (e.g., 755c, 755d) can be wrapped at least partially around the tube 753. A first PCM blanket 759a (shown in FIG. 70) is wrapped around a second PCM blanket 759b (shown in FIG. 70) in the configuration shown in FIG. 69. In several embodiments, the first flexible bag (e.g., 755a, 755b) is wrapped at least partially around the second flexible bag. In some embodiments, the second flexible bag (e.g., 755c, 755d) is wrapped at least partially around the first flexible bag (e.g., 755a, 755b).

The insulated container 706k is insulated by a vacuum chamber 708k. The vacuum flask can comprise an inner wall 710k and an outer wall 712k with a gas pressure between the inner wall and the outer wall that is less than atmospheric pressure (to create a "vacuum chamber"). In some embodiments, the pressure between the inner wall 710k and the outer wall 712k can be less than 60% of atmospheric pressure, less than 40% of atmospheric pressure, and/or less than 20% of atmospheric pressure. The atmospheric pressure can be measured at sea level.

The insulated container 706k can use other types of insulation methods in addition to or instead of using a vacuum chamber 708k. The other types of insulation described herein can be used to insulate the container 706k.

As shown in FIG. 69, the phase change system 734k is wrapped around the tube 753, the insulated container 706k comprises a first central axis 769, the tube comprises a second central axis 767 (shown in FIG. 72) that is within 15 degrees of being aligned with the first central axis 769, and the tube 753 extends from an upper half (i.e., a proximal half) of the insulated container 706k to a lower half (i.e., a distal half) of the insulated container 706k. (The upper half is located closer to the lid 704k than the lower half.)

As used herein, "extends" means to continue in a specified direction or over a specified distance, but unless stated otherwise, typically does not mean to become longer.

In some embodiments, the first central axis 769 is aligned with the second central axis 767 (shown in FIG. 72). In some embodiments, the tube extends along a portion of the first central axis 769 such that the tube is radially centered relative to the container 706k.

The tube 753 is held inside the insulated container 706k. At least one flex arm 771 is configured to hold the tube 753 inside the insulated container 706k. The flex arms 771 protrude farther radially outward (relative to a central axis 769) than a narrowest section 773 of an interior of the insulated container 706k such that the flex arms 771 are configured to flex radially inward (relative to a central axis 769) in response to inserting the tube 753 into the insulated container 706k and the flex arms 771 are configured to contact a narrowing section 775 of the interior to hold the tube 753 inside the insulated container 706k.

Figure 73:
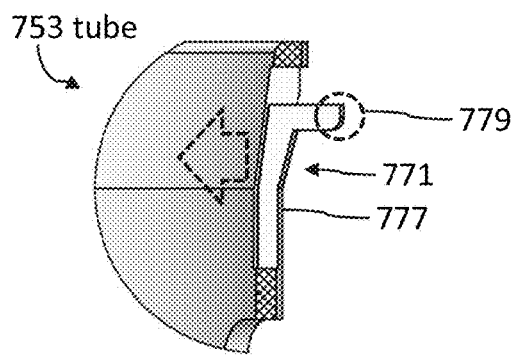
FIG. 73 illustrates an enlarged view of the area indicated by circle M in FIG. 72, according to some embodiments.

An arrow in FIG. 73 illustrates a radially inward direction in which the flex arm 771 bends in response to contacting the narrowest section 773 (in the neck of the container 706k) as the tube 753 is inserted through the opening 751 and into the final position of the tube 753 (as shown in FIG. 69). Flexing radially inward enables the arm 771 to move past the narrowest section 773.

The flex arm 771 comprises a cantilever beam 777. The cantilever beam 777 can be oriented within 20 degrees of parallel to a central axis 767 (and/or a central axis 769). These orientations are helpful to enable the cantilever beam 777 to flex in response to inserting the tube 753 into the container 706k.

Referring now to FIGS. 69, 70, and 73, the cantilever beam 777 (of the flex arm 771) is oriented within 80 degrees of a direction oriented (1) along a central axis 767 of the tube 753 and (2) towards the opening 751 such that pulling the tube 753 towards the opening 751 increases a resistance of the flex arm 771 to the pulling. This "engaging" structure can help prevent inadvertent removal of the tube 753 from the insulated container 706k. The tube 753 and the flex arms 771 can be molded plastic (e.g., as a single piece or as separate pieces that are coupled together).

The tube 753 comprises flex arms 771 having a cantilever beam 777 and a portion 779 to engage an interior of the insulated container 706k to hold the tube 753 inside the insulated container 706k (e.g., in the narrowing section 775 of the interior). The portion 779 is oriented towards a narrowing portion 775 of an interior of the insulated container 706k. For example, the interior of the container 706k can be the widest in a region that holds the phase change system 734k. The interior of the container 706k can be narrower in the opening 751 than in the region that holds the phase change system 734k. A narrowing portion 775 is typically necessary to transition from the wider portion to the narrow portion of the interior of the container 706k. Engaging this narrowing portion can be particularly helpful in preventing the tube 753 from falling out of the insulated container 706k.

In some embodiments, the tube 753 is coupled to a bracket 781 that holds the tube 753 inside the insulated container 706k. Bracket embodiments can have diverse shapes and sizes. In some embodiments, the bracket 781 is rigidly coupled to an interior of the insulated container 706k. In some embodiments, the bracket 781 has a hole in which a portion of the tube 753 is placed (e.g., to hold the tube in a center of the insulated container such that the hole of the bracket 781 is aligned with the central axis 769 of the container 706k).

In several embodiments, a maximum width of the opening 751 is measured from a central axis 769 of the insulated container 706k in a direction perpendicular to the central axis 769. The tube 753 can be coupled to a bracket 781 having an outermost edge located farther from the central axis 769 than the maximum width of the opening 751 such that the bracket 781 holds the tube 753 inside the insulated container 706k. In other words, the outermost edge of the bracket 781 can stick out so far that it cannot fit through the opening 751. (The bracket 781 can flex to enable inserting the bracket 781 into the insulated container 706k.)

In several embodiments, a spring 783 facilitates removing the medicine 702 from the insulated container 706k (e.g., by pushing the medicine 702 towards the opening 751 of the insulated container 706k to help a user grasp a proximal portion of the medicine 702).

The spring 783 is located in the insulated container 706k. The spring 783 is configured to push the medicine 702 towards the opening 751. A proximal platform 785 can be located inside the tube 753 such that the spring 783 pushes the proximal platform 785 towards the opening 751 to push the medicine 702 at least partially out of the opening 751 so a user can pull the medicine 702 out of the storage system 700k.

Figure 74:
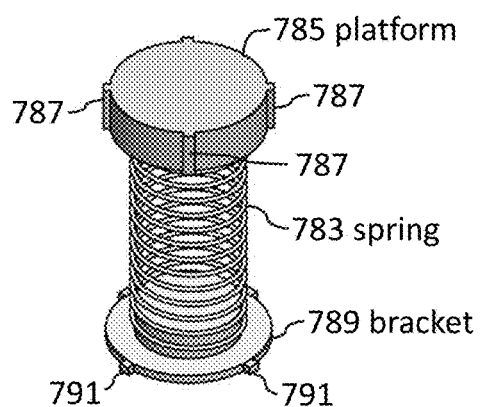
FIG. 74 illustrates a perspective view of a spring assembly, according to some embodiments.

FIGS. 72 and 74 illustrates the spring system, which has a spring 783, a proximal platform 785, and a bracket 789. The spring 783 is configured to push the proximal platform 785 away from the bracket 789. The bracket 789 has radially outward protrusions 791 that interlock with notches 793 (shown in FIG. 70) in the tube 753.

The bracket 789 and the platform 785 comprise protrusions 797 and/or indentations 795 to receive an end of the spring 783 to secure the spring 783. The protrusions 797 and indentations 795 are cylindrical.

Referring now to FIGS. 71 and 74, the platform 785 comprises radially outward protrusions 787 that are located in guides (e.g., vertical slots) 801 of the tube 753. The protrusions 787 and guides 801 help prevent the platform 785 from rotating relative to the tube 753.

Referring now to FIGS. 75-78, in several embodiments, systems include a rotational release mechanism 803 to guard against overtightening, which could result in difficulty removing the lid 704k of the storage system 700k. The lid 704k (and its rotational release mechanism 803) can be used with any of the containers described herein and/or incorporated by reference.

The insulated container 706k and/or the lid 704k can comprise a rotational release mechanism 803 configured such that the lid 704k is rotatable relative to the insulated container 706k in a first rotational direction 813 that tightens the lid 704k to the insulated container 706k (via an applied torque) and in a second rotational direction 815 that loosens the lid 704k from the insulated container 706k (via an applied torque). The lid 704k can comprise a first portion 807 and a second portion 809. The first portion 807 can comprise threads 811 that couple the lid to the insulated container 706k.

The second portion 819 of the lid 704k is configured to rotate in the first rotational direction 813 relative to the first portion 807 of the lid 704k in response to a first applied torque that exceeds a release threshold (e.g., a torque). The second portion 809 of the lid 704k can be configured to resist rotation in the second rotational direction 815 relative to the first portion 807 in a presence of a second applied torque that is at least thirty percent larger than a magnitude of the release threshold.

In several embodiments, the rotational release mechanism 803 comprises an interface 816 between the first portion 807 and the second portion 809. The interface 816 can have teeth 817 slanted such that rotating the second portion 809 relative to the first portion 807 of the lid 704k in the first rotational direction 813 requires a lower torque than rotating the second portion 809 relative to the first portion 807 of the lid 704k in the second rotational direction 815.

The second portion 809 of the lid 704k can have protrusions 819 that protrude radially inward relative to a central axis 818 of the lid 704k. The interface 816 can be configured such that rotating the second portion 809 relative to the first portion 807 causes a protrusion 819 to collide with the tooth 817.

The tooth 817 has a peak 822. The peak of the tooth is the "highest" point of the tooth 817. When a tooth protrudes radially outward, the peak is the point of the tooth that is the farthest radially outward. When a tooth protrudes radially inward, the peak is the point of the tooth that is the farthest radially inward. When a tooth protrudes upward, the peak is the point of the tooth that is the farthest upward. When a tooth protrudes downward, the peak is the point of the tooth that is the farthest downward.

The tooth 817 comprises a first side 820 and a second side 821. The first side 820 is separated from the second side 821 by the peak 822. When the lid 704k is screwed into the container 706k, the protrusion 819 collides with the first side 820 of the tooth 817. When the lid 704k is unscrewed from the container 706k, the protrusion 819 collides with the second side 821 of the tooth 817. The tooth 817 is slanted such that the first side 820 is more gradual than the second side 821. In other words, the second side 821 is more abrupt than the first side 820. As a result, the torque required to rotate the second portion 809 (of the lid 704k) relative to the first portion 807 (of the lid 704k) is less when the lid 704k is unscrewed from the container 706k than when the lid 704k is screwed into the container 706k (as measured when the first portion 807 does not rotate).

Figure 75:
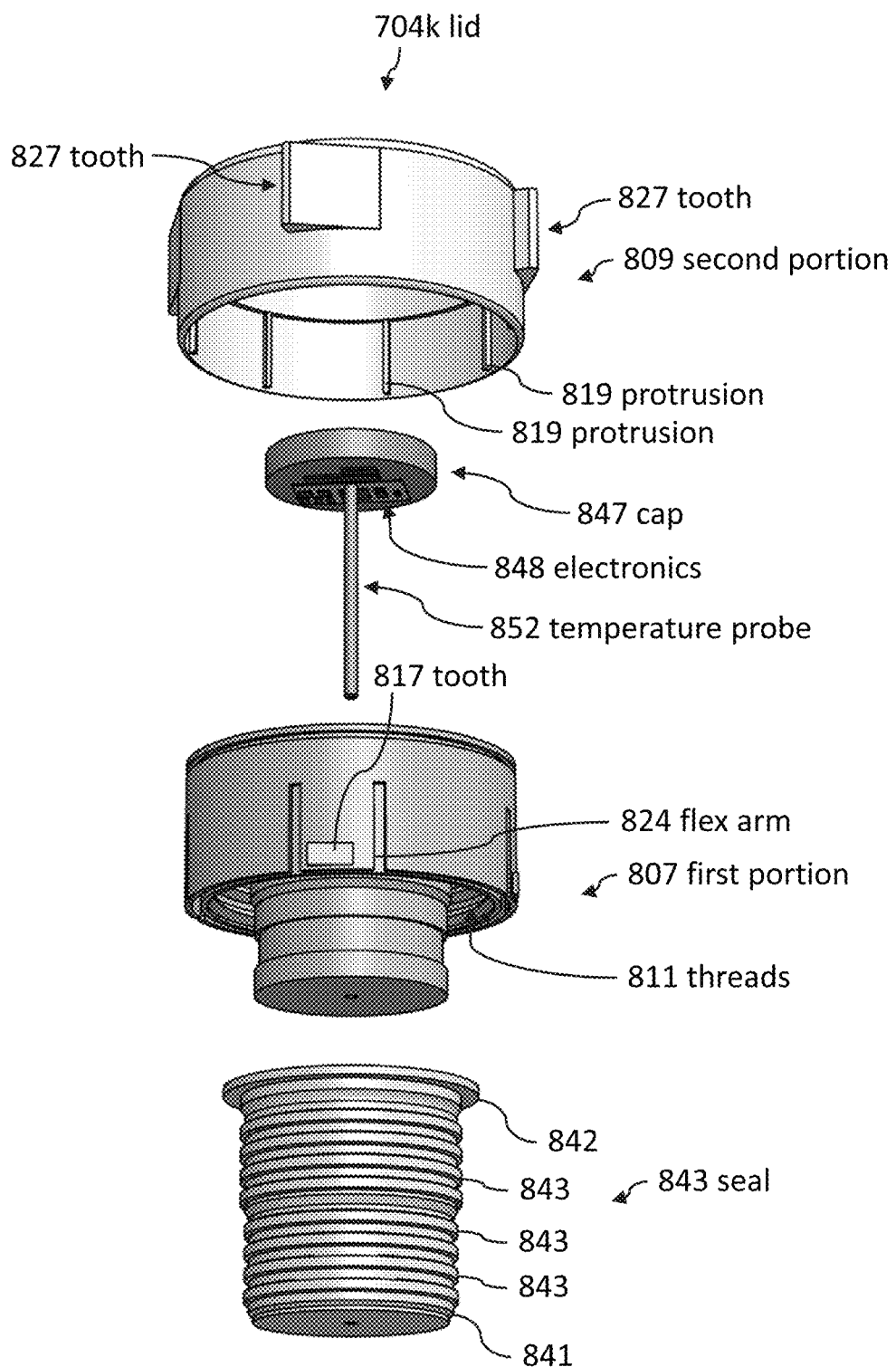
FIG. 75 illustrates a perspective, exploded view of a lid, according to some embodiments.

As shown in FIG. 75, the tooth 817 is located on a flex arm 824 configured to bend radially inward to enable the protrusion 819 to move past the tooth 817. As shown in FIG. 77, a gap 825 enables the tooth 817 to flex radially inward.

FIG. 78 illustrates teeth 827 that protrude radially outward and are slanted such that they provide greater grip when unscrewing the lid 704k than when screwing the lid 704k into the container 706k. The teeth 827 protrude radially outward from an outer perimeter of the lid 704k.

Each tooth 827 comprises a first side 828, a second side 829, and a peak 830. The first side 828 is separated from the second side 829 by the peak 830. The tooth 827 is slanted such that the first side 828 is more gradual than the second side 829. In other words, the second side 829 is more abrupt than the first side 828.

In some embodiments, on the first side 828, the tooth 827 is tangent to an outer perimeter of the lid 704k. In some embodiments, the first side 828 is defined by a point 857 where the tooth 827 joints the outer perimeter 859 of the lid 704k. (The outer perimeter 859 of the lid 704k can be cylindrical and/or have a circular cross section that is perpendicular to a central axis of the lid 704k.)

A first measurement line can measured between the point 857 and the peak 830 of the tooth 827. A second measurement line can be measured between a central axis of the lid 704k and the point 857. In several embodiments, a first angle between the first measurement line and the second measurement line is less than 135 degrees; less than 120 degrees; and/or greater than 89 degrees.

In some embodiments, the second side 829 is defined by a point 861 where the tooth 827 joints the outer perimeter 859 of the lid 704k. A third measurement line can measured between the point 861 and the peak 830 of the tooth 827. A fourth measurement line can be measured between a central axis of the lid 704k and the point 857. In several embodiments, a second angle between the third measurement line and the fourth measurement line is greater than 135 degrees; greater than 150 degrees; and/or equal to 180 degrees such that the third measurement line and the fourth measurement line are parallel to each other.

In several embodiments, the first measurement line is at least 30 percent longer and/or at least 50 percent longer than the third measurement line such that a first average slope of the first side 828 is less than a second average slope of the second side 829.

In several embodiments, a first coefficient of friction of the first side 828 is less than a second coefficient of friction of the second side 829 such that the second side 829 is configured to provide stronger gripping traction than the first side 828.

FIG. 79 illustrates a perspective view of a phase change system 734h that has bags 755f-i at least partially filled with PCM. Flex arms 771 protrude radially outward to help secure the tube 753 in the container (not shown).

Referring now to FIGS. 69, 70, and 79, a storage system 700k can comprise an insulated container 706k having an opening 751; a lid 704k configured to cover the opening 751; a phase change system 734k located inside the insulated container 706k; and a tube 753 located inside the insulated container 706k such that the tube 753 is in fluid communication with the opening 751 (to enable inserting a medicine 702 through the opening 751 and into the tube 753). The phase change system 734h can comprise a first bag 755a having a first phase change material. The first phase change material can have a first melting temperature greater than 40 degrees Fahrenheit and less than 74 degrees Fahrenheit. The insulated container 706k can be a vacuum flask such that the insulated container 706k is insulated by a vacuum chamber 708k. The first bag 755a can be located inside the insulated container 706k and outside the tube 753 such that the first bag 755a is located between an inner wall 710k of the insulated container 706k and an outer wall 761 of the tube. The tube 753 can extend from an upper half of the insulated container 706k to a lower half of the insulated container 706k such that the storage system 700k is configured to enable a user to remove the lid 704k, insert the medicine 702 through the opening 751 and into the tube 753, replace the lid 704k, and protect the medicine 702 from temperatures below 40 degrees Fahrenheit.

In several embodiments, a storage system 700k comprises an insulated container 706k having an opening 751; a lid 704k configured to cover the opening 751; a phase change system 734k located inside the insulated container 706k; and a tube 753 located inside the insulated container 706k such that the tube 753 is in fluid communication with the opening 751 (to enable inserting a medicine 702 through the opening 751 and into the tube 753). The phase change system 734k can comprise a first bag 755a having a first phase change material. The first phase change material can have a first melting temperature greater than 74 degrees Fahrenheit and less than 100 degrees Fahrenheit. The insulated container 706k can be insulated by a vacuum chamber 708k. The first bag 755a can be located inside the insulated container 706k and outside the tube 753 such that the first bag 755a is located between an inner wall 710k of the vacuum chamber 708k and an outer wall 761 of the tube 753. The tube 753 can extend from an upper half of the insulated container 706k to a lower half of the insulated container 706k such that the storage system 700k is configured to enable a user to remove the lid 704k, insert the medicine 702 through the opening 751 and into the tube 753, replace the lid 704k, and protect the medicine 702 from temperatures above 100 degrees Fahrenheit.

In some embodiments, an interior of the insulated container 706k comprises a first cylindrical section 833 and a second cylindrical section 835 that is closer to the opening 751 than the first cylindrical section 833. The second cylindrical section 835 can have a second diameter that is smaller than a first diameter of the first cylindrical section 833. The first cylindrical section 833 can have a first length measured along a central axis 769 of the insulated container 706k. The second cylindrical section 835 can have a second length measured along the central axis 769 of the insulated container 706k. The first length can be at least twice as long as the second length.

Referring now to FIGS. 69-72, in several embodiments, the tube 753 comprises a third cylindrical section 837 having a third diameter and a third length. The third length is measured along a central axis 767 of the tube 753. The tube 753 can comprise a fourth cylindrical section 839 having a fourth diameter and a fourth length. The fourth length is measured along the central axis 767 of the tube 753. The fourth cylindrical section 839 can couple the third cylindrical section 837 to the opening 751 of the insulated container 706k. The fourth diameter can be larger than the third diameter. The third length can be at least twice as long as the fourth length.

In some embodiments, threads 811 of the storage system 700k couple the insulated container 706k to the lid 704k. At least one of the second cylindrical section 835 and a portion of the insulated container 706k located radially outward from the second cylindrical section 835 can comprise threads 811 configured to couple the lid 704k to the insulated container 706k. As used herein, a section can be cylindrical even if it has threads.

FIG. 75 illustrates a perspective, exploded view of the lid 704k. In several embodiments, seals are configured to limit or eliminate fluid communication between an environment outside the storage system 700k and an interior of the storage system 700k where the medicine 702 is stored.

The lid 704k can comprise a seal 840, which can include a distal compression seal 841, a proximal compression seal 842, and at least one axial seal 843 located between the distal compression seal 841 and the proximal compression seal 843. Seals can be wiper seals, o-rings, or any other suitable type of seal. Seals can be made from silicone or any other suitable material.

The lid 704k can include a cap 847. The cap 847 (or any other portion of the lid 704k and/or the storage system 700k) can include electronics 848, a battery 849, and a display 850. The display 850 can show temperature information and other information related to medicine storage. The electronics 848 can include a printed circuit board 851. A temperature probe 852 can be used to measure a temperature inside the medicine storage area of the system 700k. The many features described in the context of FIG. 5 of U.S. Nonprovisional patent application Ser. No. 14/849,884, including but not limited to the electronic features and the computer 76, can be combined with any of the embodiments described in the context of FIGS. 69-79. The lid 18 shown in FIG. 5 of U.S. Nonprovisional patent application Ser. No. 14/849,884 can be used with any of the storage system 700k.

In some embodiments, all features, assemblies, components, and innovations related to the lid 18 shown in FIG. 5 of U.S. Nonprovisional patent application Ser. No. 14/849,884 are combined with the features, assemblies, components, and innovations described herein in the context of lid 704k (shown in FIGS. 66-70 and 75-78).

An area 853 under the cap 847, around the temperature probe 852, and/or within the first portion 807 of the lid 704k can be filled and/or insulated with foam or any other suitable insulation. In some embodiments, this area 853 comprises a second vacuum chamber that is located inside the lid 704k.

In any of the embodiments described herein and/or incorporated by reference, a storage system can comprise a thermometer configured to measure a temperature of an interior area of the insulated container; a wireless communication system communicatively coupled with a remote computing device; and a first wireless communication sent from the medicine storage system to the remote computing device in response to at least one of (1) the temperature falling below a predetermined minimum temperature threshold, (2) the temperature rising above a predetermined maximum temperature threshold, (3) falling below a first predetermined amount of time until the temperature is predicted to fall below the predetermined minimum temperature threshold, and (4) falling below a second predetermined amount of time until the temperature is predicted to rise above the predetermined maximum temperature threshold. Additional details are described in the context of FIG. 5 of U.S. Nonprovisional patent application Ser. No. 14/849,884 and in other portions of U.S. Nonprovisional patent application Ser. No. 14/849,884. The electronics 847 shown in FIG. 78 include a wireless communication system. FIGS. 69 and 75 illustrate a lid having a thermometer (e.g., a temperature probe 852).

In any of the embodiments described herein and/or incorporated by reference, a storage system can comprise a thermometer configured to measure a temperature of an interior area of the insulated container; and a computing system configured to emit at least one of a visual indicator and an audio indicator in response to at least one of (1) the temperature falling below a predetermined minimum temperature threshold, (2) the temperature rising above a predetermined maximum temperature threshold, (3) falling below a first predetermined amount of time until the temperature is predicted to fall below the predetermined minimum temperature threshold, and (4) falling below a second predetermined amount of time until the temperature is predicted to rise above the predetermined maximum temperature threshold. Additional details are described in the context of FIG. 5 of U.S. Nonprovisional patent application Ser. No. 14/849,884 and in other portions of U.S. Nonprovisional patent application Ser. No. 14/849,884. The electronics 847 shown in FIG. 78 include a computing system configured to emit visual indicators and audio indicators. FIGS. 69 and 75 illustrate a lid having a thermometer (e.g., a temperature probe 852).

In any of the embodiments described herein and/or incorporated by reference, a storage system can have a lid configured to cover an opening of an insulated container. The lid can comprise a thermometer system configured to measure a temperature of an interior area of the insulated container. The lid can comprise a display configured to show the temperature. The lid can comprise an inward portion and an outward portion. The inward portion can be located closer to the medicine storage area than the outward portion of the lid. A portion of the thermometer system can be coupled to the inward portion of the lid such that the portion of the thermometer system is configured to sense the temperature of the interior area. The display can be located on an outward facing side of the lid such that the display is configured to show the temperature even when the lid is screwed onto the insulated container. The thermometer system and the display can be electrically coupled to a computing system configured to enable the storage system to measure the temperature and show the temperature on the display. Additional details are described in the context of FIG. 5 of U.S. Nonprovisional patent application Ser. No. 14/849,884 and in other portions of U.S. Nonprovisional patent application Ser. No.

Figure 66:
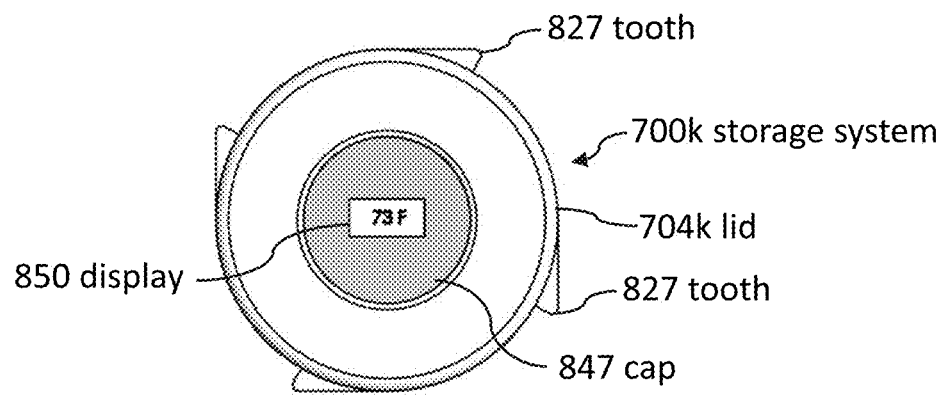
FIG. 66 illustrates a top view of a storage system, according to some embodiments.

14/849,884. The lid 704k illustrated in FIG. 76 includes a temperature probe 852 that protrudes distally from a distal end of the lid 704k. FIG. 66 illustrates that the lid 704k includes a display 850 (which shows a temperature e.g., "73 F," of an interior area of the insulated container 706k). The electronics 847 shown in FIG. 78 include a computing system that electrically couples the thermometer system 852 and the display 850 to enable the storage system 700k to measure the temperature and show the temperature on the display 850.

Additional Details

Several embodiments of a storage system for injectable substances include a thermally insulating container. A substance with a high heat capacity can be located inside the insulating container. The substance can have a specific heat capacity of at least 2 Joules/gram*Kelvin and/or a volumetric heat capacity of at least 2 Joules/cm^3*Kelvin. A chamber configured to hold an injectable substance can also be located inside the insulating container. In some embodiments, the substance with a high heat capacity at least partially surrounds at least a portion of the chamber configured to hold the medicine (e.g., an injectable substance).

The injectable substance chamber 44 (e.g., as shown in FIG. 24) can be configured to hold an injectable substance, which may be packaged in a separate storage container such as a plastic vial, a glass jar, and/or an injection device such as a syringe. Example injectable substances can be contained in products such as EpiPens, Twinjects, Adrenaclicks, Anapens, Jexts, Allerjects, Auvi-Qs, and ComboPens. Some injectable substance chambers 44 are configured to hold multiple containers of injectable substances. Some injectable substance chambers 44 are configured to hold an inhaler and/or another drug container.

As used herein, the term injectable substance can include a container that holds a liquid that users inject into their bodies. Some embodiments are similar to other embodiments described herein except the injectable substance is replaced with a container of an injectable liquid. The container can be plastic, glass, and/or a syringe.

The injectable substance (e.g., a medicine 702) can include epinephrine, adrenaline, insulin, hormones, and/or neurotransmitters. The injectable substance can include liquids or gases used to treat acute allergic reactions, to avoid anaphylactic shock, and/or to treat anaphylactic shock. The injectable substance can include liquids or gases used to treat diabetes. In some embodiments, the medicine 702 is an epinephrine auto-injector such as the EpiPen or EpiPen Jr. made by Mylan Specialty L.P. In some embodiments, the injectable substance is replaced by another pharmaceutical product or by another product that benefits from temperature stability.

The many features described in the context of FIG. 5 of U.S. Nonprovisional patent application Ser. No. 14/849,884, including but not limited to the electronic features and the computer 76, can be combined with any of the embodiments described herein or incorporated by reference herein. To reduce redundancy and to increase the clarity of other features in other figures, the features described in the context of FIG. 5 of U.S. Nonprovisional patent application Ser. No. 14/849,884 are not repeated for each figure herein. The lid 18 shown in FIG. 5 of U.S. Nonprovisional patent application Ser. No. 14/849,884 can be used with any of the storage systems described herein to combine many electrical elements with many types of storage systems.

Each embodiment described herein or incorporated by reference can include a thermometer (e.g., as described in U.S. Nonprovisional patent application Ser. No. 14/849, 884), which can include a temperature probe 64a. As described in U.S. Nonprovisional patent application Ser. No. 14/849,884, at least a portion of the temperature probe 64a can be located inside the injectable substance chamber 44 (e.g., a first chamber) such that the temperature probe 64a is configured to measure, evaluate, test, and/or determine the temperature inside the injectable substance chamber 44 and/or the temperature of the injectable substance 50. The thermometer can also include a temperature display 62a, which can be located outside of the cover 48 such that the temperature display 62a is configured such that a user can read and/or determine the temperature on the display 62a without opening the lid 18. A speaker 24 can emit a sound to warn the user if a temperature inside the storage system 11 exceeds a predetermined temperature threshold or falls below a predetermined temperature threshold.

As explained in U.S. Nonprovisional patent application Ser. No. 14/849,884, a computer 76, a display 62b, and/or a speaker 24 can warn the user if a temperature, such as the temperature of the first chamber, an injectable substance, a medicine, and/or a thermal bank, deviates outside of a predetermined temperature range, which can be greater than 55 degrees Fahrenheit and/or less than 90 degrees Fahrenheit (such that the system is configured to warn the user prior to a portion of the system reaching a temperature that could harm the medicine stored by the system).

Some embodiments include an insulated container configured to maintain injectable substances at approximately room temperature. In several embodiments, the insulated container can include a chamber configured to hold an injectable substance. The chamber can be surrounded by a substance with high heat capacity. The substance with high heat capacity can be surrounded by an insulated cover.

Referring now to FIG. 3, storage systems can include an outer case, which can be made of plastic, metal, insulation, and/or any suitable material. The storage system can include a vacuum chamber 708 (e.g., in a vacuum flask). The inner wall 710 can be a first flask. The outer wall 712 can be a second flask. The first and second flasks can form a vacuum flask. The vacuum flask can be located inside the outer case such that the outer case can be configured to protect the vacuum flask from damage such as denting or cracking. The vacuum flask can comprise an inner wall 710 and an outer wall 712 with a gas pressure between the inner wall and the outer wall that is less than atmospheric pressure. In some embodiments, the pressure between the inner wall and the outer wall can be less than 60% of atmospheric pressure, less than 40% of atmospheric pressure, or less than 20% of atmospheric pressure. The atmospheric pressure can be measured at sea level. The vacuum flask can include a first flask placed inside a second flask. The first flask and the second flask can be joined at the neck 722 such that the area between the first flask and the second flask is hermetically sealed from the air outside of the area between the first flask and the second flask. The vacuum flask can be made of metal, glass, foam, and/or plastic.

Many embodiments include a phase change system having multiple phase change materials (e.g., one, two, three, four, or more phase change materials with unique melting temperatures). The multiple phase change materials can provide protection from temperatures above and below room temperatures. Thus, one system can shield medicine from temperature variations in both directions without requiring previous knowledge of whether a person will bring the storage system into hot or cold weather.

One way to build a storage system that resists temperature decreases and increases is to include two phase change materials inside the thermal bank. The first phase change material can resist temperature decreases due to cold outside environments. The second phase change material can resist temperature increases due to hot outside environments.

The first phase change material can have a high heat of fusion to enable a relatively lightweight system that can still provide sufficient resistance to temperature changes. The first phase change material can release large amounts of heat before allowing the temperature inside the first chamber to decrease. For example, the first phase change material can release large amounts of heat (per gram of the material) as the material changes from a liquid to a solid. The melting temperature of the first phase change material can be less than 70 Fahrenheit (e.g., just below room temperature) and greater than the minimum recommended medicine storage temperature.

For example, if a manufacturer of a medicine recommends a minimum storage temperature of 45 degrees Fahrenheit, then the first phase change material can be selected with a melting temperature between 45 degrees Fahrenheit and around 70 degrees Fahrenheit (e.g., below a room temperature). Thus, when a temperature inside the insulated container goes below the melting point, the first phase change material releases large amounts of heat before allowing the temperature inside the first chamber to significantly decrease. As a result, the first phase change material dramatically prolongs the time required to decrease the temperature inside the first chamber below the minimum storage temperature.

This additional time can enable the medicine to remain outside much longer without reducing the efficacy of the medicine than would be the case without the storage system. Moreover, the phase change enables the storage system to be much more compact than would be the case with a storage system that only uses water to resist temperature changes (at temperatures above 32 degrees Fahrenheit).

The second phase change material of the storage system can resist temperature increases due to hot outside environments. The second phase change material can have a high heat of fusion and a melting temperature that is greater than room temperature and less than the maximum recommended medicine storage temperature. For example, if the maximum recommended storage temperature is 85 degrees Fahrenheit, then in some embodiments, the second phase change material can have a melting temperature between 80 degrees Fahrenheit and 85 degrees Fahrenheit. Thus, the second phase change material can absorb a large amount of heat (to melt) before the second phase change material would allow the temperature inside the storage system to increase significantly above the melting temperature of the second phase change material.

The rate of heat transfer between the outside environment 30 and the first chamber (e.g., the void 154) is reduced by reducing the temperature difference between the outside environment and the thermal bank 140 (during melting or solidifying). Thus, phase change materials can be selected that have a melting point near the minimum storage temperature (e.g., without being less than the minimum storage temperature) or near the maximum storage temperature (e.g., without being greater than the maximum storage temperature). (The minimum and maximum storage temperatures can be recommended by the manufacturer of the medicine and are often included with literature provided with the medicine.) "Near the minimum" or "near the maximum" can be within 10 degrees Fahrenheit.

Many different materials can be suitable phase change materials as long as the materials have a melting temperature within the target range (as explained above). Entropy Solutions, Inc. has an office in Plymouth, Minn. and provides a wide range of suitable phase change materials under the brand name PureTemp. Climator Sweden AB sells a wide range of phase change materials under the brand name ClimSel. Examples of phase change materials include sodium sulfate, trimethylolethane combined with water, $Mn(NO3)2*6H2O+MnCl2*4H2O$, $NaCl*Na2SO4*10H2O$, paraffin 16-carbons, and paraffin 18-carbons.

In several embodiments, phase change materials spontaneously melt and/or solidify in response to temperature (without requiring an additional activation step). For example, just a drop in temperature below a melting temperature can cause a spontaneous phase change material to freeze. Just a rise in temperature above a melting temperature can cause a spontaneous phase change material to solidify.

The phase change materials are not the only part of the system that reduces the rate of temperature change inside the first chamber (e.g., the void 154). An insulated container can reduce the rate of heat transfer. Some embodiments include a vacuum flask. Thermos L.L.C. manufactures a wide range of vacuum flasks. The vacuum is a type of insulation.

Walls of vacuum flasks can be made of glass, stainless steel, or any other suitable material. Many components can be molded plastic.

Insulated containers can have rigid walls or compliant, flexible walls. For example, the insulated container can be a steel Thermos or an insulated, fabric pouch.

Storage systems can use many different types of insulation including multi-layer insulation, closed-cell insulation, closed-cell foam insulation, rubber foam insulation, nitrile rubber foam insulation, nitrile butadiene rubber insulation, polyurethane insulation, reflective foil layers, injected insulation, rigid insulation, flexible insulation, and/or vacuum insulation.

Some embodiments use a first vacuum flask inside a second vacuum flask to form a dual-vacuum layer system. The flask can include reflective walls to reduce heat transfer by radiation.

In several embodiments, the interior of the vacuum flask is cylindrical. The chambers that hold the phase change system plus the first chamber can form a cylindrical shape that is tailored to the interior of the vacuum flask. The phase change system can have a compliant external housing with an outer diameter that is larger than the diameter of an opening to the vacuum flask. The compliant external housing (e.g., a compliant perimeter) can enable pressing the phase change system into the vacuum flask in spite of the outer diameter of the external housing being larger than the diameter of the opening to the vacuum flask.

In several embodiments, storage systems include an insulated container comprising a base and an opening configurable to enable removing a medicine from inside the insulated container; a first chamber located inside the insulated container, wherein the first chamber is configured to hold the medicine; a first phase change material located inside the insulated container; and/or a second phase change material located inside the insulated container.

In some embodiments, the first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. The first melting temperature can be at least four degrees Fahrenheit less than the second melting temperature. For example, 74 degrees Fahrenheit can be approximately equal to a typical room temperature (although room temperatures commonly vary in rooms having temperature controlled environments enabled by heating and/or air conditioning).

Using a "temperature dividing line" of 74 degrees Fahrenheit helps enable some embodiments to avoid inappropriately triggering melting and/or freezing while the storage system is located in a temperature controlled room. Imagine if the second phase change material had a melting temperature of less than 74 degrees. As a result, the second phase change material could completely melt before a person even moved the storage system from a room temperature into a hot environment that is warmer than a maximum recommended storage temperature of the medicine. In this case the phase change of the second phase change material would not help reduce the rate of temperature rise inside the first chamber in response to heat transfer caused by the hot environment. Similarly, this "temperature dividing line" helps ensure that the first phase change material will have a sufficiently low melting temperature such that the first phase change material should not solidify before the storage system is moved from a room temperature to an environment that is colder than a minimum recommended storage temperature.

The "temperature dividing line" can vary based on what medicine the storage system will hold. For example, some medicine manufacturers recommend refrigerating certain medicines. In several embodiments, the temperature dividing line is 36 degrees Fahrenheit. Thus, the first phase change material can have a melting temperature above 0 degrees Fahrenheit and/or below 36 degrees Fahrenheit. The second phase change material can have a melting temperature above 36 degrees Fahrenheit and/or below 50 degrees Fahrenheit.

A "target temperature" can be a "temperature dividing line." In several embodiments, the target temperature can be 74 degrees Fahrenheit (e.g., when the manufacturer recommends storing a medicine at room temperature). In several embodiments, the target temperature can be 36 degrees Fahrenheit (e.g., when the manufacturer recommends refrigerating a medicine).

In some embodiments, the storage system is configured to cause the first phase change material to solidify when a first temperature of the first chamber falls below the first melting temperature, and/or the storage system is configured to cause the second phase change material to melt when the first temperature of the first chamber rises above the second melting temperature. As a result, the storage system can be configured to temporarily protect the medicine from a first environment that is colder than a safe minimum storage temperature and/or from a second environment that is hotter than a safe maximum storage temperature. Manufacturers of medicines can recommend minimum storage temperatures and/or maximum storage temperatures for medicines.

In several embodiments, the first phase change material has a first latent heat of at least 40 kJ/kg, and/or the second phase change material has a second latent heat of at least 40 kJ/kg. In some embodiments, the first phase change material has a first latent heat of at least 110 kJ/kg, and/or the second phase change material has a second latent heat of at least 110 kJ/kg. In several embodiments, the first phase change material has a first latent heat of at least 180 kJ/kg, and/or the second phase change material has a second latent heat of at least 180 kJ/kg. These latent heat properties can dramatically reduce the necessary size of the phase change materials, which enables dramatically reducing the overall volume of the storage system.

The chambers of a storage system can include different phase chamber materials. The phase change system can have more than two melting temperatures. In some embodiments, a second chamber contains a first phase change material having a first melting temperature; a third chamber contains a second phase change material having a second melting temperature; a fourth chamber contains a third phase change material having a third melting temperature; and a fifth chamber contains a fourth phase change material having a fourth melting temperature. The first and second melting temperatures can be less than a target temperature (e.g., 74 degrees Fahrenheit), and the first melting temperature can be less than (e.g., at least 3 degrees Fahrenheit less than) the second melting temperature. The third and fourth melting temperatures can be greater than the target temperature, and the third melting temperature can be less than (e.g., at least 3 degrees Fahrenheit less than) the fourth melting temperature.

A phase change system with more than two melting temperatures can provide additional temperature protection reliability. For example, a third phase change material can protect against temperatures that are just slightly above a target temperature (e.g., 74 degrees Fahrenheit, 36 degrees Fahrenheit). Thus, the system can protect against even minor temperature variations above the target temperature. However, phase change materials that protect against temperatures that are just slightly above a target temperature are susceptible to changing phase while the storage system is located indoors.

For example, a manufacturer can recommend a maximum EpiPen storage temperature of 77 degrees Fahrenheit, which is very close to typical room temperatures. The phase change system can include a third phase change material with a melting temperature of 76 degrees Fahrenheit. If the storage system is kept in a room that is below 76 degrees Fahrenheit for at least enough time for the third phase change material to solidify, then once the storage system is moved into an outdoor environment that is 79 degrees Fahrenheit, the third phase change material will begin protecting the EpiPen from the outdoor environment that is 79 degrees Fahrenheit.

However, if the storage system is kept in a room that is 78 degrees Fahrenheit for at least enough time for the third phase change material to melt, then once the storage system is moved into an outdoor environment that is 80 degrees Fahrenheit, the third phase change material will fail to protect the EpiPen from the outdoor environment that is 80 degrees Fahrenheit (because the phase change will have occurred before the storage system reaches the outdoor environment). In this case, having a fourth phase change material can be helpful. The fourth phase change material can have a fourth melting temperature that is not as close to typical room temperatures. For example, the fourth melting temperature can be 82 degrees Fahrenheit, which is typically higher than room temperatures. Thus, the fourth phase change material would not be melting while kept in a room that is 78 degrees Fahrenheit for at least enough time for the third phase change material to melt. Then, once the storage system is moved into an outdoor environment that is 80 degrees Fahrenheit, the fourth phase change material will protect the EpiPen from the outdoor environment that is 80 degrees Fahrenheit (by melting).

A manufacturer of a medicine can recommend a minimum storage temperature and a maximum storage temperature for the medicine. In some embodiments, the storage system includes a first phase change material with a first melting temperature that is lower than the target temperature and lower than the minimum storage temperature; the storage system includes a second phase change material with a second melting temperature that is lower than the target temperature, higher than the minimum storage temperature, and higher than the first melting temperature; the storage system includes a fourth phase change material with a fourth melting temperature that is higher than the target temperature and higher than the maximum storage temperature; and/or the storage system includes a third phase change material with a third melting temperature that is higher than the target temperature, lower than the maximum storage temperature, and lower than the fourth melting temperature.

Several phase change system embodiments include two different melting temperatures below a target temperature (e.g., 74 degrees Fahrenheit) and one melting temperature above the target temperature. Some phase change system embodiments include two different melting temperatures above a target temperature (e.g., 74 degrees Fahrenheit) and one melting temperature below the target temperature.

If a difference between a target temperature and an expected cold outdoor temperature is greater than a difference between the target temperature and an expected hot outdoor temperature, then the phase change system can include two different melting temperatures below the target temperature and one melting temperature above the target temperature.

If a difference between a target temperature and an expected hot outdoor temperature is greater than a difference between the target temperature and an expected cold outdoor temperature, then the phase change system can include two different melting temperatures above the target temperature and one melting temperature below the target temperature.

The expected cold outdoor temperature is less than the target temperature. The expected hot outdoor temperature is greater than the target temperature. The expected cold outdoor temperature can be the maximum expected cold outdoor temperature. The expected hot outdoor temperature can be the maximum expected hot outdoor temperature.

A manufacturer of a medicine can recommend a minimum storage temperature and a maximum storage temperature for the medicine. If a difference between a target temperature and the minimum storage temperature is greater than a difference between the target temperature and the maximum storage temperature, then the phase change system can include two different melting temperatures below the target temperature and one melting temperature above the target temperature.

If a difference between a target temperature and the maximum storage temperature is greater than a difference between the target temperature and the minimum storage temperature, then the phase change system can include two different melting temperatures above the target temperature and one melting temperature below the target temperature.

If a difference between the minimum storage temperature and the expected cold outdoor temperature is greater than a difference between the maximum storage temperature and the expected hot outdoor temperature, then the phase change system can include two different melting temperatures below the target temperature and one melting temperature above the target temperature.

If a difference between the maximum storage temperature and the expected hot outdoor temperature is greater than a difference between the minimum storage temperature and the expected cold outdoor temperature, then the phase change system can include two different melting temperatures above the target temperature and one melting temperature below the target temperature.

Any of the storage systems shown in the figures, described herein, and/or incorporated by reference can be configured according to the temperature information above and according to the phase change material information described above.

Any of the storage systems shown in the figures, described herein, or incorporated by reference can include three, four, or more phase change materials (e.g., each with different melting temperatures). The chambers described herein can be subdivided into additional chambers by walls to hold phase change materials with different melting temperatures.

In some embodiments in which a first phase change material has a melting temperature greater than 40 degrees Fahrenheit and less than 74 degrees Fahrenheit, the phase change material comprises at least one of PureTemp 6, PureTemp 15, PureTemp 18, and PureTemp 20 made by Entropy Solutions, Inc., which has an office in Plymouth, Minn. In some embodiments where a first phase change material has a melting temperature greater than 40 degrees Fahrenheit and less than 74 degrees Fahrenheit, the phase change material comprises at least one of Paraffin 14-Carbons, Paraffin 15-Carbons, and Paraffin 16-Carbons.

In some embodiments in which a second phase change material has a melting temperature greater than 74 degrees Fahrenheit and less than 100 degrees Fahrenheit, the phase change material comprises at least one of PureTemp 25, PureTemp 27, PureTemp 28, PureTemp 29, and PureTemp 35 made by Entropy Solutions, Inc., which has an office in Plymouth, Minn. In some embodiments where a second phase change material has a melting temperature greater than 74 degrees Fahrenheit and less than 100 degrees Fahrenheit, the phase change material comprises at least one of Paraffin 18-Carbons, Paraffin 19-Carbons, and Paraffin 20-Carbons.

Any of the embodiments illustrated herein and/or incorporated by reference can include a storage system comprising a phase change system; a first container configured to hold at least a portion of the phase change system; and a first chamber located within the first container and configured to hold a medicine. As explained above, phase change systems can comprise a first phase change material and/or a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. Thus, the phase change system can protect the medicine from temperatures above and below room temperature.

Refrigeration systems typically are large, expensive, fragile, and use electricity to regulate temperature. In contrast, phase change systems can be configured to protect medicine from a first external temperature less than a minimum recommended storage temperature and from a second external temperature greater than a maximum recommended storage temperature by utilizing phase changes to regulate a temperature of the medicine. Because phase change systems do not require electronics and pumps, they are very robust and can be built for a small fraction of the cost of refrigeration systems. Imagine a child who needs an epinephrine injector having to carry even a small refrigerator wherever she goes to prevent hot temperatures from ruining her potentially life-saving epinephrine.

In stark contrast, the child could easily carry a medicine storage system that relies on the phase change systems described herein, which can even be designed to protect against both hot and cold temperatures to eliminate the need for the child to have to guess which temperature protection components she will need for a trip. For example, if the child goes camping, she may need to protect her medicine against both hot afternoon temperatures and cold nighttime temperatures.

Containers can come in many different shapes and sizes. Some containers are vacuum flasks. Vacuum flasks can prevent high heat transfer rates to enable minimizing the amount of phase change material necessary to adequately protect a medicine. Thus, the system can be smaller than would be the case without a vacuum flask.

On the other hand, vacuum flasks often have rigid outer walls, which can make carrying them uncomfortable. Some containers are compliant bags with flexible walls. Compliant bags can be very comfortable to carry. Their flexible outer walls can facilitate fitting them into backpacks and purses (by enabling them to conform to various shapes).

In some cases, a medicine has a recommended minimum or maximum storage temperature that is close to a room temperature or 74 degrees Fahrenheit. This situation can be problematic because selecting a melting temperature (of a phase change material) that is close to room temperature or 74 degrees Fahrenheit can result in the phase change material changing phases before the phase change material leaves an indoor environment in which the storage system is stored.

For example, a house's internal temperature may be between 67 degrees Fahrenheit and 80 degrees Fahrenheit. If the minimum recommended storage temperature of a medicine is 69 degrees Fahrenheit, then the first phase change material may have a melting temperature of 69 degrees Fahrenheit. As a result, the first phase change material could freeze before the storage system ever leaves the house.

A solution to this problem is to have more than two melting temperatures of phase change materials in the storage system. For example, a first phase change material could have a melting temperature of 69 degrees Fahrenheit, a second phase change material could have a melting temperature of 81 degrees Fahrenheit, and a third phase change material could have a melting temperature of 65 degrees Fahrenheit. Thus, if the first phase change material freezes before the storage system leaves the house, then the third phase change material could provide backup protection against cold environments (even if this backup protection is slightly lower than the minimum recommended storage temperature).

Any of the embodiments described in any of the figures can include one, two, three, four, or more phase change materials with unique melting temperatures. Any of the embodiments can include a first phase change material having a first melting temperature greater than 40 degrees Fahrenheit and less than 74 degrees Fahrenheit, a second phase change material having a second melting temperature greater than 74 degrees Fahrenheit and less than 100 degrees Fahrenheit, a third phase change material having a third melting temperature less than the first melting temperature, and/or a fourth phase change material having a fourth melting temperature greater than the second melting temperature. In several embodiments, the third melting temperature is greater than 40 degrees Fahrenheit and less than 74 degrees Fahrenheit. In some embodiments, the fourth melting temperature is greater than 74 degrees Fahrenheit and less than 100 degrees Fahrenheit. These various phase change materials can be located in any of the chambers and containers described herein. In some embodiments, more than one phase change material is located in a single chamber. In several embodiments, different phase change materials are located in different chambers.

Any of the embodiments can include a first phase change material having a first melting temperature greater than 40 degrees Fahrenheit and less than 74 degrees Fahrenheit, a second phase change material having a second melting temperature greater than 74 degrees Fahrenheit and less than 100 degrees Fahrenheit, a third phase change material having a third melting temperature less than the first melting temperature, and/or a fourth phase change material having a fourth melting temperature greater than the second melting temperature. In several embodiments, the third melting temperature is greater than 40 degrees Fahrenheit and less than 74 degrees Fahrenheit. In some embodiments, the fourth melting temperature is greater than 74 degrees Fahrenheit and less than 100 degrees Fahrenheit.

In several embodiments, storage systems include "chambers" (e.g., to hold phase change material or other items). These chambers can be formed by containers having chambers. In some embodiments, a container has a single chamber to hold a phase change material. In several embodiments, a container has many chambers. In some embodiments, a first container has many containers (e.g., formed by walls inside the first container).

Some embodiments use iBeacon, which is a protocol standardized by Apple Inc. iBeacon can enable finding the location of a storage system and/or remote computing device indoors. Bluetooth low energy (LE) tracking devices can be attached to storage systems to enable the storage systems to broadcast their information to nearby remote computing devices.

Several embodiments use Radio-frequency identification (RFID), which is the wireless use of electromagnetic fields to transfer data. RFID can be used to identify and track tags attached to storage systems.

Some embodiments use Global Positioning Systems (GPS) to track storage systems. GPS is typically well-suited for outdoor tracking.

Manufacturers, physicians, and other entities often provide "instructions for use" with products. For example, a user might buy a storage system that has a first instruction to return the storage system to a room temperature or an indoor environment within 24 hours of entering a warmer or colder environment. This is a simplified way for a manufacturer to communicate thermal performance data to a user. In some cases, the instructions can be based on the temperature of the second, third, or outdoor environment. For example, a zero degree Fahrenheit environment might require returning the storage system to a room temperature or to an indoor environment within 12 hours while a 50 degree Fahrenheit environment might only require returning the storage system to a room temperature or to an indoor environment within 48 hours. These return instructions can be at least 4 hours and/or less than 48 hours; at least 6 hours and/or less than 24 hours; and/or at least 2 hours and/or less than 12 hours. Failing to comply with the return instructions could damage the medicine that is stored in the storage system.

Several embodiments include moving the storage system to a second environment that is cooler than the first environment, and then moving the storage system to a warmer environment, relative to the second environment, in response to a first instruction, wherein the first instruction is a first recommended maximum time that the storage system can be in the second environment that is cooler before being moved to the warmer environment.

Some embodiments include moving the storage system to a third environment that is warmer than the first environment, and then moving the storage system to a cooler environment, relative to the third environment, in response to a second instruction, wherein the second instruction is a second recommended maximum time that the storage system can be in the third environment that is warmer before being moved to the cooler environment.

Relying on time is not the only way for users to know when they need to move their storage device out of a hot or cold environment (e.g., an outdoor environment) and back into a room temperature or indoor environment. Some embodiments include indications that notify users to move the storage system out of a hot or cold environment (e.g., an outdoor environment) and back into a room temperature or indoor environment. For example, some embodiments include moving the storage system to a second environment (e.g., an outdoor environment) that is cooler than the first environment, and then moving the storage system to a warmer environment, relative to the second environment, in response to a first indication provided by at least one of the storage system and a remote computing device. The first indication can be at least one of a sound, a light, a temperature reading, an indicator on a mechanical display, and information on an electronic display. The warmer environment can be a room temperature environment and/or an indoor environment. Several embodiments include moving the storage system to a third environment (e.g., an outdoor environment) that is warmer than the first environment, and then moving the storage system to a cooler environment, relative to the third environment, in response to a second indication provided by at least one of the storage system and the remote computing device. The second indication can also be at least one of a sound, a light, a temperature reading, an indicator on a mechanical display, and information on an electronic display.

Several embodiments include placing the medicine in the phase change system to protect the medicine from a first external temperature less than a minimum recommended storage temperature and from a second external temperature greater than a maximum recommended storage temperature by utilizing phase changes to regulate a temperature of the medicine rather than by regulating the temperature using electricity.

Some embodiments include maintaining the first chamber in an open state (e.g., with the lid uncoupled from the base portion such that the lid does not shield the medicine's chamber from an external environment) with the medicine inside the first chamber while located indoors and/or in a room temperature environment; and then closing the first chamber in response to going outdoors, in preparation to go outdoors, in preparation to leave the room temperature environment, and/or in preparation to entering a second environment that is hotter or colder than the room temperature environment.

Several embodiments include closing the medicine within the first chamber to prepare the storage system for exiting a room temperature environment and/or opening the first chamber once inside a room temperature environment (e.g., in response to entering a room temperature environment).

Some embodiments include placing the medicine in the phase change system to protect the medicine from a first external temperature less than a room temperature and from a second external temperature greater than the room temperature by utilizing phase changes to regulate a temperature of the medicine. Several embodiments include regulating a temperature of the medicine by utilizing the first phase change material and the second phase change material to protect the medicine from a first external temperature less than a room temperature and from a second external temperature greater than the room temperature.

Many embodiments are described herein to communicate a vast number of features and methods. Describing all of the features and methods in every embodiment would lead to unnecessary redundancy. Each of the features and methods described herein can be included in each of the embodiments described herein. Thus, elements of one embodiment can be combined with elements of other embodiments.

Many embodiments described herein greatly benefit people by enabling them to take their temperature-sensitive medicines outdoors (even in hot or cold weather). Rather than risk being without their medicine (by leaving their medicine behind when going outdoors), the specially constructed storage systems described herein can protect medicines from damage due to hot and cold weather without requiring the bulky structures or expensive components of traditional refrigerators.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

We claim:

1. A medicine storage system comprising:
 an insulated container having an opening;
 a lid configured to cover the opening;
 a phase change system located inside the insulated container; and
 a tube located inside the insulated container such that the tube is in fluid communication with the opening, wherein the storage system is configured to enable inserting a medicine through the opening and into the tube,
 wherein the phase change system comprises a first phase change material and a second phase change material, the first phase change material having a first melting temperature greater than 40 degrees Fahrenheit and less than 74 degrees Fahrenheit, and the second phase change material having a second melting temperature greater than 74 degrees Fahrenheit and less than 100 degrees Fahrenheit.

2. The storage system of claim 1, wherein the phase change system comprises a first flexible bag having the first phase change material and a second flexible bag having the second phase change material.

3. The storage system of claim 2, wherein the first and second flexible bags are located inside the insulated container and outside the tube such that the first flexible bag is located between an inner wall of the insulated container and an outer wall of the tube.

4. The storage system of claim 3, wherein first and second flexible bags are mechanically coupled to each other but fluidly isolate the first phase change material from the second phase change material.

5. The storage system of claim 3, wherein the outer wall of the tube comprises a first ventilation channel configured to enable airflow between an area inside the tube and the phase change system.

6. The storage system of claim 5, wherein the outer wall of the tube comprises a second ventilation channel located on an opposite side of the tube relative to the first ventilation channel, and wherein the insulated container is insulated by a vacuum chamber.

7. The storage system of claim 2, wherein the first flexible bag comprises at least two fluidly isolated chambers having the first phase change material.

8. The storage system of claim 7, wherein the second flexible bag comprises at least two fluidly isolated chambers having the second phase change material, the first flexible bag is wrapped at least partially around the tube, and the second flexible bag is wrapped at least partially around the tube.

9. The storage system of claim 8, wherein at least one of the first flexible bag is wrapped at least partially around the second flexible bag and the second flexible bag is wrapped at least partially around the first flexible bag.

10. The storage system of claim 2, wherein the insulated container is insulated by a vacuum chamber, the phase change system is wrapped around the tube, the insulated container comprises a first central axis, the tube comprises a second central axis that is within 15 degrees of being aligned with the first central axis, and the tube extends from an upper half of the insulated container to a lower half of the insulated container.

11. The storage system of claim 2, wherein the phase change system is configured to protect the medicine from a first external temperature less than a minimum recommended storage temperature and from a second external temperature greater than a maximum recommended storage temperature by utilizing phase changes to regulate a temperature of the medicine,
 an injection device having epinephrine is located in the tube, and
 the storage system comprises a thermometer and a communication system configured to send data regarding a temperature inside the storage system to a remote computing device.

12. The storage system of claim 2, further comprising at least one flex arm configured to hold the tube inside the insulated container.

13. The storage system of claim 12, wherein the flex arm protrudes farther radially outward than a narrowest section of an interior of the insulated container such that the flex arm is configured to flex radially inward in response to inserting the tube into the insulated container and the flex arm is configured to contact a narrowing section of the interior to hold the tube inside the insulated container.

14. The storage system of claim 12, wherein the flex arm comprises a cantilever beam oriented within 80 degrees of a direction oriented along a central axis of the tube and towards the opening such that pulling the tube towards the opening increases a resistance of the flex arm to the pulling.

15. The storage system of claim 2, wherein the tube comprises at least one flex arm having a cantilever beam and a portion to engage an interior of the insulated container to hold the tube inside the insulated container.

16. The storage system of claim 2, wherein the tube is coupled to a bracket that holds the tube inside the insulated container.

17. The storage system of claim 2, wherein a maximum width of the opening is measured from a central axis of the insulated container in a direction perpendicular to the central axis, wherein the tube is coupled to a bracket having an outermost edge located farther from the central axis than the maximum width such that the bracket holds the tube inside the insulated container.

18. The storage system of claim 2, further comprising a spring located in the insulated container, wherein the spring is configured to push the medicine towards the opening.

19. The storage system of claim 18, further comprising a platform located inside the tube such that the spring pushes the platform towards the opening to push the medicine at least partially out of the opening so a user can pull the medicine out of the storage system.

20. A medicine storage system comprising:
an insulated container having an opening;
a phase change system located inside the insulated container, wherein the phase change system comprises a first phase change material and a second phase change material, the first phase change material having a first melting temperature greater than 40 degrees Fahrenheit and less than 74 degrees Fahrenheit, and the second phase change material having a second melting temperature greater than 74 degrees Fahrenheit and less than 100 degrees Fahrenheit; and
a lid configured to cover the opening, wherein the lid comprises a thread configured to couple the lid to the insulated container.

21. The storage system of claim 20, wherein the lid comprises a rotational release mechanism configured such that the lid is rotatable relative to the insulated container in a first rotational direction that tightens the lid to the insulated container and in a second rotational direction that loosens the lid from the insulated container,
the lid comprises a first portion and a second portion, wherein the first portion comprises the thread that couples the lid to the insulated container,
the second portion of the lid is configured to rotate in the first rotational direction relative to the first portion of the lid in response to a first applied torque that exceeds a release threshold, and
the second portion of the lid is configured to resist rotation in the second rotational direction relative to the first portion in a presence of a second applied torque that is at least thirty percent larger than a magnitude of the release threshold.

22. The storage system of claim 21, wherein the rotational release mechanism comprises an interface between the first portion and the second portion, the interface having teeth slanted such that rotating the second portion relative to the first portion of the lid in the first rotational direction requires a lower torque than rotating the second portion relative to the first portion of the lid in the second rotational direction.

23. The storage system of claim 20, wherein the lid comprises at least one tooth that protrudes from of the lid, and the tooth is slanted such that the tooth provides greater grip when unscrewing the lid from the insulated container than when screwing the lid into the insulated container.

24. The storage system of claim 1,
wherein the insulated container is insulated by a vacuum chamber, and
wherein at least a portion of the phase change system is located between an inner wall of the insulated container and an outer wall of the tube such that the storage system is configured to enable a user to remove the lid, insert the medicine through the opening and into the tube, and replace the lid.

25. The storage system of claim 24, wherein an interior of the insulated container comprises a first cylindrical section and a second cylindrical section that is closer to the opening than the first cylindrical section, the second cylindrical section having a second diameter that is smaller than a first diameter of the first cylindrical section, the first cylindrical section having a first length measured along a central axis of the insulated container, the second cylindrical section having a second length measured along the central axis of the insulated container, the first length being at least twice as long as the second length,
wherein the tube comprises a third cylindrical section having a third diameter and a third length that is measured along a central axis of the tube, and the tube comprises a fourth cylindrical section having a fourth diameter and a fourth length that is measured along the central axis of the tube,
wherein the fourth cylindrical section couples the third cylindrical section to the opening of the insulated container, the fourth diameter being larger than the third diameter, the third length being at least twice as long as the fourth length, and
wherein at least one of the second cylindrical section and a portion of the insulated container located radially outward from the second cylindrical section comprise a thread configured to couple the lid to the insulated container.

26. The storage system of claim 1, wherein the phase change system comprises a first bag having the first phase change material,
the insulated container is insulated by a vacuum chamber,
the first bag is located inside the insulated container and at least partially outside the tube such that the first bag is located at least partially between an inner wall of the insulated container and an outer wall of the tube, and
the tube extends from an upper half of the insulated container to a lower half of the insulated container such that the storage system is configured to enable a user to remove the lid, insert the medicine through the opening and into the tube, replace the lid, and protect the medicine from temperatures below 40 degrees Fahrenheit.

27. The storage system of claim 1, further comprising the medicine located at least partially inside the tube, wherein the phase change system comprises a first bag having the second phase change material,
- the first bag is located inside the insulated container and at least partially outside the tube such that the first bag is located at least partially between an inner wall of the insulated container and an outer wall of the tube, and
- the tube extends from an upper half of the insulated container to a lower half of the insulated container such that the storage system is configured to enable a user to remove the lid, insert the medicine through the opening and into the tube, replace the lid, and protect the medicine from temperatures above 100 degrees Fahrenheit.

28. A medicine storage system comprising:
- an insulated container having an opening;
- a lid configured to cover the opening; and
- a phase change system located inside the insulated container, wherein the phase change system comprises a first bag having a first phase change material and a second bag having a second phase change material, the first phase change material having a first melting temperature greater than 40 degrees Fahrenheit and less than 74 degrees Fahrenheit, and the second phase change material having a second melting temperature greater than 74 degrees Fahrenheit and less than 100 degrees Fahrenheit.

29. The storage system of claim 28, wherein at least one of the first and second bags comprises compliant walls.

30. The storage system of claim 28, wherein at least one of the first and second bags comprises film walls.

31. The storage system of claim 28, wherein the first and second bags are sealed pouches.

32. The storage system of claim 28, wherein the first and second bags are mechanically coupled to each other but fluidly isolate the first phase change material from the second phase change material.

33. The storage system of claim 28, wherein the first bag comprises at least two fluidly isolated chambers having the first phase change material.

34. The storage system of claim 28, wherein at least one of the first bag is wrapped at least partially around the second bag and the second bag is wrapped at least partially around the first bag.

35. The storage system of claim 28, further comprising the medicine located inside the insulated container such that at least one of the first and second bags is wrapped at least partially around the medicine.

36. The storage system of claim 28, further comprising the medicine located at least partially inside a tube that is located inside the insulated container, wherein the first and second bags are located inside the insulated container and at least partially outside the tube such that the second bag is located at least partially between an inner wall of the insulated container and an outer wall of the tube.

37. The storage system of claim 28, further comprising a thermometer and a communication system coupled to at least one of the insulated container and the lid, wherein the thermometer and the communication system are configured to send data regarding a temperature inside the storage system to a remote computing device.

* * * * *